United States Patent
Elias et al.

(10) Patent No.: US 11,478,530 B2
(45) Date of Patent: Oct. 25, 2022

(54) METHODS FOR DECREASING CHORD LENGTH

(71) Applicants: BROWN UNIVERSITY, Providence, RI (US); YALE UNIVERSITY, New Haven, CT (US)

(72) Inventors: Jack A. Elias, Providence, RI (US); Chun Geun Lee, Woodbridge, CT (US); Min-Jong Kang, Scarsdale, NY (US)

(73) Assignees: BROWN UNIVERSITY, Providence, RI (US); YALE UNIVERSITY, New Haven, CT (US)

( * ) Notice: Subject to any disclaimer, the term of this patent is extended or adjusted under 35 U.S.C. 154(b) by 880 days.

(21) Appl. No.: 16/059,445

(22) Filed: Aug. 9, 2018

(65) Prior Publication Data

US 2019/0030119 A1 Jan. 31, 2019

Related U.S. Application Data

(63) Continuation of application No. 15/065,230, filed on Mar. 9, 2016, now abandoned.

(60) Provisional application No. 62/130,811, filed on Mar. 10, 2015.

(51) Int. Cl.
*A61K 38/17* (2006.01)
*A61K 48/00* (2006.01)
*G01N 33/68* (2006.01)

(52) U.S. Cl.
CPC ....... *A61K 38/177* (2013.01); *G01N 33/6872* (2013.01); *G01N 2800/122* (2013.01); *G01N 2800/52* (2013.01)

(58) Field of Classification Search
CPC .............. A61K 48/00; A61K 38/177
See application file for complete search history.

(56) References Cited

U.S. PATENT DOCUMENTS

| | | | |
|---|---|---|---|
| 2013/0203716 A1* | 8/2013 | Fox | A61K 31/522 |
| | | | 514/171 |
| 2015/0037362 A1* | 2/2015 | Kagan | C07K 14/4702 |
| | | | 424/185.1 |
| 2015/0037441 A1* | 2/2015 | Kim | A23L 33/105 |
| | | | 424/750 |
| 2015/0352108 A1* | 12/2015 | Holcomb | A61P 43/00 |
| | | | 514/157 |
| 2020/0010417 A1* | 1/2020 | Bassaganya-Riera | A61P 35/00 |
| 2020/0255378 A1* | 8/2020 | Bassaganya-Riera | C07D 239/34 |

OTHER PUBLICATIONS

Auphan, N., et al. Immunosuppression by glucocorticoids: inhibition of NF-κB activity through induction of IκB synthesis. Science, 1995, 270:286-290.*
Ngkelo, A., et al. New treatments for COPD. Curr. Opin. Pharmacol., 2013, 13:362-369.*
Xia, X., et al. NLRX1 negatively regulates TLR-induced NF-κB signaling by targeting TRAF6 and IKK. Immunity, 2011, 34(6):843-853.*
Allen et al., "NLRX1 Protein Attenuates Inflammatory Responses to Infection by Interfering with the RIG-I-MAVS and TRAF6-NF-κB Signaling Pathways", Immunity 34(6):854-865 (2011).
Belgnaoui et al., "Orchestrating the interferon antiviral response through the mitochondrial antiviral signaling (MAVS) adapter", Current Opinion in Immunology 23(5):564-572 (2011).
Kang et al., "Cigarette Smoke-Induced Suppression of NLRX1 Enhances Inflammasome Activation and Alveolar Destruction", Am J Respir Crit Care Med. 187:A1098 (2013).
Kang et al., "Cigarette smoke selectively enhances viral PAMP— and virus-induced pulmonary innate immune and remodeling responses in mice", The Journal of Clinical Investigation 118(8):2771-2784 (2008).
Kang et al., "Suppression of NLRX1 in chronic obstructive pulmonary disease." The Journal of Clinical Investigation 125(6):2458-2462 (2015).
Lei et al., "The mitochondrial proteins NLRX1 and TUFM form a complex that regulates type I interferon and autophagy", Immunity 36(6):933-946 (2012).
Moore et al., "NLRX1 is a regulator of mitochondrial antiviral immunity", Nature 451(7178):573-577 (2008).

* cited by examiner

*Primary Examiner* — Prema M Mertz
(74) *Attorney, Agent, or Firm* — Adler Pollack & Sheehan P.C.

(57) ABSTRACT

The methods and assays described herein relate to the diagnosis, prognosis, and treatment of subjects with emphysema, COPD, and/or cigarette-induced lung damage. In some embodiments, the methods and assays relate to subjects with a decreased level of NLRX1 expression. In some embodiments, the methods and assays relate to the administration of an agonist of NLRX1 and/or an inhibitor of MAVS.

2 Claims, 12 Drawing Sheets

Specification includes a Sequence Listing.

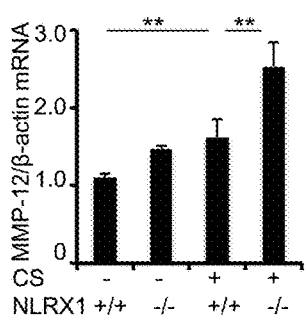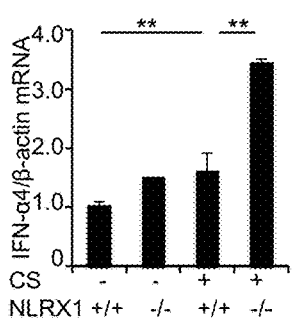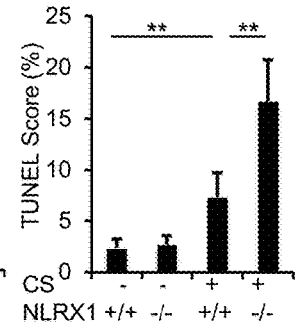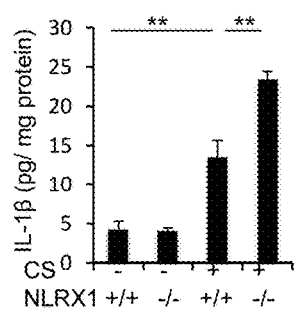
Fig. 2G    Fig. 2H    Fig. 2I    Fig. 2J
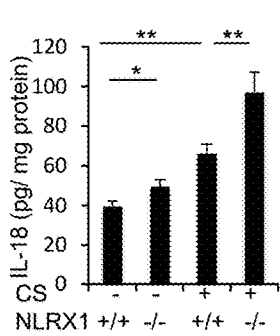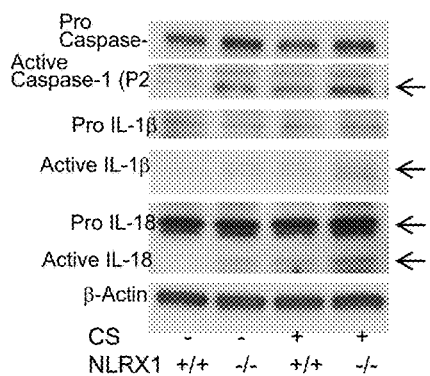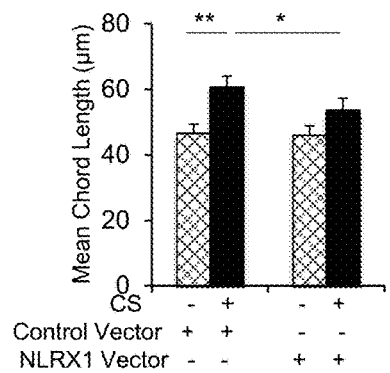
Fig. 2K    Fig. 2L    Fig. 2M
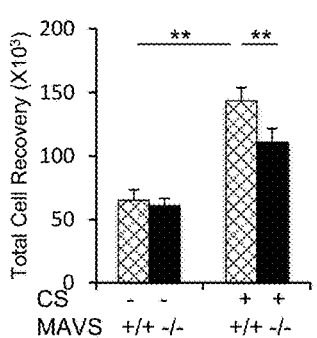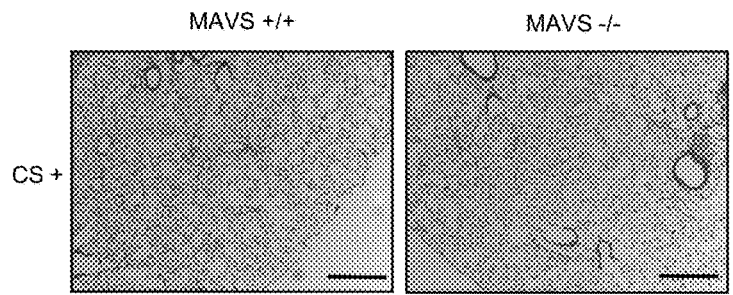
Fig. 3A    Fig. 3B

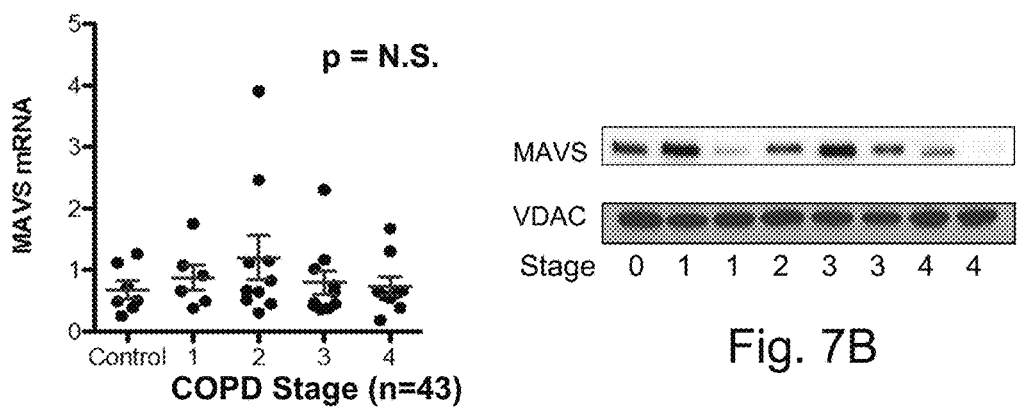
Fig. 7A
Fig. 7B
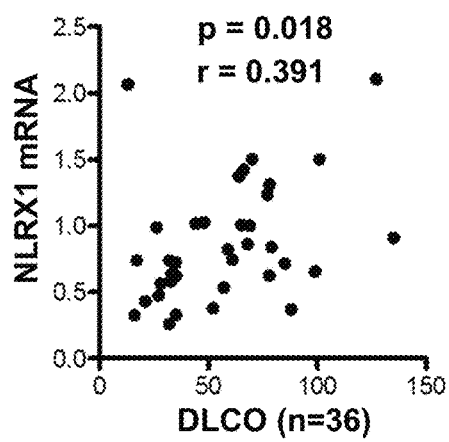
Fig. 8A
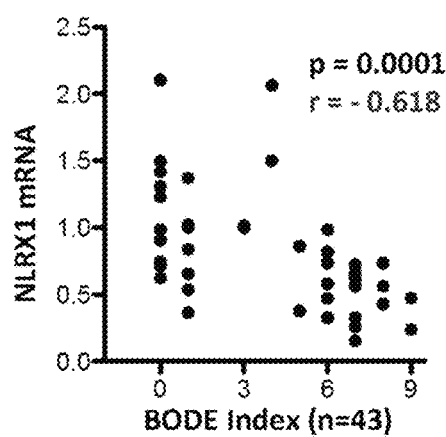
Fig. 8B
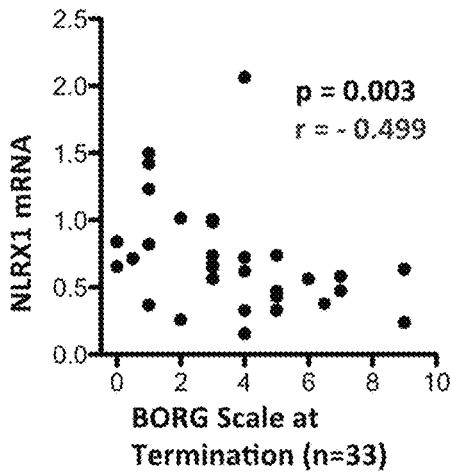
Fig. 8C

US 11,478,530 B2

METHODS FOR DECREASING CHORD LENGTH

CROSS-REFERENCE TO RELATED APPLICATIONS

This application is a continuation under 35 U.S.C. § 120 of co-pending U.S. application Ser. No. 15/065,230 filed Mar. 9, 2016, which claims benefit under 35 U.S.C. § 119(e) of U.S. Provisional Application No. 62/130,811 filed Mar. 10, 2015, the contents of which are incorporated herein by reference in their entirety.

GOVERNMENT SUPPORT

This invention was made with federal funding under Grant Nos. R56HL119511, HL-079328, and PO1 HL114501 awarded by the National Institutes of Health. The U.S. government has certain rights in the invention.

SEQUENCE LISTING

The instant application contains a Sequence Listing which has been submitted electronically in ASCII format and is hereby incorporated by reference in its entirety. Said ASCII copy, created on Feb. 4, 2016, is named 058040-084261-US SL.txt and is 34,231 bytes in size.

TECHNICAL FIELD

The technology described herein relates to the diagnosis, prognosis, and treatment of lung disease, e.g. COPD, emphysema, and/or cigarette smoke-induced lung damage.

BACKGROUND

Cigarette smoke causes a broad spectrum of diseases characterized by inflammation and tissue remodeling, including chronic obstructive pulmonary disease (COPD). In many of these disorders the inflammation is believed to drive disease pathogenesis. This can be seen in COPD, the fourth leading cause of death in the world, where pulmonary inflammation is believed to be causally related to the emphysema and other pathologic alterations in the lungs from these patients.

Cigarette smoke activates caspase 1 and IL-18, thereby regulating the inflammasome. However, the mechanism(s) that controls lung inflammasome activation at baseline and the alterations that cigarette smoke induces to activate the inflammasome have not been defined.

SUMMARY

MAVS (mitochondrial antiviral signaling molecule) regulates inflammatory and remodeling responses in viral infections and is inhibited in the healthy, non-infected lung. It is demonstrated herein that cigarette smoke causes damage to lung tissue, at least in part, by inhibiting NLRX1, which inhibits MAVS in healthy tissue. Thus, cigarette smoke causes an increase in the activity of MAVS, resulting in inflammation and pathological tissue remodeling. Restoration of NLRX1 in lung exposed to cigarette smoke reserved the pathological effects of cigarette smoke. Accordingly, provided herein are methods of diagnosing, prognosing, and treating COPD, emphysema, and/or cigarette smoke-induced lung damage relating to the discovery that NLRX1 is suppressed in diseased tissues.

In one aspect, described herein is a method of treating COPD in a subject in need thereof, the method comprising administering an inhibitor of MAVS. In one aspect, described herein is a method of treating cigarette smoke-induced lung damage in a subject in need thereof, the method comprising administering an inhibitor of MAVS. In some embodiments, the cigarette smoke-induced lung damage is selected from the group consisting of: inflammation; alveolar destruction; protease induction; structural cell apoptosis; and inflammasome activation. In one aspect, described herein is a method of treating emphysema in a subject in need thereof, the method comprising administering an inhibitor of MAVS. In some embodiments, the emphysema is cigarette smoke induced emphysema.

In some embodiments, the inhibitor of MAVS is an agonist of NLRX1. In some embodiments, the inhibitor of MAVS is a modulator of NLRX1-dependent pathways. In some embodiments, the agonist of NLRX1 is a nucleic acid encoding NLRX1 or an NLRX1 polypeptide.

In one aspect, described herein is a method of treating COPD in a subject in need thereof, the method comprising administering an inhibitor of MAVS.

In one aspect, described herein is a method of treating cigarette smoke-induced lung damage in a subject in need thereof, the method comprising administering an agonist of NLRX1. In some embodiments, the cigarette smoke-induced lung damage is selected from the group consisting of: inflammation; alveolar destruction; protease induction; structural cell apoptosis; and inflammasome activation. In one aspect, described herein is a method of treating emphysema in a subject in need thereof, the method comprising administering an agonist of NLRX1. In some embodiments, the emphysema is cigarette smoke induced emphysema.

In some embodiments, the subject is a subject determined to have a decreased level of NLRX1 expression.

In one aspect, described herein is an assay comprising: measuring the level of NLRX1 in a test sample obtained from a subject; wherein an decrease in the expression level relative to a reference level indicates the subject has a higher risk of having or developing COPD, emphysema, and/or cigarette-induced lung damage. In one aspect, described herein is a method of identifying a subject in need of treatment for COPD, emphysema, and/or cigarette-induced lung damage, the method comprising: measuring the level of NLRX1 in a test sample obtained from a subject; and identifying the subject as being in need of treatment for COPD, emphysema, and/or cigarette-induced lung damage when the expression level of NLRX1 is decreased relative to a reference level. In one aspect, described herein is a method of determining if a subject is at risk for COPD, emphysema, and/or cigarette-induced lung damage, the method comprising: measuring the level of NLRX1 in a test sample obtained from a subject; comparing the level of NLRX1 in the sample to a reference level of NLRX1; determining that the subject is at risk for COPD, emphysema, and/or cigarette-induced lung damage when the level of NLRX1 is decreased relative to a reference level; and determining that the subject is not at risk for COPD, emphysema, and/or cigarette-induced lung damage when the level of NLRX1 is not decreased relative to a reference level. In one aspect, described herein is a method of determining the efficacy of a treatment for COPD, emphysema, and/or cigarette-induced lung damage, the method comprising: (a) measuring the level of NLRX1 in a test sample obtained from a subject before administration of the treatment; (b) measuring the level of NLRX1 in a test sample obtained from a subject after administration of the treatment; (c) determining that the treatment is efficacious when the expression level determined in step (b) is not decreased relative to the expression level determined in step (a); and (d) determining that the treatment is not efficacious when the expression level determined in step (b) is decreased relative to the expression level determined in step (a). In one aspect, described herein is a method of treatment for COPD, emphysema, and/or cigarette-induced lung damage comprising; measuring the level of NLRX1 in a test sample obtained from a subject; treating the subject when the level of NLRX1 is decreased relative to a reference level. In one aspect, described herein is a method of treatment for COPD, emphysema, and/or cigarette-induced lung damage comprising; treating a subject determined to have a level of NLRX1 which is decreased relative to a reference level. In some embodiments, the treatment comprises a treatment selected from the group consisting of: administration of a bronchodilator; administration of an inhaled steroid; administration of oxygen therapy; bullectomy; lung volume reduction surgery; smoking cessation; lung transplant; administration of an inhibitor of MAVS; administration of an agonist of NLRX1; administration of a nucleic acid encoding NLRX1; and administration of an NLRX1 polypeptide.

In some embodiments, the level of NLRX1 is determined by measuring the level of a nucleic acid. In some embodiments, the level of NLRX1 is determined by measuring the level of NLRX1 RNA transcript. In some embodiments, the level of the nucleic acid is determined using a method selected from the group consisting of: RT-PCR; quantitative RT-PCR; Northern blot; microarray based expression analysis; next-generation sequencing; and RNA in situ hybridization. In some embodiments, the level of NLRX1 is determined by measuring the level of NLRX1 polypeptide. In some embodiments, the level of the polypeptide is determined using a method selected from the group consisting of Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay. In some embodiments, the polypeptide level is measured using immunochemistry. In some embodiments, the antibody reagent is detectably labeled or generates a detectable signal.

In some embodiments, the expression level of NLRX1 is normalized relative to the expression level of one or more reference genes or reference proteins. In some embodiments, the reference level of NLRX1 is the expression level of NLRX1 in a prior sample obtained from the subject. In some embodiments, the subject is a subject with a history of smoking. In some embodiments, the sample is selected from the group consisting of: a lung biopsy; bronchoalveolar lavage (BAL); sputum; induced sputum; blood; plasma; and serum. In some embodiments, the method or assay further comprises the step of treating the subject with a treatment selected from the group consisting of: administration of a bronchodilator; administration of an inhaled steroid; administration of oxygen therapy; bullectomy; lung volume reduction surgery; smoking cessation; lung transplant; administration of an inhibitor of MAVS; administration of an agonist of NLRX1; administration of a nucleic acid encoding NLRX1; and administration of an NLRX1 polypeptide.

In one aspect, described herein is a kit for performing the method or assay of the foregoing aspects.

BRIEF DESCRIPTION OF THE DRAWINGS

In FIG. 1B the levels of NLRX1 are compared in no disease (controls, 0) and patients with, mild to moderate (GOLD 1 and 2) and severe COPD (GOLD 3 and 4). The levels of NLRX1 protein in mitochondria-enriched tissue fractions (MF) from controls (0) and GOLD 1, 2, 3, and 4 individuals were evaluated by western blot analysis (FIG. 1C). The levels of NLRX1 protein in these western evaluations were evaluated by densitometry and compared to the levels of expression of the voltage dependent anion channel (VDAC) ( $p<0.01$). The correlations between the levels of NLRX1 mRNA in the LTRC samples and pre-bronchodilator $FEV_1$(% of predicted value) (FIG. 1D) and post-bronchodilator $FEV_1$(% of predicted value) (FIG. 1E) are also illustrated. FIG. 1F depicts is a box-whiskers plot from the Pittsburgh cohort describing the relationship between NLRX1 gene expression in microarray evaluations and radiologic emphysema ( $p<0.05$ compared to control and the >40% emphysema group). From the Asan cohort, the standardized levels of NLRX1 gene transcriptome were plotted in controls and in patients with COPD (FIG. 1G). In FIG. 1H the levels of NLRX1 gene expression are compared in no disease (controls) and patients with COPD of varying severity (GOLD 1, 2, and 3). The bars in FIGS. 1A, 1B, and 1G represent the mean±SEM of the noted evaluations. The statistics that were applied were the nonparametric Kruskal-Wallis test (FIG. 1A), Mann-Whitney U test (FIGS. 1B and 1C), Pearson correlation analysis (FIGS. 1D and 1E), two-tailed unpaired t-test (FIGS. 1F and 1G) and ANOVA test (FIG. 1H). In FIGS. 1F and 1H, the box shows the mean and standard deviation of the group and the whiskers show minimum and maximum expression values.

FIGS. 2A-2M demonstrate that cigarette smoke (CS)-induced suppression of NLRX1 and the role of NLRX1 in CS-induced pulmonary inflammation and alveolar destruction. NLRX1 mRNA (FIG. 2A) and protein (FIG. 2B) are suppressed by CS exposure. In FIG. 2B, the bar graph to the right of the gel represents the results of densitometry comparing the levels of NLRX1 and voltage dependent anion channel (VDAC) in mitochondria-enriched fractions (MF) and cytosol-enriched fractions (CF). After 3 months of CS exposure, western blot analysis of the NLRX1 protein expression in BAL cells are presented in FIG. 2C. After 3 months of CS exposure, the roles of NLRX1 were evaluated using comparisons of responses in wild type (WT) and NLRX1 null mice. BAL total cell recovery (FIG. 2D), representative histology (FIG. 2E), lung morphometry (FIG. 2F), the expression of MMP-12 mRNA (FIG. 2G), the expression of interferon (IFN)-alpha (a) 4 mRNA, and TUNEL evaluation of structural (epithelial and endothelial) cells (FIG. 2I) are illustrated. The levels of active IL-1β (FIG. 2J) and IL-18 (FIG. 2K) in lung lysates were also measured by ELISA. In panel (FIG. 2L), western blot evaluations of lung tissue lysates are used to characterize the activation status of IL-1β, IL-18 and caspase-1. In FIG. 2M, the measurement of mean chord length is presented from lentiviral NLRX1 overexpressed mice (NLRX1 vector+) and appropriate controls (control vector+) after 6 month-CS-exposure. Size bar on FIG. 2E represents 400 μm. The values in FIGS. 2A, 2D, 2F-2K and 2M represent the mean±SEM of evaluations in a minimum of 5 mice (* $p<0.05$, ** $p<0.01$). FIGS. 2B, 2C, and 2L are representative of a minimum of 3 similar experiments.

FIGS. 3A-3K demonstrate the role of MAVS in CS-induced pulmonary inflammation and alveolar destruction.

After 6 months of CS exposure, the roles of MAVS were evaluated using comparisons of responses in WT and MAVS null mice. BAL total cell recovery (FIG. 3A), representative histology (FIG. 3B), lung morphometry (FIG. 3C) and the expression of MMP-12 mRNA (FIG. 3D) are illustrated. In FIG. 3E, western blot evaluations of lung tissue lysates were used to demonstrate the activation status of IL-18 and caspase-1. The results of TUNEL evaluations of structural cells (FIG. 3F), the expression of interferon (IFN)-α4 mRNA (FIG. 3G) and the expression of NLRX1 mRNA (FIG. 3H) are also illustrated. The results of the evaluation of mean chord length (FIG. 3I), TUNEL evaluations of structural cells (FIG. 3J) and the measurement of the level of IL-18 in lung tissues (FIG. 3K) are presented from MAVS$^{-/-}$/NLRX1$^{-/-}$ mice, NLRX1$^{-/-}$ mice and wild type (MAVS$^{+/+}$/NLRX1$^{+/+}$) controls after 3 month-CS-exposure. Size bar on FIG. 3B represents 400 µm. The values in FIGS. 3A, 3C, 3D, and 3F-3K represent the mean±SEM of evaluations in a minimum of 5 mice. (* $p<0.05$, ** $p<0.01$). FIG. 3E is representative of a minimum of 3 similar evaluations.

FIGS. 7A-7B demonstrate the levels of (FIG. 7A) MAVS mRNA and (FIG. 7B) protein in LTRC samples were plotted in controls (0) and in patients with COPD of varying severity (GOLD 1, 2, 3, and 4).

FIGS. 8A-8C demonstrate the correlations between the levels of NLRX1 mRNA and (FIG. 8A) diffusing capacity (DLCO), (FIG. 8B) BODE index, and (FIG. 8C) BORG scale, respectively, in the LTRC cohort.

DETAILED DESCRIPTION

Figure 1A:
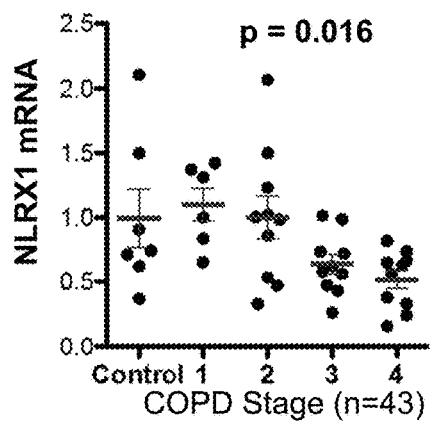
FIGS. 1A-1H demonstrate NLRX1 mRNA suppression in patients with COPD and its correlation with disease severity. The levels of NLRX1 mRNA in LTRC samples were plotted in controls (0) and in patients with COPD of varying severity (GOLD 1, 2, 3, and 4) (FIG. 1A).

As described herein, the inventors have found that inhibition of MAVS, e.g., by stimulating NLRX1 activity, has a therapeutic effect on lung diseases, e.g. COPD, emphysema, and/or cigarette smoke-induced lung damage. Accordingly, provided herein are methods of treating COPD, emphysema, and/or cigarette smoke-induced lung damage by administering an inhibitor of MAVS and/or an agonist of NLRX1.

As used herein, "emphysema" refers to a chronic lung disease which affects the alveoli and/or the ends of the smallest bronchi. The condition is characterized by destructive changes and enlargement of the alveoli (air sacs) within the lungs. The lung loses its elasticity and therefore these areas of the lungs become enlarged. These enlarged areas trap stale air and do not effectively exchange it with fresh air. This results in difficult breathing and may result in insufficient oxygen being delivered to the blood. The predominant symptom in patients with emphysema is shortness of breath. In some embodiments, the emphysema can be cigarette-smoke induced emphysema. As used herein, "COPD" or "chronic obstructive pulmonary disease" is generally applied to chronic respiratory disease processes characterized by the persistent obstruction of bronchial air flow. COPD patients can suffer from conditions such as bronchitis, cystic fibrosis, asthma or emphysema. As used herein, "cigarette smoke-induced lung damage" refers to damage to lung tissues occurring in subjects exposed to cigarette smoke, including but not limited to: inflammation; alveolar destruction; protease induction; structural cell apoptosis; and inflammasome activation. Cigarette smoke-induced lung damage can be present in a subject having or diagnosed as having emphysema or COPD or in a subject not having or not diagnosed as having emphysema or COPD. In some embodiments of any of the aspects described herein, the patient can be a patient with a history of smoking.

As used herein, "MAVS" or "mitochondrial antiviral-signaling protein" refers to a protein found in the mitochondria, that when aggregated, activates IRF3 dimerization, contributing to the recognition of virii. MAVS is also known in the art as VISA, IPS-1, and Cardif. Sequences for MAVS expression products are known for a number of species, e.g., human MAVS (NCBI Gene ID: 57506) mRNA (SEQ ID NO: 3; NCBI Ref Seq: NM_020746) and polypeptide (SEQ ID NO: 4; NCBI Ref Seq: NP_065797).

As used herein, "inhibitor" refers to an agent which can decrease the expression and/or activity of the targeted expression product (e.g. mRNA encoding the target or a target polypeptide), e.g. by at least 10% or more, e.g. by 10% or more, 50% or more, 70% or more, 80% or more, 90% or more, 95% or more, or 98% or more. The efficacy of an inhibitor of, for example, MAVS, e.g. its ability to decrease the level and/or activity of MAVS can be determined, e.g. by measuring the level of an expression product of MAVS and/or the activity of MAVS. Methods for measuring the level of a given mRNA and/or polypeptide are known to one of skill in the art, e.g. RTPCR with primers can be used to determine the level of RNA and Western blotting with an antibody (e.g. an anti-MAVS antibody, e.g. Cat No. ab189109 Abcam; Cambridge, Mass.) can be used to determine the level of a polypeptide. The activity of, e.g. MAVS can be determined using methods known in the art and described elsewhere herein, e.g., by measuring the levels of expression of CXCL13, MMP-12, cathepsisn K, cathepsin S, type 1 IFNs, caspase 1, IL-1β, and/or IL-18, where decreased MAVS levels and/or activity results in decreased levels of CXCL13, MMP-12, cathepsisn K, cathepsin S, type 1 IFNs, caspase 1, IL-1β, and/or IL-18. In some embodiments, the inhibitor can be an inhibitory nucleic acid; an aptamer; an antibody reagent; an antibody; or a small molecule.

In some embodiments, an inhibitor of MAVS can be an agonist of NLRX1. In some embodiments, an inhibitor of MAVS can be a modulator of NLRX1-dependent pathways.

As used herein, "NLRX1" or "nucleotide-binding oligomerization domain leucine rich repeat containing X1" refers to an intracellular signaling protein with a N-terminal mitochondrion localization signal, a NACHT domain, an a C-terminal LRR. NLRX1 is also known in the art as NODS, NODS, and CLR11.3. Sequences for NLRX1 expression products are known for a number of species, e.g., human NLRX1 (NCBI Gene ID: 79671) mRNA (SEQ ID NO: 1; NCBI Ref Seq: NM_001282144) and polypeptide (SEQ ID NO: 2; NCBI Ref Seq: NP_001269073).

As used herein, "agonist" refers to any agent that increases the level and/or activity of the target, e.g., of NLRX1. As used herein, the term "agonist" refers to an agent which increases the expression and/or activity of the target by at least 10% or more, e.g. by 10% or more, 50% or more, 100% or more, 200% or more, 500% or more, or 1000% or more. The efficacy of an agonist of, for example, NLRX1, e.g. its ability to decrease the level and/or activity of NLRX1 can be determined, e.g. by measuring the level of an expression product of NLRX1 and/or the activity of NLRX1. Methods for measuring the level of a given mRNA and/or polypeptide are known to one of skill in the art, e.g. RTPCR with primers can be used to determine the level of RNA and Western blotting with an antibody (e.g. an anti-NLRX1 antibody, e.g. Cat No. ab105412 Abcam; Cambridge, Mass.) can be used to determine the level of a polypeptide. The activity of, e.g. NLRX1 can be determined using methods known in the art and described elsewhere herein, e.g., by measuring the levels of expression of CXCL13, MMP-12, cathepsisn K, cathepsin S, type 1 IFNs, caspase 1, IL-1β, and/or IL-18, where increased NLRX1 levels and/or activity results in decreased levels of CXCL13, MMP-12, cathepsisn K, cathepsin S, type 1 IFNs, caspase 1, IL-1β, and/or IL-18. Non-limiting examples of agonists of NLRX1 can include NLRX1 polypeptides or fragments thereof and nucleic acids encoding a NLRX1 polypeptide, e.g. a polypeptide comprising the sequence SEQ ID NO: 2 or a nucleic acid comprising the sequence of SEQ ID NO: 1 or variants thereof. In some embodiments, the agonist of NRLX1 can be an NLRX1 polypeptide. In some embodiments, the agonist of NLRX1 can be an engineered and/or recombinant polypeptide. In some embodiments, the agonist of NLRX1 can be a nucleic acid encoding NLRX1, e.g. a functional fragment thereof.

In some embodiments, the agonist of NLRX1 can be a modulator of an NLRX1-dependent pathway. NLRX1-dependent pathways are known in the art and described, e.g., in Allen et al. Front Immunol 2014 5:169; which is incorporated by reference herein in its entirety. By way of non-limiting example, a modulator of an NLRX1-dependent pathway suitable for use in the methods described herein can be an inhibitor of TRAF6, IKK-gamma, IKK-alpha/beta, IκB, p65, p50, RIG1, TBK1, IRF, IFN-1, and/or IL-6.

In some embodiments, a therapy as described herein, e.g. an inhibitor of MAVS and/or an agonist of NLRX1 can be targeted to the mitochondria. Targeting can be achieved, e.g. by conjugating the agent to a targeting group or including the agent in a composition comprising a targeting group (e.g. a nanoparticle). Targeting groups can include, e.g., a cell or tissue targeting agent, e.g., a lectin, glycoprotein, lipid or protein, e.g., an antibody, that binds to a specified cell type such as lung cell, among others, or a cell permeation agent. Non-limiting examples of mitochondrial targeting groups can include triphenylphosphonium (TPP); mitochondrial targeting sequence polypeptides, and the like. Mitochondrial targeting is further described in the art, see, e.g., Weinberg and Chandel Nat Chem Biol 2015 11:9-15; Dongworth et al. Future Cardiol 2014 10:255-272; and Sureshbabu Front Physiol 2013 4:384; each of which is incorporated by reference herein in its entirety.

As described herein, decreased levels of NLRX1 expression and/or activity indicate that a subject has an increased risk of having and/or developing COPD, emphysema, and/or cigarette smoke-induced lung damage. Accordingly, in some embodiments of any of the aspects described herein, the subject that is treated in accordance with the methods described herein is a subject having or identified as having a decreased level of NLRX1 expression and/or activity.

In one aspect, described herein is an assay comprising: measuring the level of NLRX1 in a test sample obtained from a subject; wherein an decrease in the expression level relative to a reference level indicates the subject has a higher risk of having or developing COPD, emphysema, and/or cigarette-induced lung damage. In one aspect, described herein is a method of identifying a subject in need of treatment for COPD, emphysema, and/or cigarette-induced lung damage, the method comprising: measuring the level of NLRX1 in a test sample obtained from a subject; and identifying the subject as being in need of treatment for COPD, emphysema, and/or cigarette-induced lung damage when the expression level of NLRX1 is decreased relative to a reference level. In one aspect, described herein is a method of determining if a subject is at risk for COPD, emphysema, and/or cigarette-induced lung damage, the method comprising: measuring the level of NLRX1 in a test sample obtained from a subject; comparing the level of NLRX1 in the sample to a reference level of NLRX1; determining that the subject is at risk for COPD, emphysema, and/or cigarette-induced lung damage when the level of NLRX1 is decreased relative to a reference level; and determining that the subject is not at risk for COPD, emphysema, and/or cigarette-induced lung damage when the level of NLRX1 is not decreased relative to a reference level. In some embodiments, the level of NLRX1 is decreased relative to a reference amount if it is less than the reference amount by a statistically significant amount.

In some embodiments, measurement of the level of a target, e.g. of an NLRX1 expression product can comprise a transformation. As used herein, the term "transforming" or "transformation" refers to changing an object or a substance, e.g., biological sample, nucleic acid or protein, into another substance. The transformation can be physical, biological or chemical. Exemplary physical transformation includes, but not limited to, pre-treatment of a biological sample, e.g., from whole blood to blood serum by differential centrifugation. A biological/chemical transformation can involve at least one enzyme and/or a chemical reagent in a reaction. For example, a DNA sample can be digested into fragments by one or more restriction enzyme, or an exogenous molecule can be attached to a fragmented DNA sample with a ligase. In some embodiments, a DNA sample can undergo enzymatic replication, e.g., by polymerase chain reaction (PCR).

Transformation, measurement, and/or detection of a target molecule, e.g. a NLRX1 mRNA or polypeptide can comprise contacting a sample obtained from a subject with a reagent (e.g. a detection reagent) which is specific for the target, e.g., a NLRX1-specific reagent. In some embodiments, the target-specific reagent is detectably labeled. In some embodiments, the target-specific reagent is capable of generating a detectable signal. In some embodiments, the target-specific reagent generates a detectable signal when the target molecule is present.

Methods to measure NLRX1 gene expression products are well known to a skilled artisan. Such methods to measure gene expression products, e.g., protein level, include ELISA (enzyme linked immunosorbent assay), western blot, immunoprecipitation, and immunofluorescence using detection reagents such as an antibody or protein binding agents. Alternatively, a peptide can be detected in a subject by introducing into a subject a labeled anti-peptide antibody and other types of detection agent. For example, the antibody can be labeled with a detectable marker whose presence and location in the subject is detected by standard imaging techniques.

For example, antibodies for NLRX1 are commercially available and can be used for the purposes of the invention to measure protein expression levels, e.g. anti-NLRX1 (Cat. No. ab105412; Abcam, Cambridge Mass.). Alternatively, since the amino acid sequences for NRLX1 are known and publically available at NCBI website, one of skill in the art can raise their own antibodies against these polypeptides of interest for the purpose of the invention.

The amino acid sequences of the polypeptides described herein, e.g. NLRX1 have been assigned NCBI accession numbers for different species such as human, mouse and rat. In particular, the NCBI accession numbers for the amino acid sequence of human NLRX1 is included herein, e.g. SEQ ID NO: 2.

In some embodiments, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of an antibody, wherein the antibodies are used to specifically target molecules inside or on the surface of cells. The antibody typically contains a marker that will undergo a biochemical reaction, and thereby experience a change of color, upon encountering the targeted molecules. In some instances, signal amplification can be integrated into the particular protocol, wherein a secondary antibody, that includes the marker stain or marker signal, follows the application of a primary specific antibody.

In some embodiments, the assay can be a Western blot analysis. Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. These methods also require a considerable amount of cellular material. The analysis of 2D SDS-PAGE gels can be performed by determining the intensity of protein spots on the gel, or can be performed using immune detection. In other embodiments, protein samples are analyzed by mass spectroscopy.

Immunological tests can be used with the methods and assays described herein and include, for example, competitive and non-competitive assay systems using techniques such as Western blots, radioimmunoassay (RIA), ELISA (enzyme linked immunosorbent assay), "sandwich" immunoassays, immunoprecipitation assays, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays (CLIA), electrochemiluminescence immunoassay (ECLIA, counting immunoassay (CIA), lateral flow tests or immunoassay (LFIA), magnetic immunoassay (MIA), and protein A immunoassays. Methods for performing such assays are known in the art, provided an appropriate antibody reagent is available. In some embodiment, the immunoassay can be a quantitative or a semi-quantitative immunoassay.

An immunoassay is a biochemical test that measures the concentration of a substance in a biological sample, typically a fluid sample such as urine, using the interaction of an antibody or antibodies to its antigen. The assay takes advantage of the highly specific binding of an antibody with its antigen. For the methods and assays described herein, specific binding of the target polypeptides with respective proteins or protein fragments, or an isolated peptide, or a fusion protein described herein occurs in the immunoassay to form a target protein/peptide complex. The complex is then detected by a variety of methods known in the art. An immunoassay also often involves the use of a detection antibody.

Enzyme-linked immunosorbent assay, also called ELISA, enzyme immunoassay or EIA, is a biochemical technique used mainly in immunology to detect the presence of an antibody or an antigen in a sample. The ELISA has been used as a diagnostic tool in medicine and plant pathology, as well as a quality control check in various industries.

In one embodiment, an ELISA involving at least one antibody with specificity for the particular desired antigen (e.g., NLRX1 as described herein) can also be performed. A known amount of sample and/or antigen is immobilized on a solid support (usually a polystyrene micro titer plate). Immobilization can be either non-specific (e.g., by adsorption to the surface) or specific (e.g. where another antibody immobilized on the surface is used to capture antigen or a primary antibody). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In another embodiment, a competitive ELISA is used. Purified antibodies that are directed against a target polypeptide or fragment thereof are coated on the solid phase of multi-well plate, i.e., conjugated to a solid surface. A second batch of purified antibodies that are not conjugated on any solid support is also needed. These non-conjugated purified antibodies are labeled for detection purposes, for example, labeled with horseradish peroxidase to produce a detectable signal. A sample (e.g., a blood sample) from a subject is mixed with a known amount of desired antigen (e.g., a known volume or concentration of a sample comprising a target polypeptide) together with the horseradish peroxidase labeled antibodies and the mixture is then are added to coated wells to form competitive combination. After incubation, if the polypeptide level is high in the sample, a complex of labeled antibody reagent-antigen will form. This complex is free in solution and can be washed away. Washing the wells will remove the complex. Then the wells are incubated with TMB (3, 3', 5, 5'-tetramethylbenzidene) color development substrate for localization of horseradish peroxidase-conjugated antibodies in the wells. There will be no color change or little color change if the target polypeptide level is high in the sample. If there is little or no target polypeptide present in the sample, a different complex in formed, the complex of solid support bound antibody reagents-target polypeptide. This complex is immobilized on the plate and is not washed away in the wash step. Subsequent incubation with TMB will produce much color change. Such a competitive ELSA test is specific, sensitive, reproducible and easy to operate.

There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; and Oellerich, M. 1984, J. Clin. Chem. Clin. Biochem. 22:895-904. These references are hereby incorporated by reference in their entirety.

In one embodiment, the levels of a polypeptide in a sample can be detected by a lateral flow immunoassay test (LFIA), also known as the immunochromatographic assay, or strip test. LFIAs are a simple device intended to detect the presence (or absence) of antigen, e.g. a polypeptide, in a fluid sample. There are currently many LFIA tests are used for medical diagnostics either for home testing, point of care testing, or laboratory use. LFIA tests are a form of immunoassay in which the test sample flows along a solid substrate via capillary action. After the sample is applied to the test strip it encounters a colored reagent (generally comprising antibody specific for the test target antigen) bound to microparticles which mixes with the sample and transits the substrate encountering lines or zones which have been pretreated with another antibody or antigen. Depending upon the level of target polypeptides present in the sample the colored reagent can be captured and become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water, and/or homogenized tissue samples etc. Strip tests are also known as dip stick test, the name bearing from the literal action of "dipping" the test strip into a fluid sample to be tested. LFIA strip tests are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles which are labeled with antibodies raised to the target antigen. The test line will also contain antibodies to the same target, although it may bind to a different epitope on the antigen. The test line will show as a colored band in positive samples. In some embodiments, the lateral flow immunoassay can be a double antibody sandwich assay, a competitive assay, a quantitative assay or variations thereof. Competitive LFIAs are similar to competitive ELISA. The sample first encounters colored particles which are labeled with the target antigen or an analogue. The test line contains antibodies to the target/its analogue. Unlabelled antigen in the sample will block the binding sites on the antibodies preventing uptake of the colored particles. The test line will show as a colored band in negative samples. There are a number of variations on lateral flow technology. It is also possible to apply multiple capture zones to create a multiplex test.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Examples of patents that describe the use of "dip stick" technology to detect soluble antigens via immunochemical assays include, but are not limited to U.S. Pat. Nos. 4,444,880; 4,305,924; and 4,135,884; which are incorporated by reference herein in their entireties. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teachings of this "dip stick" technology for the detection of polypeptides using antibody reagents as described herein.

Other techniques can be used to detect the level of a polypeptide in a sample. One such technique is the dot blot, and adaptation of Western blotting (Towbin et al, Proc. Nat. Acad. Sci. 76:4350 (1979)). In a Western blot, the polypeptide or fragment thereof can be dissociated with detergents and heat, and separated on an SDS-PAGE gel before being transferred to a solid support, such as a nitrocellulose or PVDF membrane. The membrane is incubated with an antibody reagent specific for the target polypeptide or a fragment thereof. The membrane is then washed to remove unbound proteins and proteins with non-specific binding. Detectably labeled enzyme-linked secondary or detection antibodies can then be used to detect and assess the amount of polypeptide in the sample tested. The intensity of the signal from the detectable label corresponds to the amount of enzyme present, and therefore the amount of polypeptide. Levels can be quantified, for example by densitometry.

In some embodiments, the level of, e.g., NLRX1, can be measured, by way of non-limiting example, by Western blot; immunoprecipitation; enzyme-linked immunosorbent assay (ELISA); radioimmunological assay (MA); sandwich assay; fluorescence in situ hybridization (FISH); immunohistological staining; radioimmunometric assay; immunofluoresence assay; mass spectroscopy and/or immunoelectrophoresis assay.

In certain embodiments, the gene expression products as described herein can be instead determined by determining the level of messenger RNA (mRNA) expression of the genes described herein, e.g. NLRX1. Such molecules can be isolated, derived, or amplified from a biological sample, such as a blood sample. Techniques for the detection of mRNA expression is known by persons skilled in the art, and can include but not limited to, PCR procedures, RT-PCR, quantitative RT-PCR Northern blot analysis, differential gene expression, RNA protection assay, microarray based analysis, next-generation sequencing; hybridization methods, etc.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments, the level of an mRNA can be measured by a quantitative sequencing technology, e.g. a quantitative next-generation sequence technology. Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore). Exemplary methods of sequencing include, but are not limited to, Sanger sequencing, dideoxy chain termination, high-throughput sequencing, next generation sequencing, 454 sequencing, SOLiD sequencing, polony sequencing, Illumina sequencing, Ion Torrent sequencing, sequencing by hybridization, nanopore sequencing, Helioscope sequencing, single molecule real time sequencing, RNAP sequencing, and the like. Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humanna Press, 2011; and Sambrook et al., Molecular Cloning: A Laboratory Manual (4 ed.), Cold Spring Harbor Laboratory Press, Cold Spring Harbor, N.Y., USA (2012); which are incorporated by reference herein in their entireties.

The nucleic acid sequences of the genes described herein, e.g., NLRX1, have been assigned NCBI accession numbers for different species such as human, mouse and rat. For example, the human NRLX1 mRNA (e.g. SEQ ID NO: 1) is known. Accordingly, a skilled artisan can design an appropriate primer based on the known sequence for determining the mRNA level of the respective gene.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In some embodiments, one or more of the reagents (e.g. an antibody reagent and/or nucleic acid probe) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled reagent is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocyanate (TRITC)), biotin, phycoerythrin, AMCA, CyDyes™, 6-carboxyfhiorescein (commonly known by the abbreviations FAM and F), 6-carboxy-2',4', 7',4,7-hexachlorofiuorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes;

acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments, a detectable label can be a radiolabel including, but not limited to $^3$H, $^{125}$I, $^{35}$S, $^{14}$C, $^{32}$P, and $^{33}$P. In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments, a detectable label is a chemiluminescent label, including, but not limited to lucigenin, luminol, luciferin, isoluminol, theromatic acridinium ester, imidazole, acridinium salt and oxalate ester. In some embodiments, a detectable label can be a spectral colorimetric label including, but not limited to colloidal gold or colored glass or plastic (e.g., polystyrene, polypropylene, and latex) beads.

In some embodiments, detection reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, Calif. A reagent can also be detectably labeled using fluorescence emitting metals such as $^{152}$Eu, or others of the lanthanide series. These metals can be attached to the reagent using such metal chelating groups as diethylenetriaminepentaacetic acid (DTPA) or ethylenediaminetetraacetic acid (EDTA).

A level which is less than a reference level can be a level which is less by at least about 10%, at least about 20%, at least about 50%, at least about 600%, at least about 80%, at least about 90%, or less than the reference level. In some embodiments, a level which is less than a reference level can be a level which is statistically significantly less than the reference level. In some embodiments, the reference can be a level of NLRX1 in a population of subjects who do not have or are not diagnosed as having, and/or do not exhibit signs or symptoms of COPD, emphysema, and/or cigarette smoke-induced lung damage. In some embodiments, the reference can also be a level of expression of NLRX1 in a control sample, a pooled sample of control individuals or a numeric value or range of values based on the same. In some embodiments, the reference can be the level of NLRX1 in a sample obtained from the same subject at an earlier point in time, e.g., the methods described herein can be used to determine if a subject's risk or likelihood of developing COPD, emphysema, and/or cigarette smoke-induced lung damage is increasing.

In some embodiments, the level of expression products of no more than 200 other genes is determined. In some embodiments, the level of expression products of no more than 100 other genes is determined. In some embodiments, the level of expression products of no more than 20 other genes is determined. In some embodiments, the level of expression products of no more than 10 other genes is determined.

In some embodiments of the foregoing aspects, the expression level of a given gene, e.g., NLRX1, can be normalized relative to the expression level of one or more reference genes or reference proteins.

The term "sample" or "test sample" as used herein denotes a sample taken or isolated from a biological organism, e.g., a blood or plasma sample from a subject. Exemplary biological samples include, but are not limited to, a biofluid sample; serum; plasma; urine; saliva; and/or tissue sample etc. The term also includes a mixture of the above-mentioned samples. The term "test sample" also includes untreated or pretreated (or pre-processed) biological samples. In some embodiments, a test sample can comprise cells from subject. In some embodiments, the test sample can be a lung biopsy; bronchoalveolar lavage (BAL); sputum; induced sputum; blood; plasma; and serum.

The test sample can be obtained by removing a sample from a subject, but can also be accomplished by using previously sample (e.g. isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In some embodiments, the methods, assays, and systems described herein can further comprise a step of obtaining a test sample from a subject. In some embodiments, the subject can be a human subject. In some embodiments, the subject can be a subject in need of treatment for (e.g. having or diagnosed as having) COPD, emphysema, and/or cigarette smoke-induced lung damage.

In one aspect, described herein is a method of determining the efficacy of a treatment for COPD, emphysema, and/or cigarette-induced lung damage, the method comprising: (a) measuring the level of NLRX1 in a test sample obtained from a subject before administration of the treatment; (b) measuring the level of NLRX1 in a test sample obtained from a subject after administration of the treatment; (c) determining that the treatment is efficacious when the expression level determined in step (b) is not decreased relative to the expression level determined in step (a); and (d) determining that the treatment is not efficacious when the expression level determined in step (b) is decreased relative to the expression level determined in step (a).

In one aspect, described herein is a method of treatment for COPD, emphysema, and/or cigarette-induced lung damage comprising; measuring the level of NLRX1 in a test sample obtained from a subject; treating the subject when the level of NLRX1 is decreased relative to a reference level. In one aspect, described herein is a method of treatment for COPD, emphysema, and/or cigarette-induced lung damage comprising; treating a subject determined to have a level of NLRX1 which is decreased relative to a reference level. Treatments for COPD, emphysema, and cigarette smoke-induced lung damage are known in the art and can include, by way of non-limiting example administration of a bronchodilator; administration of an inhaled steroid; administration of oxygen therapy; bullectomy; lung volume reduction surgery; smoking cessation; and lung transplant. In some embodiments, a treatment for COPD, emphysema, and/or cigarette smoke-induced lung damage can include administration of an inhibitor of MAVS; administration of an agonist of NLRX1; administration of a nucleic acid encoding NLRX1; and/or administration of an NLRX1 polypeptide.

In some embodiments, the methods described herein relate to treating a subject having or diagnosed as having, e.g., emphysema with an inhibitor of MAVS and/or an agonist of NLRX1. Subjects having emphysema can be identified by a physician using current methods of diagnosing emphysema. Symptoms and/or complications of emphysema which characterize these conditions and aid in diagnosis are well known in the art and include but are not limited to, shortness of breath. Tests that may aid in a diagnosis of, e.g. emphysema include, but are not limited to, chest X-rays, CT scans, blood oxygenation tests, and lung function tests. A family history of emphysema, or exposure to risk factors for emphysema (e.g. smoking) can also aid in determining if a subject is likely to have emphysema or in making a diagnosis of emphysema.

The compositions and methods described herein can be administered to a subject having or diagnosed as having COPD, emphysema, and/or cigarette smoke-induced lung damage. In some embodiments, the methods described herein comprise administering an effective amount of compositions described herein, e.g. an inhibitor of MAVS and/or an agonist of NLRX1 to a subject in order to alleviate a symptom of COPD, emphysema, and/or cigarette smoke-induced lung damage. As used herein, "alleviating a symptom" of a disease or condition is ameliorating any condition or symptom associated with the disease or condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, or injection administration. Administration can be local or systemic.

The term "effective amount" as used herein refers to the amount of an inhibitor of MAVS and/or an agonist of NLRX1 needed to alleviate at least one or more symptom of the disease or disorder, and relates to a sufficient amount of pharmacological composition to provide the desired effect. The term "therapeutically effective amount" therefore refers to an amount of an inhibitor of MAVS and/or an agonist of NLRX1 that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of an inhibitor of MAVS and/or an agonist of NLRX1, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for inflammation in the lungs, among others. The dosage can be determined by a physician and adjusted, as necessary, to suit observed effects of the treatment.

In some embodiments, the technology described herein relates to a pharmaceutical composition comprising an inhibitor of MAVS and/or an agonist of NLRX1 as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23)

serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. an inhibitor of MAVS and/or an agonist of NLRX1 as described herein.

In some embodiments, the pharmaceutical composition comprising an inhibitor of MAVS and/or an agonist of NLRX1 as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of an inhibitor of MAVS and/or an agonist of NLRX1 as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an inhibitor of MAVS and/or an agonist of NLRX1 as disclosed herein can also be incorporated into the parenteral dosage forms of the disclosure, including conventional and controlled-release parenteral dosage forms.

Pharmaceutical compositions comprising an inhibitor of MAVS and/or an agonist of NLRX1 can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

A composition comprising an inhibitor of MAVS and/or agonist of NLRX1 can be administered directly to the airways of a subject in the form of an aerosol or by nebulization. For use as aerosols, an inhibitor of MAVS and/or agonist of NLRX in solution or suspension may be packaged in a pressurized aerosol container together with suitable propellants, for example, hydrocarbon propellants like propane, butane, or isobutane with conventional adjuvants. An inhibitor of MAVS and/or agonist of NLRX1 can also be administered in a non-pressurized form such as in a nebulizer or atomizer.

The term "nebulization" is well known in the art to include reducing liquid to a fine spray. Preferably, by such nebulization small liquid droplets of uniform size are produced from a larger body of liquid in a controlled manner. Nebulization can be achieved by any suitable means therefore, including by using many nebulizers known and marketed today. For example, an AEROMIST pneumatic nebulizer available from Inhalation Plastic, Inc. of Niles, Ill. When the active ingredients are adapted to be administered, either together or individually, via nebulizer(s) they can be in the form of a nebulized aqueous suspension or solution, with or without a suitable pH or tonicity adjustment, either as a unit dose or multidose device.

As is well known, any suitable gas can be used to apply pressure during the nebulization, with preferred gases to date being those which are chemically inert to a modulator of an inhibitor of MAVS and/or agonist of NLRX1. Exemplary gases including, but are not limited to, nitrogen, argon or helium can be used to high advantage.

In some embodiments, an inhibitor of MAVS and/or agonist of NLRX1 can also be administered directly to the airways in the form of a dry powder. For use as a dry powder, an inhibitor of MAVS and/or agonist of NLRX1 can be administered by use of an inhaler. Exemplary inhalers include metered dose inhalers and dry powdered inhalers.

A metered dose inhaler or "MDI" is a pressure resistant canister or container filled with a product such as a pharmaceutical composition dissolved in a liquefied propellant or micronized particles suspended in a liquefied propellant. The propellants which can be used include chlorofluorocarbons, hydrocarbons or hydrofluoroalkanes. Especially preferred propellants are P134a (tetrafluoroethane) and P227 (heptafluoropropane) each of which may be used alone or in combination. They are optionally used in combination with one or more other propellants and/or one or more surfactants and/or one or more other excipients, for example ethanol, a lubricant, an anti-oxidant and/or a stabilizing agent. The correct dosage of the composition is delivered to the patient.

A dry powder inhaler (i.e. Turbuhaler (Astra AB)) is a system operable with a source of pressurized air to produce dry powder particles of a pharmaceutical composition that is compacted into a very small volume.

Dry powder aerosols for inhalation therapy are generally produced with mean diameters primarily in the range of <5 μm. As the diameter of particles exceeds 3 μm, there is increasingly less phagocytosis by macrophages. However, increasing the particle size also has been found to minimize the probability of particles (possessing standard mass density) entering the airways and acini due to excessive deposition in the oropharyngeal or nasal regions.

Suitable powder compositions include, by way of illustration, powdered preparations of an inhibitor of MAVS and/or agonist of NLRX1 thoroughly intermixed with lactose, or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation. The compositions can include propellants, surfactants, and co-solvents and may be filled into conventional aerosol containers that are closed by a suitable metering valve.

Aerosols for the delivery to the respiratory tract are known in the art. See for example, Adjei, A. and Garren, *J. Pharm. Res.*, 1: 565-569 (1990); Zanen, P. and Lamm, J.-W. J. *Int. J. Pharm.*, 114: 111-115 (1995); Gonda, I. "Aerosols for delivery of therapeutic an diagnostic agents to the respiratory tract," in *Critical Reviews in Therapeutic Drug Carrier Systems*, 6:273-313 (1990); Anderson et al., *Am. Rev. Respir. Dis.*, 140: 1317-1324 (1989)) and have potential for the systemic delivery of peptides and proteins as well (Patton and Platz, *Advanced Drug Delivery Reviews*, 8:179-196 (1992)); Timsina et. al., *Int. J. Pharm.*, 101: 1-13 (1995); and Tansey, I. P., *Spray Technol. Market*, 4:26-29 (1994); French, D. L., Edwards, D. A. and Niven, R. W., *Aerosol Sci.*, 27: 769-783 (1996); Visser, J., *Powder Technology* 58: 1-10 (1989)); Rudt, S. and R. H. Muller, *J. Controlled Release*, 22: 263-272 (1992); Tabata, Y, and Y. Ikada, *Biomed. Mater. Res.*, 22: 837-858 (1988); Wall, D. A., *Drug Delivery*, 2: 10 1-20 1995); Patton, J. and Platz, R., *Adv. Drug Del. Rev.*, 8: 179-196 (1992); Bryon, P., *Adv. Drug. Del. Rev.*, 5: 107-132 (1990); Patton, J. S., et al., *Controlled Release*, 28: 15 79-85 (1994); Damms, B. and Bains, W., *Nature Biotechnology* (1996); Niven, R. W., et al., *Pharm. Res.*, 12(9); 1343-1349 (1995); and Kobayashi, S., et al., *Pharm. Res.*, 13(1): 80-83 (1996), contents of all of which are herein incorporated by reference in their entirety.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the inhibitor of MAVS and/or agonist of NLRX1 can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. By way of non-limiting example, if a subject is to be treated with an NLRX1 agonist according to the methods described herein, the subject can also be administered a second agent and/or treatment known to be beneficial for subjects suffering from COPD, emphysema, and/or cigarette smoke-induced lung damage. Examples of such agents and/or treatments include, but are not limited to, administration of a bronchodilator; administration of an inhaled steroid; administration of oxygen therapy; bullectomy; lung volume reduction surgery; and smoking cessation.

In certain embodiments, an effective dose of a composition comprising an inhibitor of MAVS and/or an agonist of NLRX1 as described herein can be administered to a patient once. In certain embodiments, an effective dose of a composition comprising an inhibitor of MAVS and/or an agonist of NLRX1 can be administered to a patient repeatedly. For systemic administration, subjects can be administered a therapeutic amount of a composition comprising an inhibitor of MAVS and/or an agonist of NLRX1, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an inhibitor of MAVS and/or an agonist of NLRX1 can be administered over a period of time, such as over a 5 minute, 10 minute, 15 minute, 20 minute, or 25 minute period.

The dosage ranges for the administration of an inhibitor of MAVS and/or an agonist of NLRX1, according to the methods described herein depend upon, for example, the form of the inhibitor of MAVS and/or agonist of NLRX1, its potency, and the extent to which symptoms, markers, or indicators of a condition described herein are desired to be reduced, for example the percentage reduction desired for inflammation or the extent to which, for example, NLRX1 expression levels are desired to be induced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an inhibitor of MAVS and/or an agonist of NLRX1 in, e.g. the treatment of a condition described herein, or to induce a response as described herein (e.g. NLRX1 activity and/or expression) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. NLRX1 activity and/or expression). It is well within the ability of one skilled in the art to monitor efficacy of administration and/or treatment by measuring any one of such parameters, or any combination of parameters. Efficacy can be assessed in animal models of a condition described herein, for example treatment of emphysema and/or COPD. When using an experimental animal model, efficacy of treatment is evidenced when a statistically significant change in a marker is observed, e.g. lung volume, surface area, and/or chord length.

In vitro and animal model assays are provided herein which allow the assessment of a given dose of inhibitor of MAVS and/or an agonist of NLRX1. By way of non-limiting example, the effects of a dose of inhibitor of MAVS and/or an agonist of NLRX1 can be assessed by measuring the levels of expression of CXCL13, MMP-12, cathepsisn K, cathepsin S, type 1 IFNs, caspase 1, IL-1β, and/or IL-18, where increased NLRX1 levels and/or activity results in decreased levels of CXCL13, MMP-12, cathepsisn K, cathepsin S, type 1 IFNs, caspase 1, IL-1β, and/or IL-18 and where decreased MAVS levels and/or activity results in decreased levels of CXCL13, MMP-12, cathepsisn K, cathepsin S, type 1 IFNs, caspase 1, IL-1β, and/or IL-18.

The efficacy of a given dosage combination can also be assessed in an animal model, e.g. a mouse model of cigarette smoke-induced lung damage. For example, mice can be exposed to cigarette smoke and a therapeutic agent or control intranasally. Lung tissue can be harvested at the desired time point and mean chord length and the surface area of the lungs determined following stereological analysis of the lungs according to the ATS/ERS guidelines. Briefly, the left lung can be inflated with 0.5% low temperature-melting agarose in 10% buffered formalin fixative at a constant pressure of 25 cm. After the fixation, lung volume ($V_L$) of the left lung was determined by the water immersion method. Images can be taken equally spaced and systematically placed meander-like over the whole surface of the lung sections. Pictures can be quantitatively analyzed by using a test system of points and lines superimposed over the digital images via the STEPanizer™ program. The intersecting points falling on alveolar space (Pa), alveolar ducts (Pd), and points falling on septum (Ps) can be counted separately among total points (Ptotal). Point counts yielded relative volume densities and alveolar surface area (S) can be calculated by the following formula; (1) Airspace fraction ($F_A$)=(Pa+Pd+Ps)/Ptotal; (2) Airspace volume ($V_A$)=$F_A \times V_L$; (3) S=$4V_A$/Lm (mean linear intercept).

In one aspect, described herein is a kit for performing any of the assays and/or methods described herein. In some embodiments, the kit can comprise a NLRX1-specific reagent.

A kit is any manufacture (e.g., a package or container) comprising at least one reagent, e.g., an antibody reagent(s) or nucleic acid probe, for specifically detecting, e.g., a NLRX1 expression product or fragment thereof, the manufacture being promoted, distributed, or sold as a unit for performing the methods or assays described herein. When the kits, and methods described herein are used for diagnosis and/or treatment of COPD, emphysema, and/or cigarette-induced lung damage in patients, the reagents (e.g., detection probes) or systems can be selected such that a positive result is obtained in at least about 20%, at least about 40%, at least about 60%, at least about 80%, at least about 90%, at least about 95%, at least about 99% or in 100% of subjects having or developing COPD, emphysema, and/or cigarette-induced lung damage.

In some embodiments, described herein is a kit for the detection of a NLRX1 expression product in a sample, the kit comprising at least a first NLRX1-specific reagent as described herein which specifically binds the NLRX1 expression product, on a solid support and comprising a detectable label. The kits described herein include reagents and/or components that permit assaying the level of an expression product in a sample obtained from a subject (e.g., a biological sample obtained from a subject). The kits described herein can optionally comprise additional components useful for performing the methods and assays described herein.

A kit can further comprise devices and/or reagents for concentrating an expression product (e.g, a polypeptide) in a sample, e.g. a plasma sample. Thus, ultrafiltration devices permitting, e.g., protein concentration from plasma can also be included as a kit component.

Preferably, a diagnostic or prognostic kit for use with the methods and assays disclosed herein contains detection reagents for NLRX1 expression products. Such detection reagents comprise in addition to NLRX1-specific reagents, for example, buffer solutions, labels or washing liquids etc. Furthermore, the kit can comprise an amount of a known nucleic acid and/or polypeptide, which can be used for a calibration of the kit or as an internal control. A diagnostic kit for the detection of an expression product can also comprise accessory ingredients like secondary affinity ligands, e.g., secondary antibodies, detection dyes and any other suitable compound or liquid necessary for the performance of a expression product detection method known to the person skilled in the art. Such ingredients are known to the person skilled in the art and may vary depending on the detection method carried out. Additionally, the kit may comprise an instruction leaflet and/or may provide information as to the relevance of the obtained results.

In some aspects, the invention described herein is directed to systems (and computer readable media for causing computer systems) for obtaining data from at least one sample obtained from at least one subject, the system comprising 1) a measuring module configured to receive the at least one sample and perform at least one analysis on the at least one sample to determine the level and/or activity of NLRX1 in the sample; 2) a storage device configured to store data output from the determination module; and 3) a display module for displaying a content based in part on the data output from the determination module, wherein the content comprises a signal indicative of the level and/or activity of NRLX1.

Figure 17:
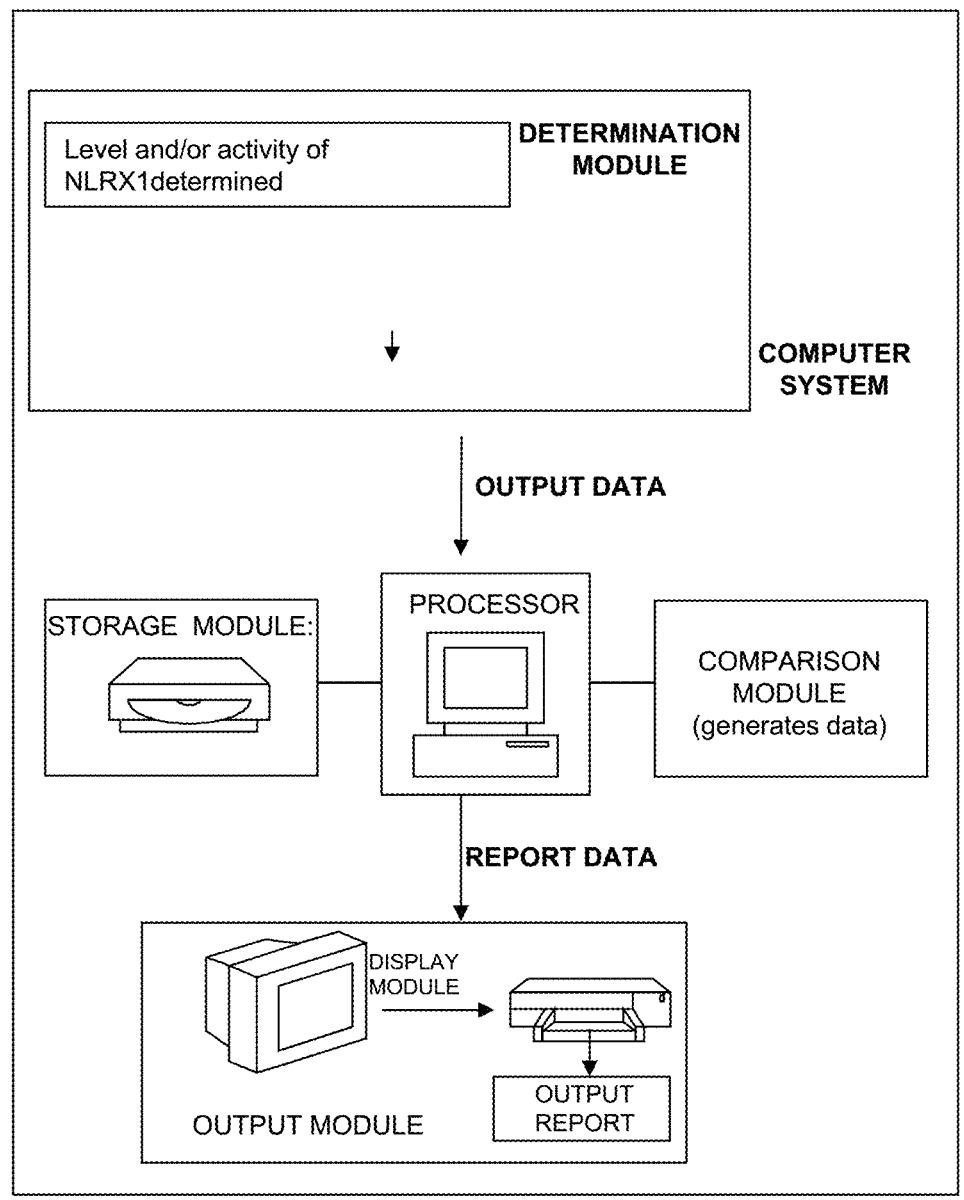
FIG. 17 is a diagram of an exemplary embodiment of a system for performing an assay for determining the level of NLRX1 in a sample obtained from a subject.

In one embodiment, provided herein is a system comprising: (a) at least one memory containing at least one computer program adapted to control the operation of the computer system to implement a method that includes a measuring module configured to measure the level of NLRX1 in a test sample obtained from a subject; a storage module configured to store output data from the determination module; a comparison module adapted to compare the data stored on the storage module with a reference level, and to provide a retrieved content, and a display module for displaying whether the sample comprises a level of NRLX1 which is significantly decreases relative to the reference expression level and/or displaying the relative level of NRLX1 and (b) at least one processor for executing the computer program (see FIG. 17).

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; a tablet; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip. The term a "computer system" may refer to a system having a computer, where the computer comprises a computer-readable medium embodying software to operate the computer. The term "software" is used interchangeably herein with "program" and refers to prescribed rules to operate a computer. Examples of software include: software; code segments; instructions; computer programs; and programmed logic.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The functional modules of certain embodiments of the invention include at minimum a measuring module, a storage module, a computing module, and a display module. The functional modules can be executed on one, or multiple, computers, or by using one, or multiple, computer networks. The measuring module has computer executable instructions to provide e.g., levels of expression products etc in computer readable form.

The measuring module can comprise any system for detecting a signal elicited from an assay to determine the level and/or activity of NLRX1 described above herein. In some embodiments, such systems can include an instrument, e.g., AU2700 (Beckman Coulter Brea, Calif.) as described herein for quantitative measurement of polypeptides or e.g., a real time PCR machine, e.g. a LIGHTCYCLER™ (Roche). In some embodiments, the measuring module can measure the intensity of a detectable signal from an assay indicating the level of NLRX1 polypeptide in the test sample. In some embodiments, the assay can be an immunoassay. In some embodiments, the measuring module can measure the intensity of a detectable signal from a RT-PCR assay indicating the level of NLRX1 RNA transcript in the test sample.

The information determined in the determination system can be read by the storage module. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon, for example, sample name, biomolecule assayed and the level of said biomolecule. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In some embodiments of any of the systems described herein, the storage module stores the output data from the determination module. In additional embodiments, the storage module stores reference information such as levels of NLRX1 in healthy subjects and/or a population of healthy subjects.

Figure 18:
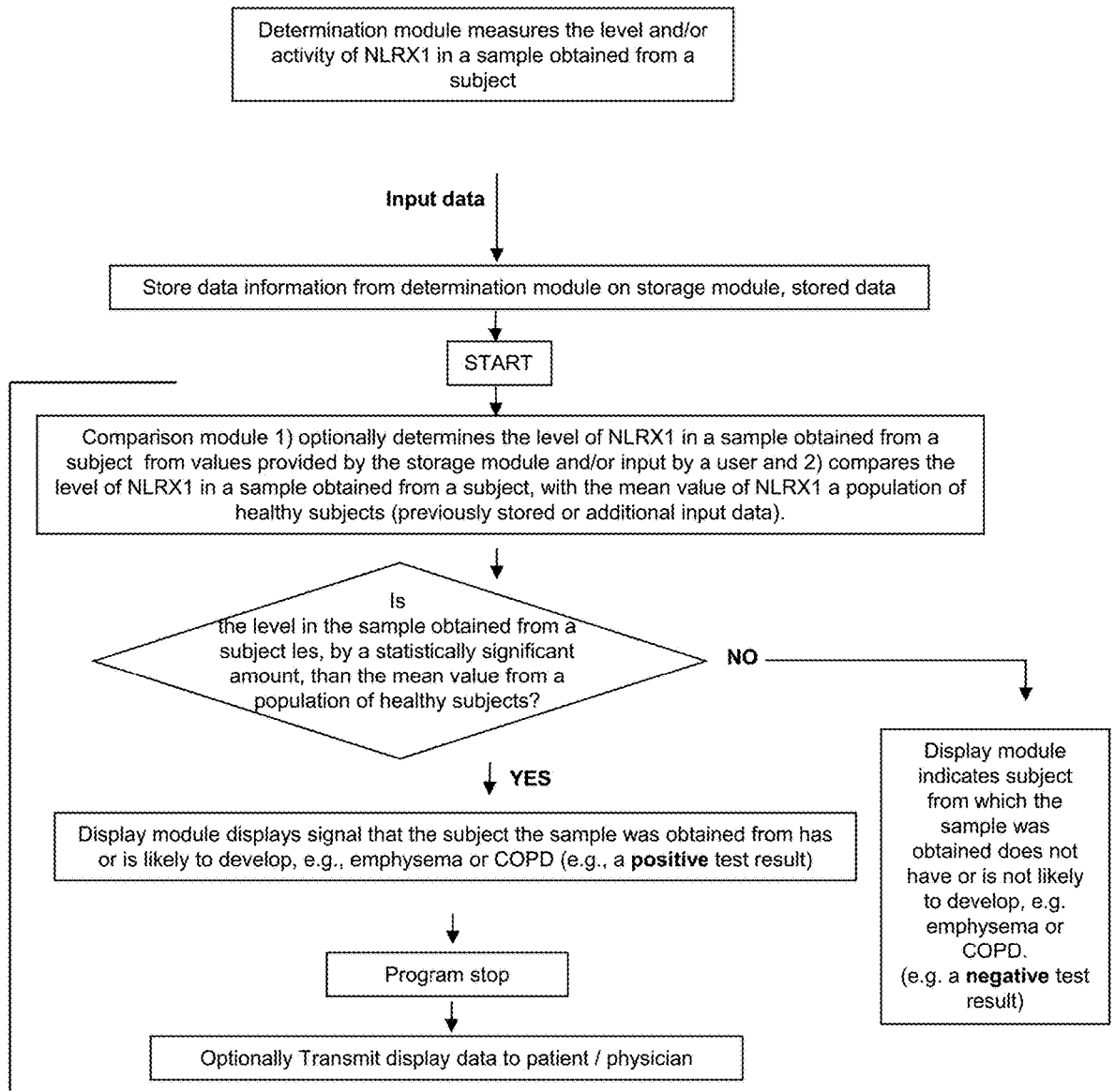
FIG. 18 is a diagram of an exemplary embodiment of a comparison module as described herein.

The "computing module" can use a variety of available software programs and formats for computing the level of NLRX1. Such algorithms are well established in the art. A skilled artisan is readily able to determine the appropriate algorithms based on the size and quality of the sample and type of data. The data analysis tools and equations described herein can be implemented in the computing module of the invention. In one embodiment, the computing module further comprises a comparison module, which compares the level of NLRX1 in a sample obtained from a subject as described herein with the mean value of NLRX1 in a population of healthy subjects (FIG. 18). By way of an example, when the value of NLRX1 in a sample obtained from a subject is measured, a comparison module can compare or match the output data with the mean value of NLRX1 in a population of healthy subjects. In certain embodiments, the mean value of NLRX1 in a population of healthy subjects can be pre-stored in the storage module. In various embodiments, the comparison module can be configured using existing commercially-available or freely-available software for comparison purpose, and may be optimized for particular data comparisons that are conducted.

Figure 19:
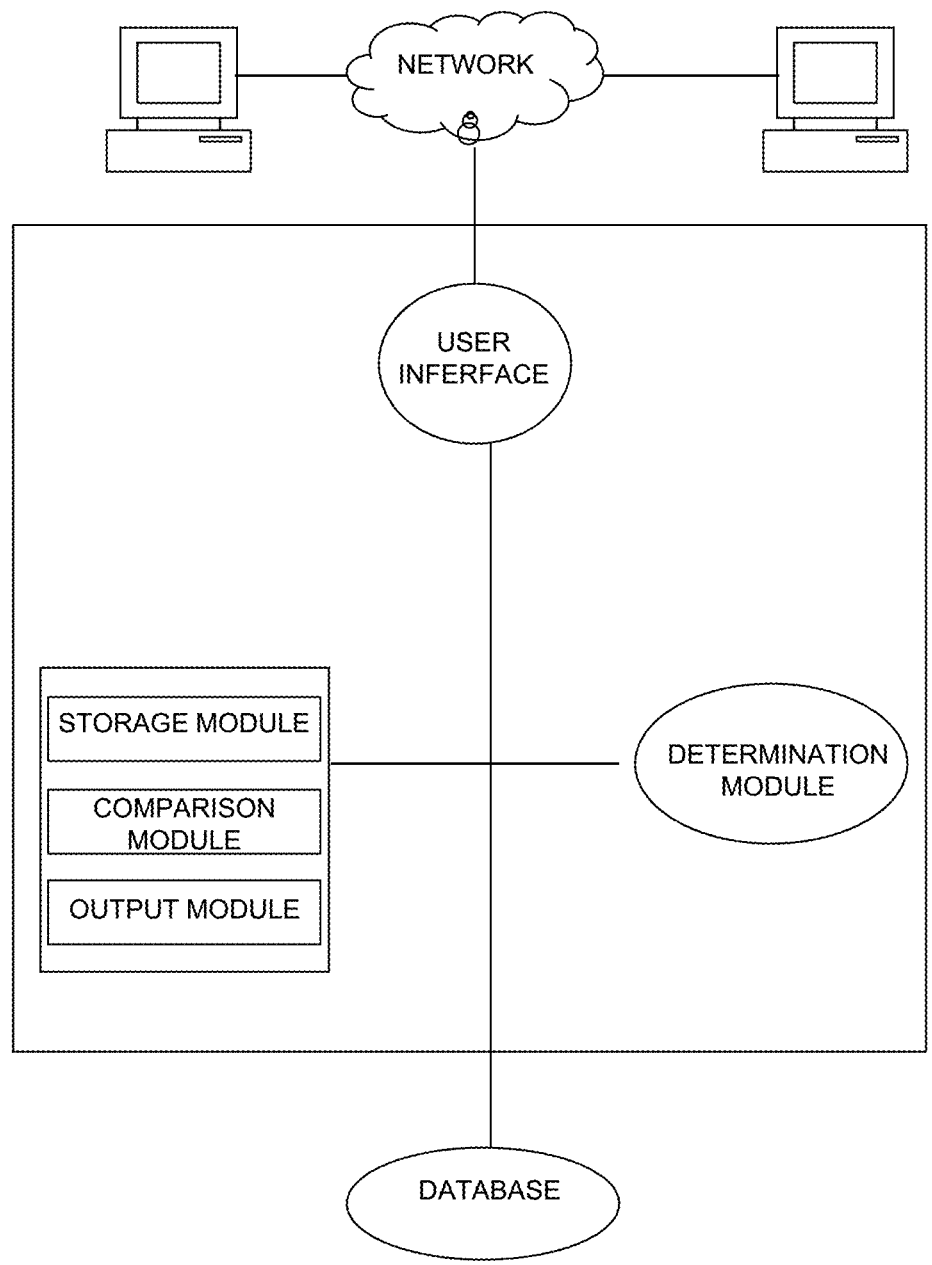
FIG. 19 is a diagram of an exemplary embodiment of an operating system and applications for a computing system as described herein.

The computing and/or comparison module, or any other module of the invention, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). In some embodiments users can directly access data (via Hypertext links for example) residing on Internet databases using a HTML interface provided by Web browsers and Web servers (FIG. 19).

The computing and/or comparison module provides a computer readable comparison result that can be processed in computer readable form by predefined criteria, or criteria defined by a user, to provide content based in part on the comparison result that may be stored and output as requested by a user using an output module, e.g., a display module.

In some embodiments, the content displayed on the display module can be the level of NLRX1 in the sample obtained from a subject. In some embodiments, the content displayed on the display module can be the relative level of NLRX1 in the sample obtained from a subject as compared to the mean level of NRLX1 in a population of healthy subjects. In some embodiments, if the computing module determines that the level of NRLX1 in the test sample obtained from a subject is less by a statistically significant amount than the reference level, the display module displays a signal indicating that the levels in the sample obtained from a subject are less than those of the reference level. In some embodiments, the signal indicates the subject is in need of treatment for COPD, emphysema, and/or cigarette smoke-induced lung damage. In some embodiments, the signal indicates the degree to which the level of NRLX1 in the sample obtained from a subject varies from the reference level. In some embodiments, the content displayed on the display module can indicate whether the subject has an increased likelihood of having or developing COPD, emphysema, and/or cigarette smoke-induced lung damage. In some embodiments, the content displayed on the display module can be a numerical value indicating one of these risks or probabilities. In such embodiments, the probability can be expressed in percentages or a fraction. For example, higher percentage or a fraction closer to 1 indicates a higher likelihood of a subject having or developing COPD, emphysema, and/or cigarette smoke-induced lung damage. In some embodiments, the content displayed on the display module can be single word or phrases to qualitatively indicate a risk or probability. For example, a word "unlikely" can be used to indicate a lower risk for having or developing COPD, emphysema, and/or cigarette smoke-induced lung damage, while "likely" can be used to indicate a high risk for having or developing COPD, emphysema, and/or cigarette smoke-induced lung damage.

In one embodiment of the invention, the content based on the computing and/or comparison result is displayed on a computer monitor. In one embodiment of the invention, the content based on the computing and/or comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the computing/comparison result. It should be understood that other modules of the invention can be adapted to have a web browser interface. Through the Web browser, a user can construct requests for retrieving data from the computing/comparison module. Thus, the user will typically point and click to user interface elements such as buttons, pull down menus, scroll bars and the like conventionally employed in graphical user interfaces.

Systems and computer readable media described herein are merely illustrative embodiments of the invention for determining the level and/or activity of NLRX1 in a sample obtained from a subject, and therefore are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of COPD, emphysema, and/or cigarette smoke-induced lung damage. A subject can be male or female.

As used herein, "engineered" refers to the aspect of having been manipulated by the hand of man. For example, a NLRX1 polypeptide is considered to be "engineered" when the sequence of the polypeptide and/or encoding nucleic acid sequence manipulated by the hand of man to differ from the sequence of an polypeptide as it exists in nature. As is common practice and is understood by those in the art, progeny and copies of an engineered polynucleotide and/or polypeptide are typically still referred to as "engineered" even though the actual manipulation was performed on a prior entity.

As used herein, "recombinant" refers to a cell, tissue or organism that has undergone transformation with a new combination of genes or DNA. When used in reference to nucleic acid molecules, "recombinant" refers to a combination of nucleic acid molecules that are joined together using recombinant DNA technology into a progeny nucleic acid molecule, and/or a heterologous nucleic acid sequence introduced into a cell, tissue, or organism. When used in reference to a polypeptide, "recombinant" refers to a polypeptide which is the expression product of a recombinant nucleic acid, and can be such a polypeptide as produced by a recombinant cell, tissue, or organisms. The nucleic acid molecule can be stably integrated into the genome of the host or the nucleic acid molecule can also be present as an extrachromosomal molecule. Such an extrachromosomal molecule can be auto-replicating. Recombinant viruses, cells, and organisms are understood to encompass not only the end product of a transformation process, but also recombinant progeny thereof.

A subject can be one who has been previously diagnosed with or identified as suffering from or having a condition in need of treatment (e.g. COPD, emphysema, and/or cigarette smoke-induced lung damage) or one or more complications related to such a condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, a particular "polypeptide", e.g. a NLRX1 polypeptide can include the human polypeptide (e.g., SEQ ID NO: 2); as well as homologs from other species, including but not limited to bovine, dog, cat chicken, murine, rat, porcine, ovine, turkey, horse, fish, baboon and other primates. The terms also refer to fragments or variants of the native polypeptide that maintain at least 50% of the activity or effect of the native full length polypeptide, e.g. as measured in an appropriate animal model. Conservative substitution variants that maintain the activity of wildtype polypeptides will include a conservative substitution as defined herein. The identification of amino acids most likely to be tolerant of conservative substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants can be tested for activity, for example, by administering the variant to an appropriate animal model of allograft rejection as described herein.

In some embodiments, a polypeptide, e.g., a NLRx1 polypeptide, can be a variant of a sequence described herein, e.g. a variant of a NLRX1 polypeptide comprising the amino acid sequence of SEQ ID NO: 2. In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, e.g., at least 50% of the wildtype reference protein. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or note, has more than 100% of the activity of wildtype, e.g. 110%, 125%, 150%, 175%, 200%, 500%, 1000% or more.

One method of identifying amino acid residues which can be substituted is to align, for example, the human polypeptide to a homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence, e.g. SEQ ID NOs: 2 or 4 or a nucleic acid encoding one of those amino acid sequences. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp (available on the world wide), with default parameters set.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure. Typically conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments, a polypeptide, e.g., a NLRX1 polypeptide, administered to a subject can comprise one or more amino acid substitutions or modifications. In some embodiments, the substitutions and/or modifications can prevent or reduce proteolytic degradation and/or prolong half-life of the polypeptide in the subject. In some embodiments, a polypeptide can be modified by conjugating or fusing it to other polypeptide or polypeptide domains such as, by way of non-limiting example, transferrin (WO06096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a polypeptide, e.g., an NLRX1 polypeptide, as described herein can comprise at least one peptide bond replacement. A single peptide bond or multiple peptide bonds, e.g. 2 bonds, 3 bonds, 4 bonds, 5 bonds, or 6 or more bonds, or all the peptide bonds can be replaced. An isolated peptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, a polypeptide, e.g., a NLRX1 polypeptide, as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, an NLRX1 polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a polypeptide, e.g. a NLRX1 polypeptide, can be modified, e.g. by addition of a moiety to one or more of the amino acids comprising the peptide. In some embodiments, a polypeptide as described herein can comprise one or more moiety molecules, e.g. 1 or more moiety molecules per peptide, 2 or more moiety molecules per peptide, 5 or more moiety molecules per peptide, 10 or more moiety molecules per peptide or more moiety molecules per peptide. In some embodiments, a polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties. The half-life of a polypeptide can be increased by the addition of moieties, e.g. PEG or albumin.

In some embodiments, the polypeptide administered to the subject (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. In some embodiments, a polypeptide as described herein can be chemically synthesized and mutations can be incorporated as part of the chemical synthesis process.

In some embodiments, a polypeptide, e.g., a NLRX1 polypeptide, as described herein can be formulated as a pharmaceutically acceptable prodrug. As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of β-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnej ad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", *Arfv. Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.,* 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.,* 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs,* [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", Adv. Drug Delivery Rev. 39(1-3): 117-151 (1999); Taylor, "Improved passive oral drug delivery via prodrugs", Adv. Drug Delivery Rev., 19(2): 131-148 (1996); Valentino and Borchardt, "Prodrug strategies to enhance the intestinal absorption of peptides", Drug Discovery Today 2(4): 148-155 (1997); Wiebe and Knaus, "Concepts for the design of anti-HIV nucleoside prodrugs for treating cephalic HIV infection", Adv. Drug Delivery Rev.: 39(1-3):63-80 (1999); Waller et al., "Prodrugs", Br. J. Clin. Pharmac. 28: 497-507 (1989), which are incorporated by reference herein in their entireties.

In some embodiments, a polypeptide as described herein can be a pharmaceutically acceptable solvate. The term "solvate" refers to a peptide as described herein in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The peptides of the present invention can be synthesized by using well known methods including recombinant methods and chemical synthesis. Recombinant methods of producing a peptide through the introduction of a vector including nucleic acid encoding the peptide into a suitable host cell is well known in the art, such as is described in Sambrook et al., Molecular Cloning: A Laboratory Manual, 2d Ed, Vols 1 to 8, Cold Spring Harbor, N.Y. (1989); M. W. Pennington and B. M. Dunn, Methods in Molecular Biology: Peptide Synthesis Protocols, Vol 35, Humana Press, Totawa, N.J. (1994), contents of both of which are herein incorporated by reference. Peptides can also be chemically synthesized using methods well known in the art. See for example, Merrifield et al., J. Am. Chem. Soc. 85:2149 (1964); Bodanszky, M., Principles of Peptide Synthesis, Springer-Verlag, New York, N.Y. (1984); Kimmerlin, T. and Seebach, D. J. Pept. Res. 65:229-260 (2005); Nilsson et al., Annu. Rev. Biophys. Biomol. Struct. (2005) 34:91-118; W. C. Chan and P. D. White (Eds.) Fmoc Solid Phase Peptide Synthesis: A Practical Approach, Oxford University Press, Cary, N.C. (2000); N. L. Benoiton, Chemistry of Peptide Synthesis, CRC Press, Boca Raton, Fla. (2005); J. Jones, Amino Acid and Peptide Synthesis, $2^{nd}$ Ed, Oxford University Press, Cary, N.C. (2002); and P. Lloyd-Williams, F. Albericio, and E. Giralt, Chemical Approaches to the synthesis of peptides and proteins, CRC Press, Boca Raton, Fla. (1997), contents of all of which are herein incorporated by reference. Peptide derivatives can also be prepared as described in U.S. Pat. Nos. 4,612,302; 4,853,371; and 4,684,620, and U.S. Pat. App. Pub. No. 2009/0263843, contents of all which are herein incorporated by reference.

In some embodiments, the technology described herein relates to a nucleic acid encoding a polypeptide (e.g. a NLRX1 polypeptide) as described herein. As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the nucleic acid is DNA. In another aspect, the nucleic acid is RNA. Suitable nucleic acid molecules are DNA, including genomic DNA or cDNA. Other suitable nucleic acid molecules are RNA, including mRNA. The nucleic acid molecule can be naturally occurring, as in genomic DNA, or it may be synthetic, i.e., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

In some embodiments, a nucleic acid encoding a polypeptide as described herein (e.g. an NLRX1 polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding encoding a polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In some embodiments, an inhibitor of a given polypeptide can be an antibody reagent specific for that polypeptide. As used herein an "antibody" refers to IgG, IgM, IgA, IgD or IgE molecules or antigen-specific antibody fragments thereof (including, but not limited to, a Fab, F(ab')2, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to e.g., NLRX1 or MAVS.

As used herein, "expression level" refers to the number of mRNA molecules and/or polypeptide molecules encoded by a given gene that are present in a cell or sample. Expression levels can be increased or decreased relative to a reference level.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. COPD, emphysema, and/or cigarette smoke-induced lung damage. The term "treating" includes reducing or alleviating at least one adverse effect or symptom of a condition, disease or disorder associated with a condition. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); The ELISA guidebook (Methods in molecular biology 149) by Crowther J. R. (2000); Fundamentals of RIA and Other Ligand Assays by Jeffrey Travis, 1979, Scientific Newsletters; Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating COPD in a subject in need thereof, the method comprising administering an inhibitor of MAVS.
2. A method of treating cigarette smoke-induced lung damage in a subject in need thereof, the method comprising administering an inhibitor of MAVS.
3. The method of paragraph 2, wherein the cigarette smoke-induced lung damage is selected from the group consisting of:
    inflammation; alveolar destruction; protease induction; structural cell apoptosis; and inflammasome activation.
4. A method of treating emphysema in a subject in need thereof, the method comprising administering an inhibitor of MAVS.
5. The method of paragraph 4, wherein the emphysema is cigarette smoke induced emphysema.
6. The method of any of paragraphs 1-5, wherein the inhibitor of MAVS is an agonist of NLRX1.
7. The method of any of paragraphs 1-5, wherein the inhibitor of MAVS is a modulator of NLRX1-dependent pathways.
8. The method of paragraph 6, wherein the agonist of NLRX1 is a nucleic acid encoding NLRX1 or an NLRX1 polypeptide.
9. A method of treating COPD in a subject in need thereof, the method comprising administering an agonist of NLRX1.
10. A method of treating cigarette smoke-induced lung damage in a subject in need thereof, the method comprising administering an agonist of NLRX1.
11. The method of paragraph 10, wherein the cigarette smoke-induced lung damage is selected from the group consisting of:
    inflammation; alveolar destruction; protease induction; structural cell apoptosis; and inflammasome activation.
12. A method of treating emphysema in a subject in need thereof, the method comprising administering an agonist of NLRX1.
13. The method of paragraph 12, wherein the emphysema is cigarette smoke induced emphysema.
14. The method of any of paragraphs 1-13, wherein the subject is a subject determined to have a decreased level of NLRX1 expression.
15. An assay comprising:
    measuring the level of NLRX1 in a test sample obtained from a subject;
    wherein an decrease in the expression level relative to a reference level indicates the subject has a higher risk of having or developing COPD, emphysema, and/or cigarette-induced lung damage.
16. A method of identifying a subject in need of treatment for COPD, emphysema, and/or cigarette-induced lung damage, the method comprising:
    measuring the level of NLRX1 in a test sample obtained from a subject; and
    identifying the subject as being in need of treatment for COPD, emphysema, and/or cigarette-induced lung damage when the expression level of NLRX1 is decreased relative to a reference level.
17. A method of determining if a subject is at risk for COPD, emphysema, and/or cigarette-induced lung damage, the method comprising:
    measuring the level of NLRX1 in a test sample obtained from a subject;
    comparing the level of NLRX1 in the sample to a reference level of NLRX1;
    determining that the subject is at risk for COPD, emphysema, and/or cigarette-induced lung damage when the level of NLRX1 is decreased relative to a reference level; and
    determining that the subject is not at risk for COPD, emphysema, and/or cigarette-induced lung damage when the level of NLRX1 is not decreased relative to a reference level.
18. A method of determining the efficacy of a treatment for COPD, emphysema, and/or cigarette-induced lung damage, the method comprising:
    (a) measuring the level of NLRX1 in a test sample obtained from a subject before administration of the treatment;
    (b) measuring the level of NLRX1 in a test sample obtained from a subject after administration of the treatment;
    (c) determining that the treatment is efficacious when the expression level determined in step (b) is not decreased relative to the expression level determined in step (a); and
    (d) determining that the treatment is not efficacious when the expression level determined in step (b) is decreased relative to the expression level determined in step (a).
19. A method of treatment for COPD, emphysema, and/or cigarette-induced lung damage comprising;
    measuring the level of NLRX1 in a test sample obtained from a subject;
    treating the subject when the level of NLRX1 is decreased relative to a reference level.
20. A method of treatment for COPD, emphysema, and/or cigarette-induced lung damage comprising;
    treating a subject determined to have a level of NLRX1 which is decreased relative to a reference level.
21. The method of any of paragraphs 19-20, wherein the treatment comprises a treatment selected from the group consisting of:
    administration of a bronchodilator; administration of an inhaled steroid; administration of oxygen therapy; bullectomy; lung volume reduction surgery; smoking cessation; lung transplant; administration of an inhibitor of MAVS; administration of an agonist of NLRX1; administration of a nucleic acid encoding NLRX1; and administration of a NLRX1 polypeptide.
22. The assay/method of any of paragraphs 15-21, wherein the level of NLRX1 is determined by measuring the level of a nucleic acid.
23. The assay/method of paragraph 22, wherein the level of NLRX1 is determined by measuring the level of NLRX1 RNA transcript.
24. The assay/method of any of paragraphs 22-23, wherein the level of the nucleic acid is determined using a method selected from the group consisting of:

RT-PCR; quantitative RT-PCR; Northern blot; microarray based expression analysis; next-generation sequencing; and RNA in situ hybridization.
25. The assay/method of any of paragraphs 15-24, wherein the level of NLRX1 is determined by measuring the level of NLRX1 polypeptide.
26. The assay/method of paragraph 25, wherein the level of the polypeptide is determined using a method selected from the group consisting of:
    Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay.
27. The assay/method of any of paragraphs 25-26, wherein the polypeptide level is measured using immunochemistry.
28. The assay of paragraph 27, wherein the antibody reagent is detectably labeled or generates a detectable signal.
29. The assay/method of any of paragraphs 15-28, wherein the expression level of NLRX1 is normalized relative to the expression level of one or more reference genes or reference proteins.
30. The assay/method of any of paragraphs 15-29, wherein the reference level of NLRX1 is the expression level of NLRX1 in a prior sample obtained from the subject.
31. The assay/method of any of paragraphs 15-30, wherein the subject is a subject with a history of smoking.
32. The assay/method of any of paragraphs 15-31, wherein the sample is selected from the group consisting of:
    a lung biopsy; bronchoalveolar lavage (BAL); sputum; induced sputum; blood; plasma; and serum.
33. The assay/method of any of paragraphs 15-32, further comprising the step of treating the subject with a treatment selected from the group consisting of:
    administration of a bronchodilator; administration of an inhaled steroid; administration of oxygen therapy; bullectomy; lung volume reduction surgery; smoking cessation; lung transplant; administration of an inhibitor of MAVS; administration of an agonist of NLRX1; administration of a nucleic acid encoding NLRX1; and administration of a NLRX1 polypeptide.
34. A kit for performing the method/assay of any of paragraphs 15-33.
35. The use of an inhibitor of MAVS for treating COPD, emphysema, or cigarette-induced lung damage in a subject in need thereof, the use comprising administering an inhibitor of MAVS to the subject.
36. The use of paragraph 35, wherein the cigarette smoke-induced lung damage is selected from the group consisting of:
    inflammation; alveolar destruction; protease induction; structural cell apoptosis; and inflammasome activation.
37. The use of paragraph 35, wherein the emphysema is cigarette smoke induced emphysema.
38. The use of any of paragraphs 35-37, wherein the inhibitor of MAVS is an agonist of NLRX1.
39. The use of any of paragraphs 35-38, wherein the inhibitor of MAVS is a modulator of NLRX1-dependent pathways.
40. The method of paragraph 38, wherein the agonist of NLRX1 is a nucleic acid encoding NLRX1 or an NLRX1 polypeptide.
41. The use of an inhibitor of MAVS for treating COPD, emphysema, or cigarette-induced lung damage in a subject in need thereof, the use comprising administering an agonist of NLRX1 to the subject.
42. The use of paragraph 41, wherein the cigarette smoke-induced lung damage is selected from the group consisting of:
    inflammation; alveolar destruction; protease induction; structural cell apoptosis; and inflammasome activation.
43. The use of paragraph 41, wherein the emphysema is cigarette smoke induced emphysema.
44. The method of any of paragraphs 41-43, wherein the agonist of NLRX1 is a nucleic acid encoding NLRX1 or an NLRX1 polypeptide.

EXAMPLES

Example 1: Suppression of NLRX1 in Chronic Obstructive Pulmonary Disease

It is demonstrated herein that NLRX1 expression is significantly decreased in three COPD cohorts. This suppression correlated with disease severity and inversely with pulmonary function, quality of life and prognosis. CS inhibited murine NLRX1 and null mutations of NLRX1 augmented CS-induced inflammation, alveolar destruction, protease induction, structural cell apoptosis and inflammasome activation. In contrast, null mutations of MAVS abrogated this CS-induced inflammation and remodeling. Furthermore, restoration of NLRX1 ameliorated CS-induced alveolar destruction significantly. Thus, CS inhibits NLRX1 which facilitates CS-induced and MAVS-dependent inflammatory, remodeling, protease, cell death and inflammasome responses.

Cigarette smoke (CS) causes a broad spectrum of diseases characterized by inflammation and tissue remodeling including chronic obstructive pulmonary disease (COPD), cancer and atherosclerosis(1-3). In many of these disorders the inflammation is believed to drive disease pathogenesis. This can be seen in, COPD, the fourth leading cause of death in the world, where pulmonary inflammation is believed to be causally related to the emphysema and other pathologic alterations in the lungs from these patients(3-5).

CS regulates the inflammasome where it activates caspase 1 and IL-18(6, 7). IL-18 signaling also plays a key role in the pathogenesis of CS-induced inflammation and emphysema (6). However, the mechanism(s) that controls lung inflammasome activation at baseline and the alterations that CS induces to activate the inflammasome have not been defined.

Mitochondria are cellular powerhouses that generate ATP and participate in other critical responses including calcium homeostasis, cell signaling, apoptosis, and aging(8). Recent studies also demonstrated that mitochondria play a critical role in cellular innate antiviral immunity (reviewed in references 9, 10). Viral infections are well known to play important roles in the pathogenesis of CS-induced disorders such as COPD (11,12). CS and viruses/viral PAMPs interact to induce exaggerated pulmonary inflammatory and remodeling responses and that MAVS (mitochondrial antiviral signaling molecule) plays a critical role in this interaction (5). MAVS is exquisitely regulated by stimulators such as the RIG-like helicases that induce MAVS self-association and induce inflammation. Importantly, it is now known that MAVS is tonically inhibited in the quiescent non-infected state (reviewed in reference 13). In addition, the mitochondrial protein, nucleotide-binding, leucine-rich repeats (NLR) molecule X1 (NLRX1) has been reported to inhibit virus activation of MAVS (14-16).

It is hypothesized herein that mitochondria play a critical role in the pathogenesis of CS-induced responses in COPD. Specifically it was hypothesized that the tissue effects of CS are mediated by its ability to abrogate the effects of specific MAVS inhibitors and that NLRX1 is a critical target of this CS-induced dysinhibition. To test this hypothesis the expression of NLRX1 was evaluated in three cohorts of patients with COPD and the relationships between NLRX1 suppression and disease severity were characterized. In addition, the effects of CS on the expression of NLRX1 were evaluated and the roles of MAVS and NLRX1 in CS-induced murine pulmonary inflammation and alveolar remodeling responses were defined.

Results and Discussion

Figure 1B:
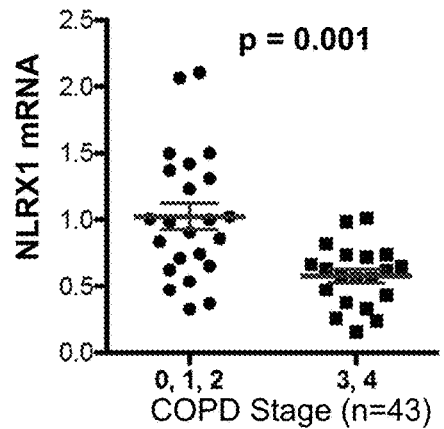
Figure 1C:
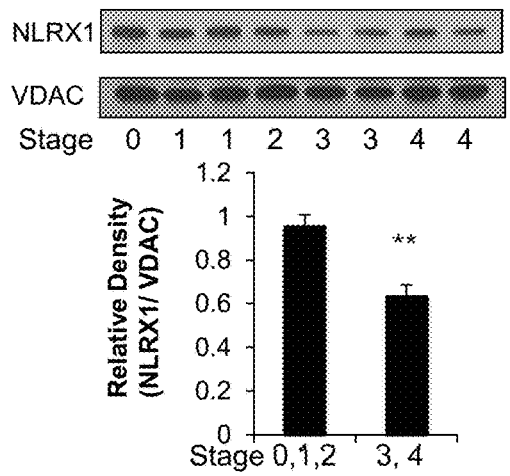
Figure 1D:
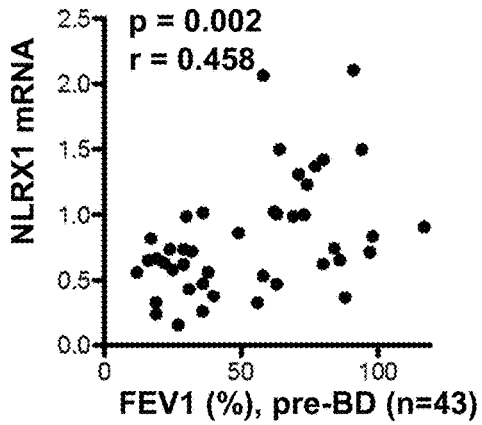
Figure 1E:
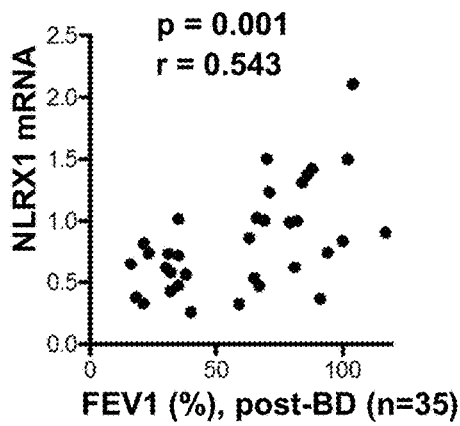
Figure 1F:
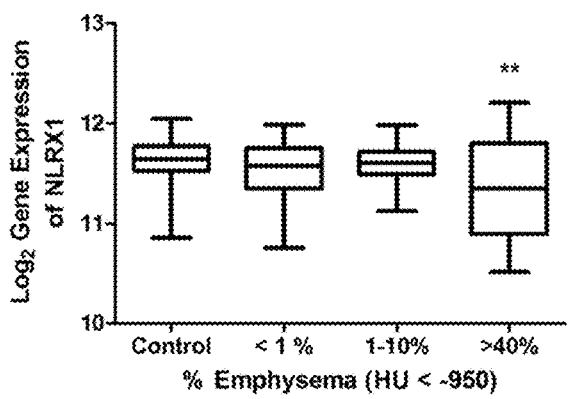
Figure 1G:
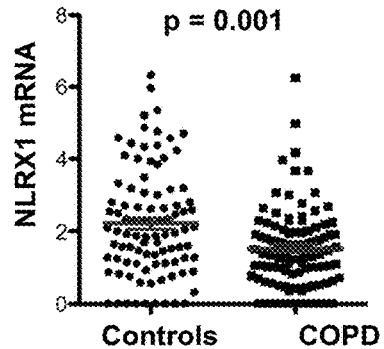
Figure 1H:
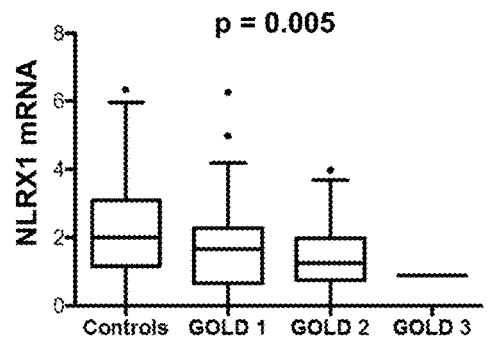
Figure 6:
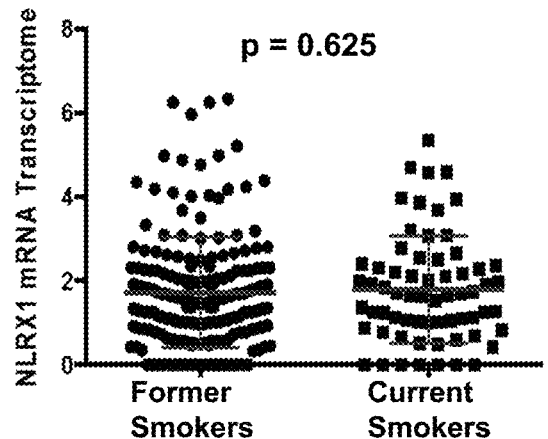
FIG. 6 demonstrates the levels of NLRX1 mRNA and the status of smoking history in the Korean Asan cohort.

First, mRNAs were extracted from fresh frozen lung tissues from the 7 controls and 36 patients with COPD in the NIH-sponsored Lung Tissue Research Consortium (LTRC) cohort. The latter contained 6, 10, 10 and 10 specimens from GOLD stage 1, 2, 3 and 4 individuals, respectively. The basic demographic characteristics of these patients are summarized in the Table 1. Interestingly, real-time RT-PCR analysis demonstrated that the levels of mRNA encoding NLRX1 were significantly decreased in patients with advanced stages of COPD (FIG. 1A-1B). In keeping with this observation, western blot evaluations of mitochondria-enriched protein fractions demonstrated that the expression of NLRX1 protein was significantly decreased in patients with advanced stages of COPD (FIG. 1C). In addition, NLRX1 expression correlated significantly with the patient's forced expiratory volume in one second ($FEV_1$; % predicted), an indicator of airflow limitation and a measure of COPD disease severity (FIG. 1D-1E). Interestingly, similar correlations were noted between NLRX1 suppression and pre- and post-bronchodilator $FEV_1$ suggesting that these relationships are not related to reversible airways obstruction (FIG. 1D-1E). In addition, similar suppression of NLRX1 was seen in a cohort of patients from the University of Pittsburgh which was most impressive in patients with severe emphysema (FIG. 1F). Because the LTRC and Pittsburgh cohorts did not contain large numbers of patients with mild-moderate disease a third cohort of Korean patients with mild-moderate disease (Asan cohort) was also studied (Table 1C). The studies of this Asan cohort demonstrated that, the expression of NLRX1 was also significantly decreased in patients with GOLD Stage 1 and 2 COPD where it correlated significantly with the patient's $FEV_1$ (%, predicted) (FIGS. 1G, 1H, 4A, 4B and 5). Almost all human samples were from former or current smokers in the three human cohorts (Table 1), preventing the evaluation of smoking effects on NLRX1 expression in these cohorts. There was no statistical difference of NLRX1 expression between former smokers vs. current smokers in all three human cohorts (FIG. 6 and data not shown). Finally, in all cases, these alterations were at least partially NLRX1-specific because the expression of related genes including RIG-I, MDA-5, MAVS, NLRP3 and caspases-1, -4 and -5 were not similarly altered (FIGS. 7A-7B and data not shown). These studies demonstrate that the levels of NLRX1 are selectively decreased in patients with COPD where this suppression correlates with clinical stage and parameters of disease severity.

Figure 9:
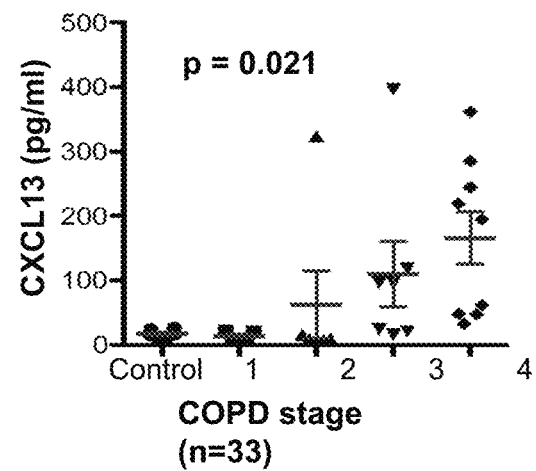
FIG. 9 demonstrates the levels of CXCL13 protein in LTRC samples plotted in controls (0) and in patients with COPD of varying severity (GOLD 1, 2, 3, and 4)
Figure 10A:
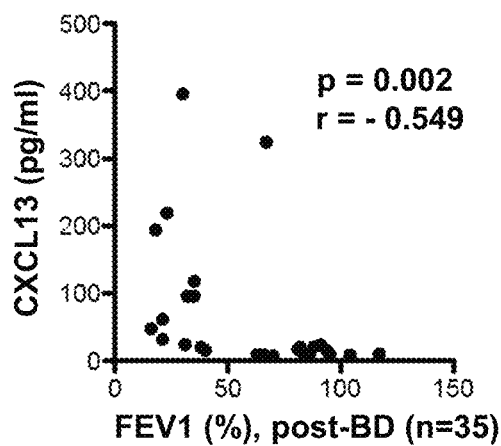
FIGS. 10A-10D demonstrate the correlations between the levels of CXCL13 protein and (FIG. 10A) post-bronchodilator $FEV_1$(% of predicted value), (FIG. 10B) NLRX1 mRNA, (FIG. 10C) BODE index, and (FIG. 10D) SGRQ score, respectively, in LTRC cohort.
Figure 10B:
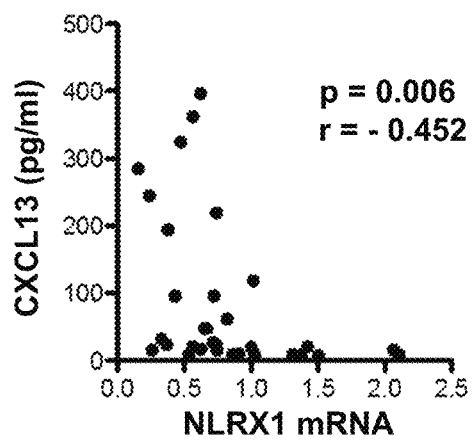
Figure 10C:
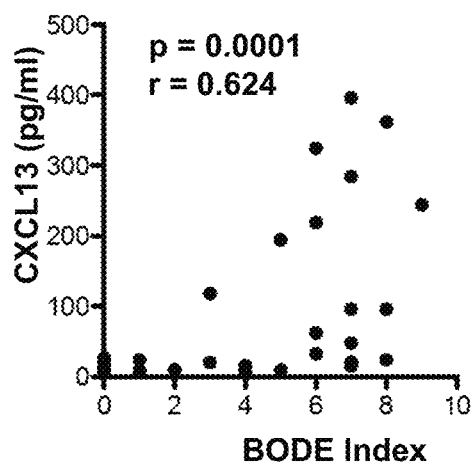
Figure 10D:
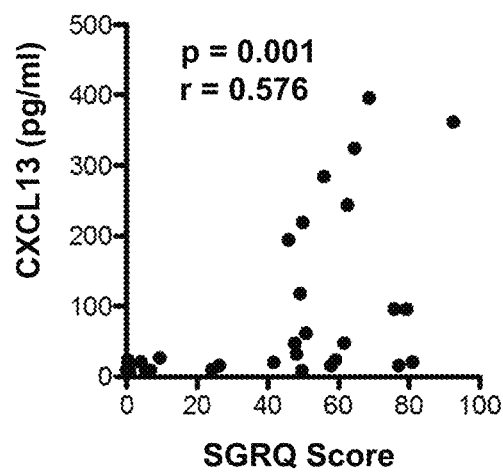

To further understand the clinical implications of these findings, the relationships between NLRX1 gene expression and clinical parameters of COPD were evaluated. These studies demonstrated that, in the LTRC cohort, the levels of NLRX1 gene expression also correlated with other measures of pulmonary function including diffusing capacity ($DL_{CO}$) and 6 minute-walking distance (FIGS. 8A-8C and data not shown). Importantly, the levels of NLRX1 mRNA also correlated inversely with the BODE index and scores on the St. George's Respiratory Questionnaire (SGRQ) (FIG. 8B and data not shown) which are predictors of disease mortality and quality of life respectively. The relationships between NLRX1 and dyspnea were also assessed using the BORG scale at rest and at the termination of exercise. Although the levels of NLRX1 did not correlate with the BORG scale at rest (data not shown) they did correlate with the BORG scale at exercise termination (FIG. 8C). Importantly, CXCL13, which is produced by lymphoid follicles in COPD(17) and inhibited via an NLRX1-dependent mechanism (see below) was significantly enhanced in patients with advanced stages of COPD where it correlated inversely with the expression of NLRX1 and also correlated with the patient's $FEV_1$ (%, predicted) and other clinical variables including $DL_{CO}$, the BODE index and SGRQ scores. (FIGS. 9 and 10A-10B and data not shown). These studies reinforce the relationships between the suppression of NLRX1 regulated pathways and abnormal pulmonary function and highlight the relationships between NLRX1 suppression and mortality, poor quality of life and exercise-induced dyspnea.

Figure 2A:
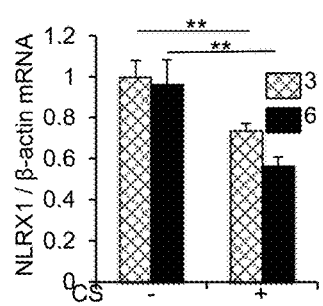
Figure 2B:
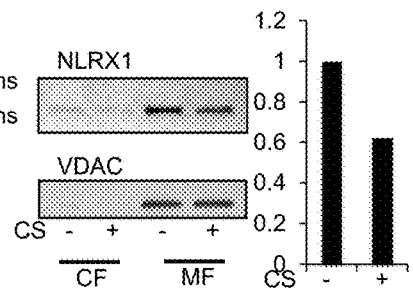
Figure 2C:
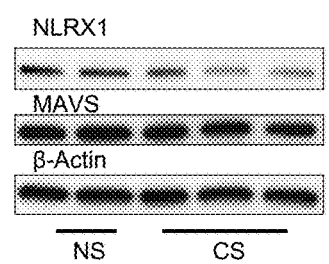
Figure 2D:
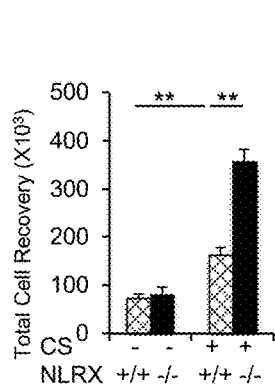
Figure 2E:
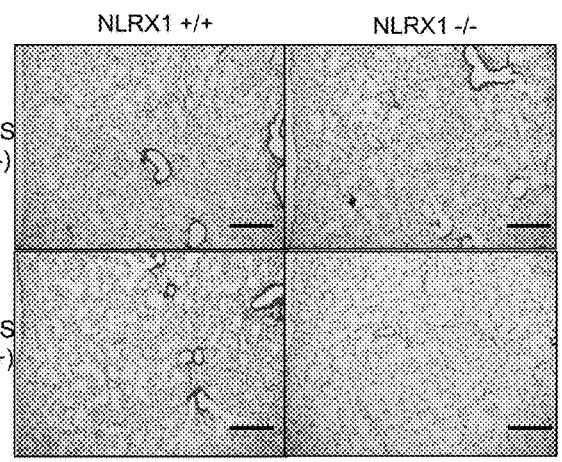
Figure 2F:
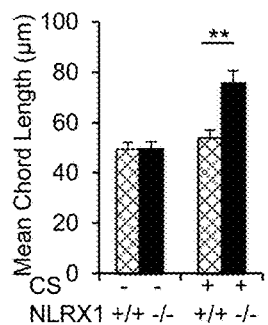
Figure 11A:
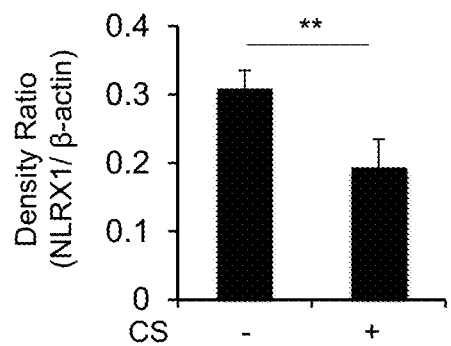
FIGS. 11A-11B demonstrate, from the Westernblot presented on FIG. 2C the densitometric evaluation of (FIG. 11A) NLRX1 expression and (FIG. 11B) MAVS expression, respectively, are demonstrated (** $p<0.01$).
Figure 11B:
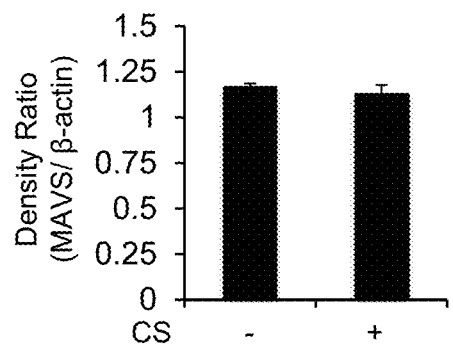
Figure 12:
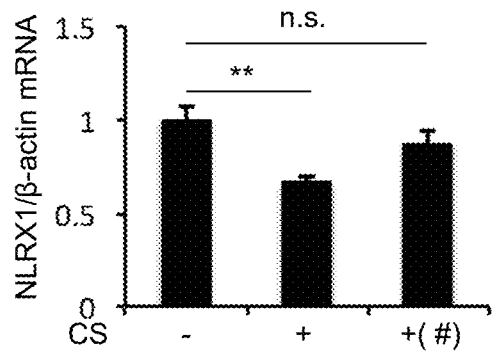
FIG. 12 demonstrates the suppression of NLRX1 mRNA accumulation in 3-month cigarette smoke-exposed lungs (CS+) and its recovery 3 months after the cessation of CS exposure (#) (** $p<0.01$).

To define the role(s) of NLRX1 in CS-induced responses, the effects of CS on NLRX1 expression in WT mice were characterized and the CS-induced tissue responses in WT and NLRX1 null mutant (−/−) animals were defined using previously described methodology (5, 6). NLRX1 mRNA and protein were readily appreciated in lungs and enriched mitochondria from WT mice (FIG. 2A-2B). Importantly the levels of pulmonary NLRX1 mRNA and NLRX1 protein were significantly decreased after CS exposure (FIG. 2A-2B). Immunohistochemical staining of NLRX1 protein revealed that NLRX1 expression was prominent in alveolar macrophages both in mice and humans (data not shown). Western blot analysis of NLRX1 protein in BAL cells from 3 month-CS-exposed lungs where alveolar macrophages consist of more than 95% of total BAL cells further confirmed that NLRX1 protein was significantly suppressed after CS exposure (FIGS. 2C and 11A). The expression of MAVS protein, however, was not significantly altered in BAL cells after CS exposure (FIGS. 2C and 11B). This suppression of NLRX1 was, at least partially, reversible because, NLRX1 gene expression returned to normal levels 3 months after the cessation of CS exposure (FIG. 12). In keeping with reported experiments using WT mice, modest BAL and alveolar inflammation and modest alveolar destruction could be appreciated after 3 and 6 months of CS-exposure respectively (6, 18). Importantly, these inflammatory and remodeling responses were markedly enhanced in lungs from CS-exposed NLRX1$^{−/−}$ mice which manifest enhanced BAL total cell, macrophage and neutrophil recovery (FIG. 2D and data not shown) and exaggerated emphysema that could be seen with histologic and morphometric assessments after only 3 months of CS exposure (FIGS. 2E and 2F and data not shown).

Figure 13:
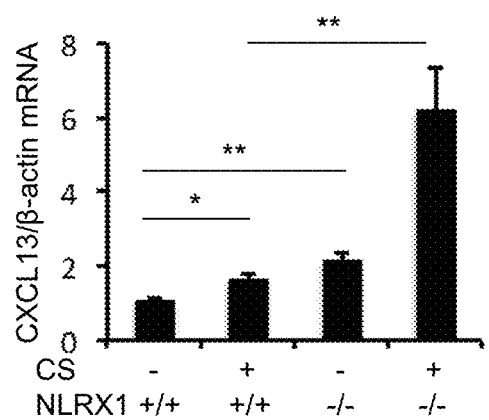
FIG. 13 demonstrates the enhancement of CXCL13 mRNA expression after 3-month cigarette smoke-exposure (CS+) in the lungs from NLRX1 deficient (NLRX1−/−) mice compared to those from WT controls (NLRX1+/+) (* $p<0.05$, ** $p<0.01$).
Figure 14:
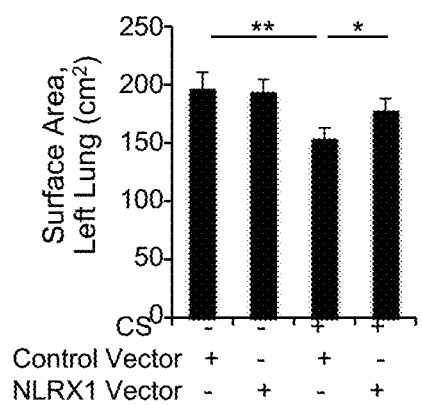
FIG. 14 demonstrates the restoration of CS-induced emphysematous alveolar destruction after NLRX1 gene overexpression in vivo. After 6-month-CS-exposure, morphometric evaluation of alveolar surface area was analyzed (* $p<0.05$, ** $p<0.01$).
Figure 15:
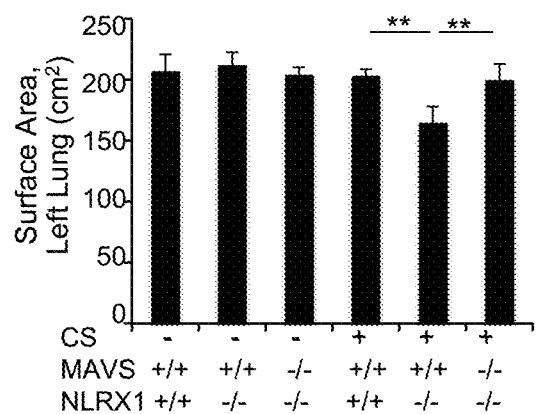
FIG. 15 depicts measurement of alveolar surface area after 3-month-CS-exposure in wild type (WT) controls, NLRX1$^{-/-}$ and NLRX1$^{-/-}$/MAVS$^{-/-}$ mice (** $p<0.01$).
Figure 16:
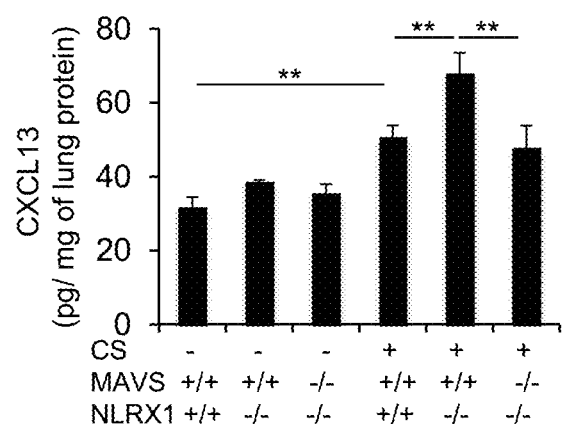
FIG. 16 demonstrates the enhancement of CXCL13 mRNA expression after 3-month cigarette smoke-exposure (CS+) in the lungs from NLRX1 deficient (NLRX1−/−) mice compared to those from WT controls (NLRX1+/+) (* $p<0.05$, ** $p<0.01$).

To further define the mechanisms by which NLRX1 suppression mediates CS-induced pulmonary inflammation and alveolar remodeling responses, the molecules/pathways that are believed to play important roles in the COPD pathogenesis were evaluated. In accord with the importance of protease anti-protease balance, cell death, viral infection and inflammasome activation in COPD pathogenesis (reviewed in references (3, 19-21)), CS induction of MMP-12 (FIG. 2G), cathepsins K and S (data not shown), type 1 IFNs (FIG. 2H), epithelial DNA injury and cell death (FIG. 2I) and caspase 1, IL-1β and IL-18 activation (FIG. 2J-2L) were enhanced in NLRX1 null mice compared to those from WT mice. Interestingly, CS exposure caused a modest increase in CXCL13 in the lungs of WT mice and this gene expression was synergistically upregulated in the lungs of NLRX1 deficient mice after 3 months of CS exposure (FIG. 13). Finally, studies were undertaken to determine if the NLRX1 supplementation could abrogate the phenotype in the CS exposed mice in vivo. In these experiments, a lentiviral gene delivery system was used to expose mice that had been given NLRX1 or controls to CS for 6 months. These experiments demonstrated that CS-induced emphysematous alveolar destruction was markedly decreased in lungs from NLRX1-overexpressed mice compared to those of controls (FIGS. 2M and 14). Taken together, these results indicate that NLRX1 is a critical inhibitor of CS-induced pulmonary inflammation and tissue remodeling responses, whose inhibitory functions are decreased in pulmonary tissues by chronic CS exposure.

Figure 3C:
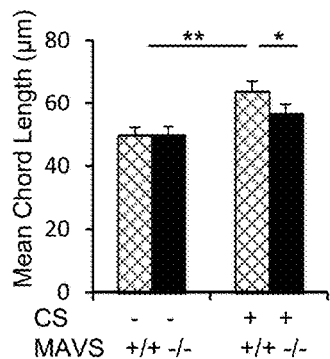
Figure 3D:
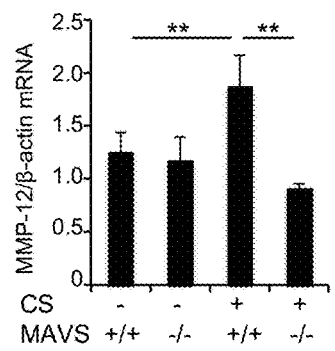
Figure 3E:
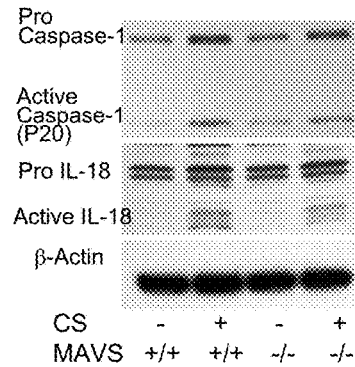
Figure 3F:
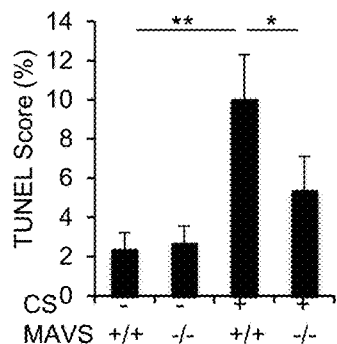
Figure 3G:
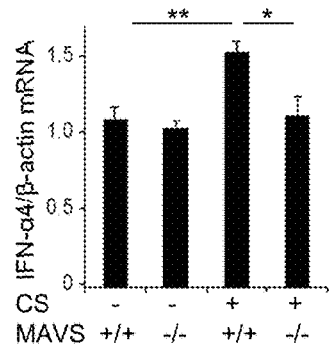
Figure 3H:
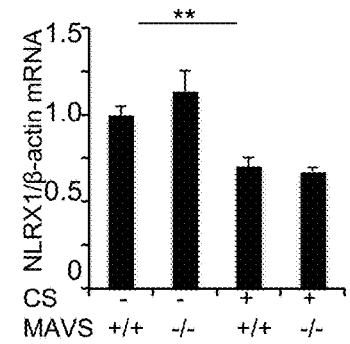
Figure 3I:
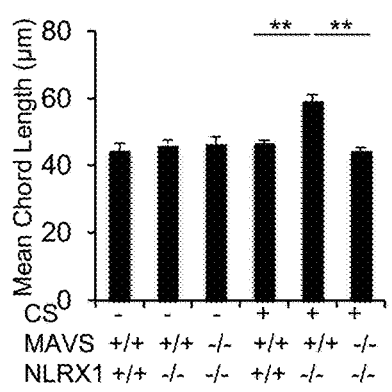
Figure 3J:
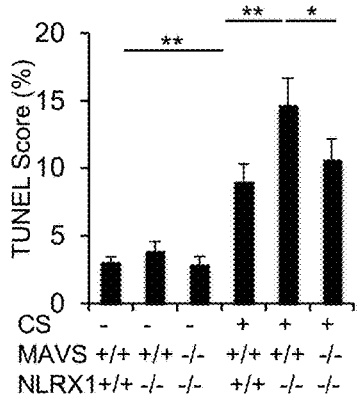
Figure 3K:
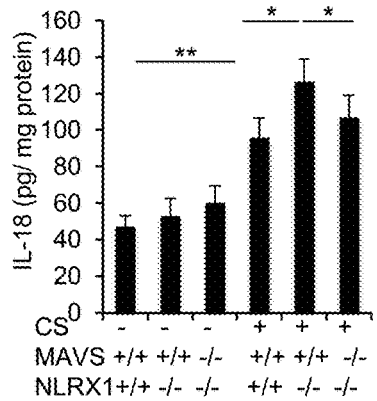
Figure 4A:
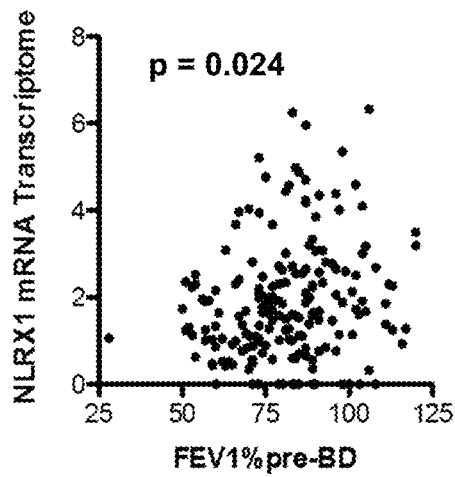
FIGS. 4A-4B demonstrate the correlations between the levels of (FIG. 4A) NLRX1 mRNA and pre-bronchodilator $FEV_1$(% of predicted value) and (FIG. 4B) NLRX1 mRNA and post-bronchodilator $FEV_1$(% of predicted value), respectively, in the Korean Asan cohort FIG. 5 demonstrates the statistical result of the comparison between each subgroup in Korean Asan cohort. Because only one patient was in the subgroup of GOLD3, no comparison was undertaken with the subgroup of GOLD 3 (* For the overall comparison between all subgroups, please see FIG. 1H).
Figure 4B:
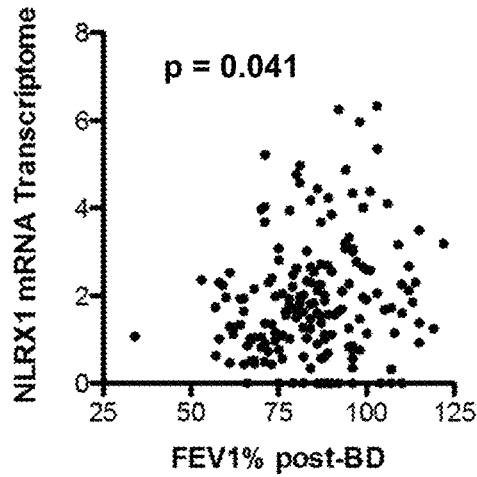
Figure 5:
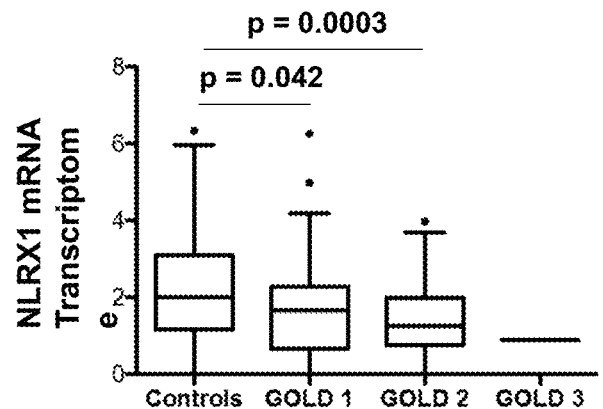

The studies noted above demonstrate that CS exposure decreases NLRX1 expression and NLRX1 has been reported to be an inhibitor of MAVS (14, 15). Thus studies were next undertaken to determine if mitochondria, in particular MAVS, plays an important effector role in CS-induced inflammation and remodeling. First, this was done by comparing the CS-induced responses in WT and MAVS$^{-/-}$ mice. These studies demonstrated that inflammation and alveolar destruction were significantly decreased in lungs from CS-exposed MAVS$^{-/-}$ mice compared to WT controls (FIG. 3A-3C). CS-induced protease responses, activation of caspase 1, IL-1β and IL-18, TUNEL staining and type 1 IFN production were also significantly diminished in the absence of MAVS (FIG. 3D-3G and data not shown). In contrast, CS-induced suppression of NLRX1 was not altered in lungs from MAVS$^{-/-}$ mice exposed to CS for up to 6 months (FIG. 3H). Next, to determine if MAVS played a critical roles in the enhancement CS-induced inflammation and alveolar destruction observed in NLRX1$^{-/-}$ mice, NLRX1 and MAVS double mutant (NLRX1$^{-/-}$/MAVS$^{-/-}$) mice and appropriate controls were exposed to CS for 3 months. These studies demonstrated that the enhanced emphysema, cell death, IL-18 production and CXCL13 production in NLRX1 single null mice exposed to CS was markedly decreased in similarly exposed double mutant mice (FIGS. 3I-3K, 15, and 16). Overall, these studies demonstrate that MAVS plays a critical role in the exaggerated inflammatory, remodeling, proteolytic, cell death and cytokine responses that are induced by CS in states of NLRX1 deficiency.

COPD is a major cause of morbidity and mortality and a major unmet medical need in the USA and the world(4). In keeping with its importance, studies of COPD and models of this disorder have highlighted the importance of antiviral innate immunity, protease excess, epithelial cell death, and inflammasome activation in disease pathogenesis (5, 6, 11, 19-23). The work described herein adds to and integrates these findings by demonstrating that mitochondria play an important role in the regulation of and the effector phase of CS-induced responses. Specifically they demonstrate that NLRX1 is an important inhibitor at baseline and that CS-stimulates inflammation and remodeling by suppressing NLRX1 which allows these MAVS-dependent responses to be seen. The inhibition of NLRX1 augmented antiviral innate immune responses, protease expression, cell death, and inflammasome activation thereby mechanistically integrating the present and prior observations. The disease relevance of these studies was also confirmed in studies that demonstrated that the expression of NLRX1 is decreased in lungs from patients with COPD where this suppression correlates with disease severity, abnormal pulmonary function, decreased quality of life and poor prognosis.

CS is an important stimulator of inflammation and remodeling in a variety of diseases and disorders (3, 24-26). It also exaggerates antiviral responses in patients with COPD and otherwise healthy smokers (11, 27, 28). The ability of CS and virus/viral PAMPs to synergize in the generation of inflammation and tissue remodeling is mediated by a MAVS-dependent mechanism (5). The present studies add to these observations by demonstrating that MAVS also plays a crucial role in the inflammation and remodeling induced by CS alone. Importantly they also revise our understanding of the mechanism that CS uses to engender tissue alterations. Specifically, they demonstrate that optimal CS-induced responses are only seen when CS abrogates the inhibitory effects of NLRX1.

NLRX1 is a member of the Nod-like receptor family of intracellular sensors of microbial- and danger-associated molecular patterns (15, 29). In early studies it was identified to be a negative regulator of MAVS, a key adapter molecule of M-RLH antiviral signaling(15). It is now known to be a negative modulator of LPS-induced TRAF6-NK-κB signaling and has been shown to regulate autophagy(14, 16, 30), bind to UQCRC2 in mitochondrial respiratory chain complex III and regulate mitochondrial production of reactive oxidant species (ROS)(31). This effector repetiore might have significant implications for the methods described herein because defects in autophagy/mitophagy lead to the accumulation of damaged, ROS producing, mitochondria which induce inflammasome activation(32). In accord with this concept, a recent publication demonstrated that MAVS also plays a role as a critical adaptor molecule in inflammasome activation (33). It is contemplated herein that NLRX1-inhibition of-MAVS-dependent inflammasome activation plays an important role in the pathogenesis of COPD.

It is demonstrated herein that NLRX1 is suppressed in patients with COPD where the degree of suppression correlates with disease severity. It is also demonstrated that the effects of CS are mediated by an NLRX1-inhibited and MAVS-dependent pathway and that interventions that abrogate the CS-induced decrease in NLRX1 also abrogate CS-induced emphysema. These studies demonstrate that the suppression of NLRX1 is a critical event in CS-induced responses. It is also contemplated herein that the degree of NLRX1 suppression can be an important index of COPD severity and that polymorphisms or other alterations that decrease NLRX1 function can contribute to disease susceptibility. Importantly, the demonstration that NLRX1 supplementation abrogates CS-induced alveolar destruction also indicates that interventions that prevent the inhibition of NLRX1, augment the effects of NLRX1, abrogate MAVS function or restore NLRX1 suppression can be therapeutically useful in this disorder.

Methods

Clinical Data.

Three cohorts were used in these studies. In the Yale cohort, fresh frozen lung tissues from 7 controls and 36 patients with COPD were obtained from the Lung Tissue Research Consortium (LTRC), a nationwide resource program from the National Heart, Lung, and Blood Institute (NHLBI) that provides human lung tissues with highly qualified and extensive phenotype data. This study was approved by the Yale University Human Investigation Committee and LTRC (#11-99-0005). For the Pittsburgh cohort, lung tissues were obtained as previously described(34).

Mouse Models.

All in vivo experiments in animals were approved by the Yale Animal Care and Use Committee (YACUC). The generation and basic characterization of MAVS null mutant and NLRX1 null mutant mice have been described previously(14, 35). The CS-induced murine emphysema model that was employed has been described previously(6, 18).

Laboratory Assessments.

Separation of the cytosol- and mitochondria-enriched fractions was undertaken using Qproteome mitochondrial isolation kit (Qiagen) as per the manufacturer's instructions. For the evaluation of lung morphometry, the left lung was inflated with 0.5% low temperature-melting agarose in 10% buffered formalin fixative at a constant pressure of 25 cm as described previously (5, 6). Alveolar size was estimated by the measurement of mean chord length of the air space as described previously (5, 6).

Statistical Analysis.

Comparisons of the levels of NLRX1 in patients with different stages of COPD were undertaken with Student's t-test, nonparametric Kruskal-Wallis and Mann-Whitney U tests as appropriate. To evaluate the associations between the levels of NLRX1 expression and clinical variables, nonparametric Pearson correlation analysis was undertaken. For the analyses of the murine data, groups were compared with Student's t test or with nonparametric Mann-Whitney U test as appropriate. Statistical significance was defined at a level of $p<0.05$. All analyses were completed with SPSS™ software, version 19.0.

REFERENCES

1. Adair-Kirk, T. L., Atkinson, J. J., and Senior, R. M. 2008. Smoke particulates stress lung cells. *Nat Med* 14:1024-1025.
2. Yanbaeva, D. G., Dentener, M. A., Creutzberg, E. C., Wesseling, G., and Wouters, E. F. 2007. Systemic effects of smoking. *Chest* 131:1557-1566.
3. Bhalla, D. K., Hirata, F., Rishi, A. K., and Gairola, C. G. 2009. Cigarette smoke, inflammation, and lung injury: a mechanistic perspective. *J Toxicol Environ Health B Crit Rev* 12:45-64.
4. Rabe, K. F., Hurd, S., Anzueto, A., Barnes, P. J., Buist, S. A., Calverley, P., Fukuchi, Y., Jenkins, C., Rodriguez-Roisin, R., van Weel, C., et al. 2007. Global strategy for the diagnosis, management, and prevention of chronic obstructive pulmonary disease: GOLD executive summary. *Am J Respir Crit Care Med* 176:532-555.
5. Kang, M. J., Lee, C. G., Lee, J. Y., Dela Cruz, C. S., Chen, Z. J., Enelow, R., and Elias, J. A. 2008. Cigarette smoke selectively enhances viral PAMP- and virus-induced pulmonary innate immune and remodeling responses in mice. *J Clin Invest* 118:2771-2784.
6. Kang, M. J., Homer, R. J., Gallo, A., Lee, C. G., Crothers, K. A., Cho, S. J., Rochester, C., Cain, H., Chupp, G., Yoon, H. J., et al. 2007. IL-18 is induced and IL-18 receptor alpha plays a critical role in the pathogenesis of cigarette smoke-induced pulmonary emphysema and inflammation. *J Immunol* 178:1948-1959.
7. Eltom, S., Stevenson, C. S., Rastrick, J., Dale, N., Raemdonck, K., Wong, S., Catley, M. C., Belvisi, M. G., and Birrell, M. A. 2011. P2X7 receptor and caspase 1 activation are central to airway inflammation observed after exposure to tobacco smoke. *PLoS One* 6: e24097.
8. Nunnari, J., and Suomalainen, A. 2012. Mitochondria: in sickness and in health. *Cell* 148:1145-1159.
9. West, A. P., Shadel, G. S., and Ghosh, S. 2011. Mitochondria in innate immune responses. *Nat Rev Immunol* 11:389-402.
10. Arnoult, D., Soares, F., Tattoli, I., and Girardin, S. E. 2011. Mitochondria in innate immunity. *EMBO Rep* 12:901-910.
11. Wedzicha, J. A. 2004. Role of viruses in exacerbations of chronic obstructive pulmonary disease. *Proc Am Thorac Soc* 1:115-120.
12. Seemungal, T., Harper-Owen, R., Bhowmik, A., Moric, I., Sanderson, G., Message, S., Maccallum, P., Meade, T. W., Jeffries, D. J., Johnston, S. L., et al. 2001. Respiratory viruses, symptoms, and inflammatory markers in acute exacerbations and stable chronic obstructive pulmonary disease. *Am J Respir Crit Care Med* 164:1618-1623.
13. Belgnaoui, S. M., Paz, S., and Hiscott, J. 2011. Orchestrating the interferon antiviral response through the mitochondrial antiviral signaling (MAVS) adapter. *Curr Opin Immunol* 23:564-572.
14. Allen, I. C., Moore, C. B., Schneider, M., Lei, Y., Davis, B. K., Scull, M. A., Gris, D., Roney, K. E., Zimmermann, A. G., Bowzard, J. B., et al. 2011. NLRX1 protein attenuates inflammatory responses to infection by interfering with the RIG-I-MAVS and TRAF6-NF-kappaB signaling pathways. *Immunity* 34:854-865.
15. Moore, C. B., Bergstralh, D. T., Duncan, J. A., Lei, Y., Morrison, T. E., Zimmermann, A. G., Accavitti-Loper, M. A., Madden, V. J., Sun, L., Ye, Z., et al. 2008. NLRX1 is a regulator of mitochondrial antiviral immunity. *Nature* 451:573-577.
16. Lei, Y., Wen, H., Yu, Y., Taxman, D. J., Zhang, L., Widman, D. G., Swanson, K. V., Wen, K. W., Damania, B., Moore, C. B., et al. 2012. The mitochondrial proteins NLRX1 and TUFM form a complex that regulates type I interferon and autophagy. *Immunity* 36:933-946.
17. Litsiou, E., Semitekolou, M., Galani, I. E., Morianos, I., Tsoutsa, A., Kara, P., Rontogianni, D., Bellenis, I., Konstantinou, M., Potaris, K., et al. 2013. CXCL13 Production in B cells via TLR/Lymphotoxin Receptor Signaling are Involved in Lymphoid Neogenesis in COPD. *Am J Respir Crit Care Med*.
18. Hautamaki, R. D., Kobayashi, D. K., Senior, R. M., and Shapiro, S. D. 1997. Requirement for macrophage elastase for cigarette smoke-induced emphysema in mice. *Science* 277:2002-2004.
19. MacNee, W., and Tuder, R. M. 2009. New paradigms in the pathogenesis of chronic obstructive pulmonary disease I. *Proc Am Thorac Soc* 6:527-531.
20. Decramer, M., Janssens, W., and Miravitlles, M. 2012. Chronic obstructive pulmonary disease. *Lancet* 379:1341-1351.
21. Cosio, M. G., Saetta, M., and Agusti, A. 2009. Immunologic aspects of chronic obstructive pulmonary disease. *N Engl J Med* 360:2445-2454.

22. Taraseviciene-Stewart, L., and Voelkel, N. F. 2008. Molecular pathogenesis of emphysema. *J Clin Invest* 118:394-402.
23. Tuder, R. M., and Petrache, I. 2012. Pathogenesis of chronic obstructive pulmonary disease. *J Clin Invest* 122:2749-2755.
24. Celli, B. R. 2012. Chronic obstructive pulmonary disease and lung cancer: common pathogenesis, shared clinical challenges. *Proc Am Thorac Soc* 9:74-79.
25. Babizhayev, M. A., and Yegorov, Y. E. 2011. Smoking and health: association between telomere length and factors impacting on human disease, quality of life and life span in a large population-based cohort under the effect of smoking duration. *Fundam Clin Pharmacol* 25:425-442.
26. Arnson, Y., Shoenfeld, Y., and Amital, H. 2010. Effects of tobacco smoke on immunity, inflammation and autoimmunity. *J Autoimmun* 34:J258-265.
27. Kark, J. D., Lebiush, M., and Rannon, L. 1982. Cigarette smoking as a risk factor for epidemic a(h1n1) influenza in young men. *N Engl J Med* 307:1042-1046.
28. Kark, J. D., and Lebiush, M. 1981. Smoking and epidemic influenza-like illness in female military recruits: a brief survey. *Am J Public Health* 71:530-532.
29. Davis, B. K., Wen, H., and Ting, J. P. 2011. The inflammasome NLRs in immunity, inflammation, and associated diseases. *Annu Rev Immunol* 29:707-735.
30. Xia, X., Cui, J., Wang, H. Y., Zhu, L., Matsueda, S., Wang, Q., Yang, X., Hong, J., Songyang, Z., Chen, Z. J., et al. 2011. NLRX1 negatively regulates TLR-induced NF-kappaB signaling by targeting TRAF6 and IKK. *Immunity* 34:843-853.
31. Arnoult, D., Soares, F., Tattoli, I., Castanier, C., Philpott, D. J., and Girardin, S. E. 2009. An N-terminal addressing sequence targets NLRX1 to the mitochondrial matrix. *J Cell Sci* 122:3161-3168.
32. Zhou, R., Yazdi, A. S., Menu, P., and Tschopp, J. 2011. A role for mitochondria in NLRP3 inflammasome activation. *Nature* 469:221-225.
33. Subramanian, N., Natarajan, K., Clatworthy, M. R., Wang, Z., and Germain, R. N. 2013. The adaptor MAVS promotes NLRP3 mitochondrial localization and inflammasome activation. *Cell* 153:348-361.
34. Shi, Y., Cao, J., Gao, J., Zheng, L., Goodwin, A., An, C. H., Patel, A., Lee, J. S., Duncan, S. R., Kaminski, N., et al. 2012. Retinoic acid-related orphan receptor-alpha is induced in the setting of DNA damage and promotes pulmonary emphysema. *Am J Respir Crit Care Med* 186:412-419.
35. Sun, Q., Sun, L., Liu, H. H., Chen, X., Seth, R. B., Forman, J., and Chen, Z. J. 2006. The specific and essential role of MAVS in antiviral innate immune responses. *Immunity* 24:633-642.

Table 1.

Clinical Characteristics of the Study Populations. Values are presented as means±standard deviation (STD) in LTRC Yale Cohort (a), Pittsburgh Cohort (b) and Korean Asan cohort, respectively. # The Global Initiative for Chronic Obstructive Lung Disease (GOLD) stage range from stage 1 (GOLD 1) COPD, indicating mild disease, to stage IV (GOLD 4) COPD, indicating very severe disease. § $FEV_1$ (%), pre-BD denotes prebronchodilator $FEV_1$ (% of predicted value). $FEV_1$(%), post-BD denotes postbronchodilator $FEV_1$ (% of predicted value). $D_{LCO}$ denotes diffusing capacity. The BODE index stands for body mass index (BMI), obstruction, dyspnea and exercise capacity. The SGRQ score denotes Saint George Respiratory Questionnaires score. The BORG scale at termination is the extent of perceived patient exertion that can be estimated by the Borg scale at the termination of exercise.

(a) LTRC Cohort

| | | COPD[#] | | | |
|---|---|---|---|---|---|
| Characteristic[§] | Control | GOLD 1 | GOLD 2 | GOLD 3 | GOLD 4 |
| Number | 7 | 6 | 10 | 10 | 10 |
| age (yr) | 57.7 ± 10.7 | 73.7 ± 6.9 | 66.3 ± 9.7 | 64.2 ± 6.9 | 54.0 ± 7.2 |
| Gender (Male:Female) | (2:5) | (5:1) | (10:0) | (7:3) | (6:4) |
| Smokers (Non-smokers) | 3 (4) | 6 | 10 | 10 | 10 |
| Smoking history - pack-yr | 15.4 ± 19.5 | 36.5 ± 10.8 | 54.1 ± 24.6 | 62.0 ± 25.7 | 51.8 ± 38.2 |
| $FEV_1$ (%), Pre-BD | 93.0 ± 12.1 | 82.7 ± 10.3 | 61.6 ± 6.9 | 32.2 ± 4.2 | 21.5 ± 7.7 |
| $FEV_1$ (%), Post BD | 98.2 ± 12.4 | 89.2 ± 6.9 | 67.7 ± 5.6 | 34.2 ± 3.3 | 19.8 ± 2.8 |
| $D_{LCO}$ | 96.4 ± 26.6 | 80.4 ± 16.9 | 51.75 ± 24.6 | 31.3 ± 6.3 | 39.2 ± 16.6 |
| 6 minute Walking-Distance | 413.5 ± 43.8 | 321. ±, 35.6 | 318.5 ± 168.9 | 237.2 ± 88.9 | 270.5 ± 69.6 |
| BODE Index | 0.1 ± 0.4 | 1.1 ± 1.1 | 2.9 ± 2.6 | 6.8 ± 1.6 | 6.8 ± 1.1 |
| SGRQ Score | 5.3 ± 9.8 | 18.1 ± 20.6 | 36.9 ± 27.7 | 67.0 ± 10.9 | 59.2 ± 15.1 |
| BORG Scale at Termination | 0.8 ± 0.3 | 1.0 ± 1.4 | 3.3 ± 1.4 | 4.3 ± 1.9 | 4.9 ± 2.6 |
| NLRX1 mRNA (standardized) | 1.22 ± 0.73 | 1.35 ± 0.39 | 1.22 ± 0.63 | 0.78 ± 0.29 | 0.73 ± 0.28 |

(b) Pittsburgh Cohort

| Characteristic | Control (n = 63) | <1% emphysema (n = 20) | 1-10% emphysema (n = 51) | >40% emphysema (n = 26) |
|---|---|---|---|---|
| Age | 65.8 ± 10.3 | 67.9 ± 8.4 | 68.4 ± 8.4 | 56.2 ± 7.2 |
| Female Gender | 27 (43%) | 8 (40%) | 17 (33%) | 16 (62%) |
| Race | 2 African-American | 20 Caucasian | 1 African-American | 26 Caucasian |

-continued

| Characteristic | Control (n = 63) | <1% emphysema (n = 20) | 1-10% emphysema (n = 51) | >40% emphysema (n = 26) |
|---|---|---|---|---|
| | 58 Caucasian 3 Other | | 50 Caucasian | |
| Pack-Years | 26.3 ± 34.3 | 56.1 ± 31.2 | 65.1 ± 40.0 | 50.8 ± 25.6 |
| FEV1 (% predicted) | 97.4 ± 9.2 | 63.5 ± 12.0 | 60.3 ± 13.9 | 24.2 ± 8.2 |
| FVC (% predicted) | 93.3 ± 11.8 | 74.9 ± 12.7 | 83.4 ± 15.7 | 56.0 ± 18.7 |
| DLCO (% predicted) | 81.9 ± 16.3 | 70.4 ± 21.8 | 62.4 ± 16.1 | 31.5 ± 8.5 |
| HU <− 950 (%) | 0.7 ± 1.1 | 0.4 ± 0.3 | 4.2 ± 2.5 | 48.7 ± 6.9 |

(c) Asan Cohort

| Characteristic | Control | GOLD 1 | GOLD 2 | GOLD 3 |
|---|---|---|---|---|
| Number (M:F) | 94 (94:0) | 45 (45:0) | 53 (53:0) | 1 (1:0) |
| age (mean, STD) | 60.6 ± 9.4 | 68.3 ± 6.1 | 66.9 ± 6.5 | 61 |
| Smoker (NS:CS) | (94:0) | (45:0) | (53:0) | (1:0) |
| PKYrs (mean, STD) | 34.8 ± 17.1 | 49.5 ± 19.4 | 46.3 ± 24.1 | 40 |
| FEV1 (%), Pre-BD (mean, STD) | 91.0 ± 12.4 | 83.7 ± 8.3 | 63.5 ± 7.6 | 28 |
| FEV1 (%), Post BP (mean, STD) | 94.3 ± 12.8 | 89.2 ± 6.8 | 68.4 ± 6.7 | 34 |
| $D_{LCO}$ (mean, STD) | 92.9 ± 12.9 | 78.3 ± 13.9 | 76.1 ± 14.6 | 86 |
| NLRX1 transcriptome (mean, STD) | 2.22 ± 1.49 | 1.69 ± 1.34 | 1.39 ± 0.87 | 1.06 |

Supplemental Methods

Study Populations. Three cohorts were used in these studies. In the Yale cohort, fresh frozen lung tissues from 7 controls and 36 patients with COPD were obtained from the Lung Tissue Research Consortium (LTRC)(1), as described in the main text. For the Pittsburgh cohort, lung tissues were obtained as previously described(2). Briefly, controls (n=63) were defined as the subjects who have no evidence of chronic lung disease as well as normal pulmonary function tests including lung volumes. The subjects with COPD had varying levels of emphysema which were measured by quantitative CT using HU<−950 as a cutoff. The subjects with COPD were further stratified by the amount of quantitative emphysema with the three categories including <1%, which denotes less than 1% emphysema (n=22); 1-10%, which denotes a low level of emphysema between 1 and 10 percent (n=45); and the most severe cases, with more than 40% emphysema (n=27). The characteristics of these patients can be seen in Table 1b. For the Asan cohort, subjects were patients who required resection for lung cancer and who were registered in the Asan Biobank. Inclusion criteria were a $FEV_1$/FVC ratio of less than 0.7 for the COPD group, and normal spirometry for the control group. This study was approved by the institutional review board of Asan Medical Center (#2011-0711) and written informed consent was obtained from all patients.

RNA preparation and sequencing for human studies. For the Yale cohort, the mRNAs were extracted from fresh frozen lung tissues from the 7 controls and 36 patients with COPD in the NIH-sponsored Lung Tissue Research Consortium (LTRC) cohort. cDNA synthesis and real-time reverse-transcriptase-polymerase-chain-reaction (RT-PCR) assays were performed with whole RNA extracted from fresh frozen human lung tissues using Bio-Rad kits as per the manufacturer's instructions. The human NLRX1 primers from Primerbank(3) were utilized for the evaluation of the Yale cohort. For the Asan cohort, total RNA was isolated from apparently normal fresh frozen lung tissue that was remote from the lung cancer. RNA integrity was assessed using an Agilent Bioanalyzer™ and RNA purity was assessed using a NanoDrop™ spectrophotometer. One µg of total RNA was used to generate cDNA libraries using the TruSeq™ RNA library kit. The protocol consisted of poly A-selected RNA extraction, RNA fragmentation, reverse transcription using random hexamer primers, and 100 bp paired-end sequencing using the Illumina HiSeq™ 2000 system. The libraries were quantified using quantitative PCR according to the quantitative PCR Quantification Protocol Guide and qualified using an Agilen Technologies 2100 Bioanalyzer™. For quality control, read quality was verified using FastQC™ and read alignment was verified using Picard™. Differential gene expression (DEG) analysis was performed using TopHat™ and Cufflinks™ software(4). To estimate expression levels, the RNA-seq reads were mapped to the human genome using TopHat™ (version 1.4.1)(5), and quantified using Cufflinks™ software (2.0.0)(6). Cufflinks™ software was run with the UCSC hg19 human genome and transcriptome references. The numbers of isoform and gene transcripts were calculated and the relative abundance of transcripts was measured in fragments per kilobase of exon per million fragments mapped (FPKM) using Cufflinks software. Expression levels were extracted as a FPKM value for each gene of each sample using Cufflinks™ software. Genes with FPKM values of 0 across all samples were excluded. Filtered data were subject to upper quantile normalization. Statistical significance was determined using Student's t-test. The false discovery rate (FDR) was controlled by adjusting p values using the Benjamini-Hochberg algorithm.

Laboratory Assessments. Separation of the cytosol- and mitochondria-enriched fractions was undertaken using Qproteome™ mitochondrial isolation kit (Qiagen) as per the manufacturer's instructions. Immunoblot analyses were undertaken using antibodies for NLRX1 (Proteintech), caspase-1 (Cell Signaling), IL-1β (Santa Cruz), IL-18 (Santa Cruz) and β-actin (Cell Signaling). Immunohistochemstiry for NLRX1 was undertaken to localize the expression of NLRX1. For the evaluation of lung morphometry, subgroups of 5-7 mice were used for the evaluation of mean chord length and the surface area of the lungs following stereological analysis of the lungs according to the ATS/ERS guidelines(7, 8). Briefly, the left lung was inflated with 0.5% low temperature-melting agarose in 10% buffered formalin fixative at a constant pressure of 25 cm as described previously (9, 10). After the fixation, lung volume ($V_L$) of the left lung was determined by the water immersion method. The images were taken equally spaced and systematically placed meander-like over the whole surface of the lung sections. Pictures were quantitatively analyzed by using a test system of points and lines superimposed over the digital images via the STEPanizer™ program (11). The intersecting points falling on alveolar space (Pa), alveolar ducts (Pd), and points falling on septum (Ps) were counted separately among total points (Ptotal). Point counts yielded relative volume densities and alveolar surface area (S) was calculated by the following formula; (1) Airspace fraction ($F_A$)=(Pa+Pd+Ps)/Ptotal; (2) Airspace volume ($V_A$)=$F_A \times V_L$; (3) S=$4V_A$/Lm (mean linear intercept). In addition, mean chord length of the air space was evaluated as described previously by our laboratory(9, 10). Lung tissue lysates were prepared and the levels of tissue CXCL13, IL-1β and IL-18 (R&D Systems) were determined using commercial ELISA kits as per the manufacturer's instructions. For the evaluation of apoptotic cell death/DNA injury, end labeling of exposed 3'-OH ends of DNA fragments in paraffin embedded tissue was undertaken with the TUNEL in situ cell death detection kit AP (Roche Diagnostics) using the instructions provided by the manufacturer. To overexpress NLRX1 gene in vivo, the gene was integrated into lentiviral vector. The lentiviral vector backbones used in this study were purchased from System Biosciences Inc. (SBI, CA, USA, Catalog #CD511B-1). The NLRX1 cDNA clone was purchased from Origene (Origene, Md., USA, Catalog #MC204753). pPACKH1-XL HIV Lentivector Packaging Kit (SBI, CA, USA, Catalog #LV510A-1) and virus precipitation solution (SBI, CA, USA, Catalog #LV810A-1) were used to package the lentiviral vectors, according to the manufacturer's instructions. The lentiviral titer kit (SBI, CA, USA, Catalog #LV961A-1) was used to determine the amount of viral vectors according to the manufacturer's instructions. Intranasal administration of either the lenti-NLRX1, or lenti-control vectors was performed on 6-wk-old C57BL/6J male mice. The amount of $1 \times 10^8$ TU of lenti-NLRX1 or lenti-control vectors per mouse was administered. CS exposure experiment was started from 2 weeks after intranasal treatment.

REFERENCES

1. LTRC. Lung Tissue Research Consortium. available at nhlbi.nih.gov/resources/ltrc.htm.
2. Shi, Y., Cao, J., Gao, J., Zheng, L., Goodwin, A., An, C. H., Patel, A., Lee, J. S., Duncan, S. R., Kaminski, N., et al. 2012. Retinoic acid-related orphan receptor-alpha is induced in the setting of DNA damage and promotes pulmonary emphysema. *Am J Respir Crit Care Med* 186:412-419.
3. PrimerBank. available at pga.mgh.harvard.edu/primerbank/.
4. Trapnell, C., Roberts, A., Goff, L., Pertea, G., Kim, D., Kelley, D. R., Pimentel, H., Salzberg, S. L., Rinn, J. L., and Pachter, L. 2012. Differential gene and transcript expression analysis of RNA-seq experiments with TopHat and Cufflinks. *Nat Protoc* 7:562-578.
5. Trapnell, C., Pachter, L., and Salzberg, S. L. 2009. TopHat: discovering splice junctions with RNA-Seq. *Bioinformatics* 25:1105-1111.
6. Trapnell, C., Williams, B. A., Pertea, G., Mortazavi, A., Kwan, G., van Baren, M. J., Salzberg, S. L., Wold, B. J., and Pachter, L. 2010. Transcript assembly and quantification by RNA-Seq reveals unannotated transcripts and isoform switching during cell differentiation. *Nat Biotechnol* 28:511-515.
7. Hsia, C. C., Hyde, D. M., Ochs, M., and Weibel, E. R. 2010. An official research policy statement of the American Thoracic Society/European Respiratory Society: standards for quantitative assessment of lung structure. *Am J Respir Crit Care Med* 181:394-418.
8. Muhlfeld, C., and Ochs, M. 2013. Quantitative microscopy of the lung: a problem-based approach. Part 2: stereological parameters and study designs in various diseases of the respiratory tract. *Am J Physiol Lung Cell Mol Physiol* 305:L205-221.
9. Kang, M. J., Lee, C. G., Lee, J. Y., Dela Cruz, C. S., Chen, Z. J., Enelow, R., and Elias, J. A. 2008. Cigarette smoke selectively enhances viral PAMP- and virus-induced pulmonary innate immune and remodeling responses in mice. *J Clin Invest* 118:2771-2784.
10. Kang, M. J., Homer, R. J., Gallo, A., Lee, C. G., Crothers, K. A., Cho, S. J., Rochester, C., Cain, H., Chupp, G., Yoon, H. J., et al. 2007. IL-18 is induced and IL-18 receptor alpha plays a critical role in the pathogenesis of cigarette smoke-induced pulmonary emphysema and inflammation. *J Immunol* 178:1948-1959.
11. Tschanz, S. A., Burri, P. H., and Weibel, E. R. 2011. A simple tool for stereological assessment of digital images: the STEPanizer. *J Microsc* 243:47-59.

---

What is claimed herein is:

1. A method of decreasing chord length in the lung of a subject in need of treatment for alveoli loss, the method comprising administering an inhibitor of Mitochondrial AntiViral Signaling protein (MAVS), wherein the inhibitor of MAVS is a NOD-Like Receptor family member X1 (NLRX1) agonist comprising a nucleic acid encoding NLRX1, and wherein the subject is a subject determined to have a decreased level of NLRX1 expression determined using a method selected from the group consisting of: RT-PCR; quantitative RT-PCR; Northern blot; microarray-based expression analysis; next-generation sequencing; and RNA in situ hybridization.

2. The method of claim 1, wherein the level of NLRX1 is determined by measuring the level of NLRX1 RNA transcript.

* * * * *

SEQUENCE LISTING

<160> NUMBER OF SEQ ID NOS: 4

<210> SEQ ID NO 1
<211> LENGTH: 4158
<212> TYPE: DNA
<213> ORGANISM: Homo sapiens

<400> SEQUENCE: 1

```
agtactagcg gcagtgcccg cggggatgga ggcagggagg ggggacgatg gcgggacggg      60
tggcgccggg gttccagccc tgcgcctgct ccggagcacc gggcccctct cgctgacccc     120
ctcgtcccag gaccccgcag gcccgagtgc ctgggctcgt cctctttcgc gcccgctgcc     180
aggtgccagg gccgcgcagg cgggcggagg tgggcaggaa gcgccacgcc gaggagccgg     240
```

```
ggactctggg agctagcggg agacgccggc gtccgcccag ccgacccctc tgggccgcgg      300
ccgacggctc ccggaactgg gcagccgcgg gtaaaggcct agcgggcttg ataaccctg       360 cgccctggct gggaggccgc gctgagcggg gggcagggcg ggccggggga ggaggctgtg      420
caagggccgc ggggagatcc cggccgagaa cgagagggac ggagctgggc gctgaatggc      480
gggcgttctg gcaagtctcc ccctgcgttc ccgaggccac ccgaaagtag gagagctgtt     540
tgggacccag tttggtggag gagctctgga cctgtaggaa caccgcccct gacagaagtc      600
ggtcctaggc cccccaggct ctgaccttct ttcccaggat gaggtggggc caccatttgc      660
ccagggcctc ttggggctct ggttttagaa gagcactcca gcgaccagat gatcgtatcc     720
ccttcctgat ccactggagt tggccccttc aaggggagcg tccctttggg cccctaggg       780 cctttatacg ccaccacgga agctcggtag atagcgctcc cccacccggg aggcatggac      840
ggctgttccc cagcgcctct gcaactgaag ctatacagcg gcaccgccgg aacctggctg     900
agtggttcag ccggctgccc agggaggagc gccagtttgg cccaacccttt gcccctagaca   960 cggtccacgt tgaccctgtg atccgcgaga gtaccctga tgagctactt cgcccacccg     1020
cggagctggc cctggagcat cagccacccc aggccgggct cccccactg gccttgtctc     1080 agctctttaa cccggatgcc tgtgggcgcc gggtgcagac agtggtgctg tatgggacag     1140
tgggcacagg caagagcacg ctggtgcgca agatggttct ggactggtgt tatgggcggc     1200
tgccggcctt cgagctgctc atccccttct cctgtgagga cctgtcatcc ctgggccctg     1260
ccccagcctc cctgtgccaa cttgtggccc agcgctacac gcccctgaag gaggttctgc     1320
ccctgatggc tgctgctggg tcccacctcc tctttgtgct ccatggctta gagcatctca     1380
acctcgactt ccggctggca ggcacgggac tttgtagtga cccggaggaa ccgcaggaac     1440
cagctgctat catcgtcaac ctgctgcgca aatacatgct gcctcaggcc agcattctgg     1500
tgaccactcg gcctctgcc attggccgta tccccagcaa gtacgtgggc cgctatggtg     1560
agatctgcgt tttctctgat accaacctgc agaagctcta cttccagctc cgcctcaacc     1620
agccgtactg cgggtatgcc gttggcggtt caggtgtctc tgccacacca gctcagcgtg     1680
accacctggt gcagatgctc tcccggaacc tggaggggca ccaccagata gccgctgcct     1740
gcttcctgcc gtcctattgc tggctcgttt gtgccacctt gcacttcctg catgccccca     1800
cgcctgctgg gcagacccct acaagcatct ataccagctt cctgcgcctc aacttcagcg     1860
gggaaaccct ggacagcact gaccctccca atttgtccct gatggcctat gcagcccgaa     1920
ccatgggcaa gttggcctat gaggggtgt cctcccgcaa gacctacttc tctgaagagg     1980
atgtctgtgg ctgcctggag gctggcatca ggacggagga ggagtttcag ctgctgcaca     2040
tcttccgtcg ggatgccctg aggttttttcc tggccccatg tgtggagcca gggcgtgcag     2100
gcaccttcgt gttcaccgtg cccgccatgc aggaatacct ggctgccctc tacattgtgc     2160
tgggtttgcg caagacgacc ctgcaaaagg tgggcaagga agtggctgag ctcgtgggcc     2220
gtgttgggga ggacgtcagc ctggtactgg gcatcatggc caagctgctg cctctgcggg     2280
ctctgcctct gctcttcaac ctgatcaagg tggttccacg agtgtttggg cgcatggtgg     2340
gtaaaagccg ggaggcggtg gctcaggcca tggtgctgga gatgtttcga gaggaggact     2400
actacaacga tgatgttctg gaccagatgg cgccagtat cctgggcgtg gagggccccc     2460
ggcgccaccc agatgagccc cctgaggatg aagtcttcga gctcttcccc atgttcatgg     2520
gggggcttct ctctgcccac aaccgagctg tgctagctca gcttggctgc cccatcaaga     2580
acctggatgc cctggagaat gcccaggcca tcaagaagaa gctgggcaag ctgggccggc     2640
```

```
aggtgctgcc cccatcagag ctccttgacc acctcttctt ccactatgag ttccagaacc    2700
agcgcttctc cgctgaggtg ctcagctccc tgcgtcagct caacctggca ggtgtgcgca    2760
tgacaccagt caagtgcaca gtggtggcag ctgtgctggg cagcggaagg catgccctgg    2820
atgaggtgaa cttggcctcc tgccagctag atcctgctgg gctgcgcaca ctcctgcctg    2880
tcttcctgcg tgcccggaag ctgggcttgc aactcaacag cctgggccct gaggcctgca    2940
aggacctccg agacctgttg ctgcatgacc agtgccaaat taccacactg cggctgtcca    3000
acaacccgct gacggcggca ggtgttgccg tgctaatgga ggggctggca ggaaacacct    3060
cagtgacgca cctgtccctg ctgcacacgg ccttgggga cgaaggcctg gagctgctgg    3120
ctgcccagct ggaccgcaac cggcagctgc aggagctgaa cgtggcgtac aacggtgctg    3180
gtgacacagc ggccctggcc ctggccagag ctgcccggga gcaccttcc ctggaactgc    3240 tacacctcta cttcaatgag ctgagctcag agggccgcca ggtcttgcga gacttggggg    3300
gtgctgctga aggtggtgcc cggtggtgg tgtcactgac agaggggacg gcggtgtcag    3360
aatactggtc agtgatcctc agtgaagtcc agcggaacct caatagctgg gatcgggccc    3420
gggttcagcg acaccttgag ctcctactgc gggatctgga agatagccgg ggtgccaccc    3480
ttaatccttg gcgcaaggcc cagctgctgc gagtggaggg cgaggtcagg gccctcctgg    3540
agcagctggg aagctctgga agctgagaca ctggcggcag gcacctagct atgtgaccac    3600
tggccctaaa cctttccct ctgtggcctc ctggcttgca ctgctccctc tagaaagatt    3660
ccttcaggtc tggaggcaga ggaatgggca tagctgagcc agttgccctc ctagggcatg    3720
tttgaccagg actgagtctg gaatctccaa gttaaagatg gtgaatcaat gcttcgggct    3780
tggagatgga acatgcctcc tctccattca gctagaagga ccaaagcatg tggcatttgg    3840
atggccagag tgccctgaag caccactacc aaccttgcct cccctcctc tcaaagagcc    3900 tctgactgtg tcaccaaggg gctcacatct tatgtctgcc atgccagggg tgtcgccatc    3960
cagatgtgtt ggaagcttcc cctcctgcct tatgctcacc tgtggacacc gaggatgccc    4020
tcacattggt gctttctcct catcctcatg cccccttgc cacaatggta tgatggcttg    4080
gtagcccctc gaggcagatg cacctgactt gctgctatta aaaagccgtg tgccttctac    4140
caaaaaaaaa aaaaaaaa                                                   4158
```

<210> SEQ ID NO 2
<211> LENGTH: 975
<212> TYPE: PRT
<213> ORGANISM: Homo sapiens

<400> SEQUENCE: 2

```
Met Arg Trp Gly His His Leu Pro Arg Ala Ser Trp Gly Ser Gly Phe
1               5                   10                  15

Arg Arg Ala Leu Gln Arg Pro Asp Asp Arg Ile Pro Phe Leu Ile His
                20                  25                  30

Trp Ser Trp Pro Leu Gln Gly Glu Arg Pro Phe Gly Pro Pro Arg Ala
            35                  40                  45

Phe Ile Arg His His Gly Ser Ser Val Asp Ser Ala Pro Pro Pro Gly
        50                  55                  60

Arg His Gly Arg Leu Phe Pro Ser Ala Ser Ala Thr Glu Ala Ile Gln
65                  70                  75                  80

Arg His Arg Arg Asn Leu Ala Glu Trp Phe Ser Arg Leu Pro Arg Glu
                85                  90                  95
```

```
Glu Arg Gln Phe Gly Pro Thr Phe Ala Leu Asp Thr Val His Val Asp
            100                 105                 110

Pro Val Ile Arg Glu Ser Thr Pro Asp Glu Leu Leu Arg Pro Pro Ala
        115                 120                 125

Glu Leu Ala Leu Glu His Gln Pro Pro Gln Ala Gly Leu Pro Pro Leu
    130                 135                 140

Ala Leu Ser Gln Leu Phe Asn Pro Asp Ala Cys Gly Arg Arg Val Gln
145                 150                 155                 160

Thr Val Val Leu Tyr Gly Thr Val Gly Thr Gly Lys Ser Thr Leu Val
                165                 170                 175

Arg Lys Met Val Leu Asp Trp Cys Tyr Gly Arg Leu Pro Ala Phe Glu
            180                 185                 190

Leu Leu Ile Pro Phe Ser Cys Glu Asp Leu Ser Ser Leu Gly Pro Ala
        195                 200                 205

Pro Ala Ser Leu Cys Gln Leu Val Ala Gln Arg Tyr Thr Pro Leu Lys
    210                 215                 220

Glu Val Leu Pro Leu Met Ala Ala Gly Ser His Leu Leu Phe Val
225                 230                 235                 240

Leu His Gly Leu Glu His Leu Asn Leu Asp Phe Arg Leu Ala Gly Thr
                245                 250                 255

Gly Leu Cys Ser Asp Pro Glu Glu Pro Gln Glu Pro Ala Ala Ile Ile
            260                 265                 270

Val Asn Leu Leu Arg Lys Tyr Met Leu Pro Gln Ala Ser Ile Leu Val
        275                 280                 285

Thr Thr Arg Pro Ser Ala Ile Gly Arg Ile Pro Ser Lys Tyr Val Gly
    290                 295                 300

Arg Tyr Gly Glu Ile Cys Gly Phe Ser Asp Thr Asn Leu Gln Lys Leu
305                 310                 315                 320

Tyr Phe Gln Leu Arg Leu Asn Gln Pro Tyr Cys Gly Tyr Ala Val Gly
                325                 330                 335

Gly Ser Gly Val Ser Ala Thr Pro Ala Gln Arg Asp His Leu Val Gln
            340                 345                 350

Met Leu Ser Arg Asn Leu Glu Gly His His Gln Ile Ala Ala Ala Cys
        355                 360                 365

Phe Leu Pro Ser Tyr Cys Trp Leu Val Cys Ala Thr Leu His Phe Leu
    370                 375                 380

His Ala Pro Thr Pro Ala Gly Gln Thr Leu Thr Ser Ile Tyr Thr Ser
385                 390                 395                 400

Phe Leu Arg Leu Asn Phe Ser Gly Glu Thr Leu Asp Ser Thr Asp Pro
                405                 410                 415

Ser Asn Leu Ser Leu Met Ala Tyr Ala Ala Arg Thr Met Gly Lys Leu
            420                 425                 430

Ala Tyr Glu Gly Val Ser Ser Arg Lys Thr Tyr Phe Ser Glu Glu Asp
        435                 440                 445

Val Cys Gly Cys Leu Glu Ala Gly Ile Arg Thr Glu Glu Phe Gln
    450                 455                 460

Leu Leu His Ile Phe Arg Arg Asp Ala Leu Arg Phe Phe Leu Ala Pro
465                 470                 475                 480

Cys Val Glu Pro Gly Arg Ala Gly Thr Phe Val Phe Thr Val Pro Ala
                485                 490                 495

Met Gln Glu Tyr Leu Ala Ala Leu Tyr Ile Val Leu Gly Leu Arg Lys
            500                 505                 510

Thr Thr Leu Gln Lys Val Gly Lys Glu Val Ala Glu Leu Val Gly Arg
```

```
            515                 520                 525
Val Gly Glu Asp Val Ser Leu Val Leu Gly Ile Met Ala Lys Leu Leu
530                 535                 540

Pro Leu Arg Ala Leu Pro Leu Leu Phe Asn Leu Ile Lys Val Val Pro
545                 550                 555                 560

Arg Val Phe Gly Arg Met Val Gly Lys Ser Arg Glu Ala Val Ala Gln
                565                 570                 575

Ala Met Val Leu Glu Met Phe Arg Glu Glu Asp Tyr Tyr Asn Asp Asp
                580                 585                 590

Val Leu Asp Gln Met Gly Ala Ser Ile Leu Gly Val Glu Gly Pro Arg
                595                 600                 605

Arg His Pro Asp Glu Pro Pro Glu Asp Glu Val Phe Glu Leu Phe Pro
                610                 615                 620

Met Phe Met Gly Gly Leu Leu Ser Ala His Asn Arg Ala Val Leu Ala
625                 630                 635                 640

Gln Leu Gly Cys Pro Ile Lys Asn Leu Asp Ala Leu Glu Asn Ala Gln
                645                 650                 655

Ala Ile Lys Lys Lys Leu Gly Lys Leu Gly Arg Gln Val Leu Pro Pro
                660                 665                 670

Ser Glu Leu Leu Asp His Leu Phe Phe His Tyr Glu Phe Gln Asn Gln
                675                 680                 685

Arg Phe Ser Ala Glu Val Leu Ser Ser Leu Arg Gln Leu Asn Leu Ala
                690                 695                 700

Gly Val Arg Met Thr Pro Val Lys Cys Thr Val Ala Ala Val Leu
705                 710                 715                 720

Gly Ser Gly Arg His Ala Leu Asp Glu Val Asn Leu Ala Ser Cys Gln
                725                 730                 735

Leu Asp Pro Ala Gly Leu Arg Thr Leu Pro Val Phe Leu Arg Ala
                740                 745                 750

Arg Lys Leu Gly Leu Gln Leu Asn Ser Leu Gly Pro Glu Ala Cys Lys
                755                 760                 765

Asp Leu Arg Asp Leu Leu His Asp Gln Cys Gln Ile Thr Thr Leu
770                 775                 780

Arg Leu Ser Asn Asn Pro Leu Thr Ala Ala Gly Val Ala Val Leu Met
785                 790                 795                 800

Glu Gly Leu Ala Gly Asn Thr Ser Val Thr His Leu Ser Leu His
                805                 810                 815

Thr Gly Leu Gly Asp Glu Gly Leu Glu Leu Leu Ala Ala Gln Leu Asp
                820                 825                 830

Arg Asn Arg Gln Leu Gln Glu Leu Asn Val Ala Tyr Asn Gly Ala Gly
                835                 840                 845

Asp Thr Ala Ala Leu Ala Leu Ala Arg Ala Ala Arg Glu His Pro Ser
                850                 855                 860

Leu Glu Leu Leu His Leu Tyr Phe Asn Glu Leu Ser Ser Glu Gly Arg
865                 870                 875                 880

Gln Val Leu Arg Asp Leu Gly Gly Ala Ala Glu Gly Gly Ala Arg Val
                885                 890                 895

Val Val Ser Leu Thr Glu Gly Thr Ala Val Ser Glu Tyr Trp Ser Val
                900                 905                 910

Ile Leu Ser Glu Val Gln Arg Asn Leu Asn Ser Trp Asp Arg Ala Arg
                915                 920                 925

Val Gln Arg His Leu Glu Leu Leu Leu Arg Asp Leu Glu Asp Ser Arg
                930                 935                 940
```

Gly Ala Thr Leu Asn Pro Trp Arg Lys Ala Gln Leu Leu Arg Val Glu
945                 950                 955                 960

Gly Glu Val Arg Ala Leu Leu Glu Gln Leu Gly Ser Ser Gly Ser
            965                 970                 975

<210> SEQ ID NO 3
<211> LENGTH: 11771
<212> TYPE: DNA
<213> ORGANISM: Homo sapiens

<400> SEQUENCE: 3

| | | | | | |
|---|---|---|---|---|---|
| acatggccaa | tggccgcgcg | ctctgcccgc | cccgcctcct | cgctgcggga | agggtcctgg | 60 |
| gccccgggcg | gcggtcgcca | ggtctcaggg | ccggggtac | ccgagtctcg | tttcctctca | 120 |
| gtccatccac | ccttcatggg | gccagagccc | tctctccaga | atctgagcag | caatgccgtt | 180 |
| tgctgaagac | aagacctata | agtatatctg | ccgcaatttc | agcaattttt | gcaatgtgga | 240 |
| tgttgtagag | attctgcctt | acctgccctg | cctcacagca | agagaccagg | atcgactgcg | 300 |
| ggccacctgc | acactctcag | ggaaccggga | caccctctgg | catctcttca | ataccccttca | 360 |
| gcggcggccc | ggctgggtgg | agtacttcat | tgcggcactg | aggggctgtg | agctagttga | 420 |
| tctcgcggac | gaagtggcct | ctgtctacca | gagctaccag | cctcggacct | cggaccgtcc | 480 |
| cccagaccca | ctggagccac | cgtcacttcc | tgctgagagg | ccaggccccc | ccacacctgc | 540 |
| tgcggcccac | agcatcccct | acaacagctg | cagagagaag | gagccaagtt | accccatgcc | 600 |
| tgtccaggag | acccaggcgc | cagagtcccc | aggagagaat | tcagagcaag | ccctgcagac | 660 |
| gctcagcccc | agagccatcc | caaggaatcc | agatggtggc | ccctggagt | cctcctctga | 720 |
| cctggcagcc | ctcagccctc | tgacctccag | cgggcatcag | gagcaggaca | cagaactggg | 780 |
| cagtacccac | acagcaggtg | cgacctccag | cctcacacca | tcccgtgggc | ctgtgtctcc | 840 |
| atctgtctcc | ttccagcccc | tggcccgttc | caccccccagg | gcaagccgct | tgcctggacc | 900 |
| cacagggtca | gttgtatcta | ctggcacctc | cttctcctcc | tcatcccctg | gcttggcctc | 960 |
| tgcagggggct | gcagagggta | aacagggtgc | agagagtgac | caggccgagc | ctatcatctg | 1020 |
| ctccagtggg | gcagaggcac | ctgccaactc | tctgccctcc | aaagtgccta | ccaccttgat | 1080 |
| gcctgtgaac | acagtggccc | tgaaagtgcc | tgccaaccca | gcatctgtca | gcacagtgcc | 1140 |
| ctccaagttg | ccaactagct | caaagcccccc | tggtgcagtg | ccttctaatg | cgctcaccaa | 1200 |
| tccagcacca | tccaaattgc | ccatcaactc | aacccgtgct | ggcatggtgc | catccaaagt | 1260 |
| gcctactagc | atggtgctca | ccaaggtgtc | tgccagcaca | gtccccactg | acgggagcag | 1320 |
| cagaaatgag | gagacccccag | cagctccaac | accccgccggc | gccactggag | gcagctcagc | 1380 |
| ctggctagac | agcagctctg | agaataggggg | ccttgggtcg | gagctgagta | agcctggcgt | 1440 |
| gctggcatcc | caggtagaca | gcccgttctc | gggctgcttc | gaggatcttg | ccatcagtgc | 1500 |
| cagcacctcc | ttgggcatgg | ggccctgcca | tggcccagag | gagaatgagt | ataagtccga | 1560 |
| gggcaccttt | gggatccacg | tggctgagaa | ccccagcatc | cagctcctgg | agggcaaccc | 1620 |
| tgggccacct | gcggacccgg | atggcggccc | caggccacaa | gccgaccgga | agttccagga | 1680 |
| gagggaggtg | ccatgccaca | ggccctcacc | tgggctctg | tggctccagg | tggctgtgac | 1740 |
| aggggtgctg | gtagtcacac | tcctggtggt | gctgtaccgg | cggcgtctgc | actagtgaag | 1800 |
| ccctgggctc | ttcccaccac | ccatctgttc | cgttcctgca | gtacctggg | cccctctccg | 1860 |
| aagccccttg | tcccttctt | ggggattgtg | gaggctgggt | cagaggggag | ttaagggact | 1920 |

```
gcaggcctgg cagcaggaca tgccttggct gaaccaagtc ctgagagcag catctctgtc   1980
cccacggtgc cttgtgtggg tccccgtcct tggctttctg ggtcctgggc tgccccagt    2040 gctccagacc ttccccactg gcaatccagg ttatcatcca tgtcctccag aggagcttcc   2100
tcctccaggc ctcagccctg ttggcccagg tggagcagga gggaccactg aacatgtgg    2160 tgcttgggaa tgcctctcct gttgcattgg tccctgaagg cctcagggca ggtatgtggt   2220
gtgtgggcga ctcacaaga cctgcctccc atcctggcag cccagcctga ccgttgca     2280 ttgaggcagg caggagcggc agggtggctg ctctccagga gcccaactgc cttgagttcc   2340
tgccccactg ggccccctcc cctgctgggc aatcctggga aggtctggag gttcctgtgg   2400
acctcaggga agccaggggc agctgtcagg cctgaggaag acctgtggag ctcctctcca   2460
gcctcctctt tccctcccct ctggtctcca ttctcttcag ctccctacat gggctgggga   2520
ggagacacct ggtgggcaga gctcaggcag aggtttggat tcagctccc tcacttccgg   2580 ggctgtgtgg ctttggcaga tgtcagactt ctggtcttgc ttctccacgt ggacagtgag   2640
tatctggctc attcttcact gggttcttct gagattgaac ctacaggtgt ttgccaagtg   2700
cctggcccag agcaagtggc cactgcttct cccatctctc tcctgcccaa cctggtagag   2760
ctgagggcat gagaggcaga gtgcacagtg gtcaagggtg cagctctgca gcacaggcag   2820
cctaggcctg cgtcccaacc tgcctctcac cagctctgtg accttgggca agggatttat   2880
ctgtctgtcc cttagttttc tcacctgtaa aaggaggata agtatatata tatatttccc   2940
agtgttgtga agattaaagg agtttatcga tgtaggtctt aggatgagtc ctggcattta   3000
ccaagggttg gatatatgtt attatcacta ttaagtgttg agggtccagg catgctgggc   3060
aacagggacc ccatctctac aaaaaagttt aaaaaattag ccaggcgtgg tggtgcacct   3120
gtcgtcttag ctactgggga ggctgaggtg ggaggatcac ttgagcccag aagcttgaag   3180
ctgcagtgag ctaggatcgt gccactgcac tccaacctgg gtgagagagc gagaccctgt   3240
ctcaagaaaa agaaaaatgc agagaaacag gagtcttggc tactcccttta gaggcagact   3300 cagaccctcc tgcctcacag ctttatcttt gtatttgccc cttactttat cttgtgcctt   3360
gagaaattgc tggggagaga ggtatgtcca ctgggcagct gtacaggatg gaggatatag   3420
ggcgtttcca ctcccagcag ccaggttccc tcaccccaag ctcacccact gttggggaga   3480
ttatctacaa taacaccaga aacacattgg ggtggattgg gggtatcctt atgggttctt   3540
ttcagggaac cattgctgga caaggcacag gagccacctc catttctgag ctctgcaagg   3600
gacaagaact agagccatca ggggctgggc tcactgtggc cccaccccaa gccgtcagcc   3660
tccagggatc tacaccctgc cttggctgct acagcttttt cactccactg ccctagggga   3720
gttcagcaac ctaatgatct ctatctctga acatctcttc atcccatgct ccaagtccag   3780
caacctgcac cctggaacca ggagtggacc ctacccgagc tgtctgtatt aatccccatc   3840
ccccaccacc aatcttaaaa agccctctgt ccccctaccc taaacccag ttaggtaccc    3900 atgctgggca ggtcagttaa caatttatgc acaggtacta gttttattgt attaccgttc   3960
cagggtagct ttgaaaaaag tatctcaaaa aggcaacatg ggccgagcgc agtggctcac   4020
gcctgtaatc ccagcacttt gggaggccaa ggtgggcaga tcgcctgagg tctggagttc   4080
aagaccagcc tggccaacag ggtgaaaccc cgtctctaca aaataagaa aattagccag   4140 gtgtagtggc agacgtctgt aatcccagct attcaggagg ctgaggcacg agaattccat   4200
gaacccagga tgcggaggtt gcagtgagcc gagattgtgc cactgcgctc agcctgggc   4260 gacagagtgg tattctgttt caaaaaaaaa aaaaaggca gtatgtagcc ccgaagactg   4320
```

```
ttgcccaagt ggtagaatgt tagcacacta ccagcctagg taaaaaatac aaaaagtaac    4380
tgggcatggc ggcgcccatc tatagtccca gctacatggg aggctgaggt gggaagataa    4440
gtcacttgag cccgccagga ggcggaggtt gtagtgagct gagatcgcac cactgcactc    4500
cagcctgggt gaccgagtga tactctgtct caaagaaaaa aaattataat tttagcacag    4560
taaccagcca tgatgggaga taccctgggt aaggcatgta gaaagggttg agggaccttc    4620
ccagtcccct agcccgcct cccatcctcc catcttttc ttttttcttt ttttagaga     4680 atcacccagc ctggagcgaa gtggtgcaat cataactcac tgtatcctta aactcccggg    4740
cttaagcgat cctcctgcct cagccttctg agtaactagg acttcaggta cctgtcacca    4800
tgcctggcta attaaatttt ttttctttt ttttttga gatggagtct tgctctgtca      4860
cccaggctgg agtgcagtgg cgcgatctca gctcactgcg acctccacct cctgggttca    4920
ggccattctc ccgcctcagc ctccagagta gctgggacta caggcgcctg ccaccacgcc    4980
tggctaattt ttttgcactt ttagtagaga cggggtttca ctgtgttagc caggatggtc    5040
tcgatctcct gaccttgtga tccgcccgcc tcggcctccc aaagtgctgg gattacaggc    5100
gtgagccacc gcgcccagcc aaattaaatt ttttatagag atgaggtcat gctgttatgt    5160
tgcccaggtt ggcctcatga gatcttgcct tagcctccca aagtgctggg attacagatg    5220
tgagacactg cacccaaacc ccaccacttt ttttttcct ttttctttt ttgagacagt     5280 cttactccgt tgcccaggct ggagtgtagt ggcatgatct cagctcactg caacctccgc    5340
ctcccgggtt caagcaattc tcctgcctca gcctcccgag tagctgggat tacagaggcc    5400
tgccaccaca cccgactaat tttcgtattt ttagtagaga cggggtttct ccatgttggc    5460
caggctgttc ttgaactcct gacctcaagt gctccacctg cgttggcttc ccaaagtgct    5520
gggatacagg agtgagccac tgcgcctggc tgatcccagc acttttcaaa tgatgccgct    5580
caaagccgtg acttggccta cttgtgaacag caaacttgtt gctgctgttg tcaacctgaa    5640
ggcctctcaa atgccagctt caagcagggt gtgaattggc cagtgtcaga tctcaggagt    5700
cctgtgttga gagtgtggct ttcagctgcg gggagctgca cttggtgggg aaagccaggc    5760
aggtcaccct cacagccaga taatgtggag gtcagaaccc aaggaaggga gtgagacctc    5820
cactcccagt gggggacctg gccacccatc cttggggacc tgagaaagcg tacttcacct    5880
tggggtgaag gctgggtggg gccagaggga ccagtgccct cctcagtgct tagggggcaga   5940 gccacctgca gcaatggtat ctgcatatta gcccctctcc accttctttc tcccgctgaa    6000
tcatttccct caaagcccaa gagctgtcac tgcttcttc tccctgggaa gaatgcgtgg     6060
actctgcctg gtgatagact gaagccagaa cagtgccaca ccctcgcctt aattccttgc    6120
taggtgttct cagatttatg agacttctta gtcaaatatg agggaggttg gatgtggtgg    6180
cttgtgcctg taatcccagc attttgggaa gccgaggtgg gaggatccct tgaagccagg    6240
agtttgagac aagcctgggc aacaaagcaa gaccctatct ctaaaaaaaa aaaaaaaaa    6300 aaaaaaaaa aaaaaaaaa aaaatctagg agatgctctt taccctgcct ggcctcaaac     6360
tattaatagc ttcctttgag caacattatt tattatgaac tttcaaacac aaaaaagtag    6420
agagagtaga ataacaaatc cccatgagcc catcacccaa cttcagtaat tatcaattca    6480
tggccatctt gttcacccct gcctgcttcc ctgcttcccc tcattctgca gaggttcttt    6540
tcttttgaga cagagtgttg ctctgttgcc caggctggag tgcagtggtg caacttcggc    6600
tcactgcaac ctccgcctcc caggttcaag tgattctcct gcttcagcct ctcaagtagc    6660
```

| | |
|---|---|
| tgggattaca gatgcccgcc accacacctg gctaattttc gtattttttgt tagagatggg | 6720 |
| gtttcaccat gttggccagg ctggtctcga actcctgacc tcaagtgatc cgcccgcctt | 6780 |
| ggcctcccaa aatgctggga ttacaggtgt gaaccacggt gcctggccac tgtacaggtt | 6840 |
| atttatagaa gttggagagt gaagggttga gaaagccaag gggcagatgc gggtctggag | 6900 |
| gattttgtgc ctaaggccct ctctttgctc ccagacagca tgaagtaaca atgaggcatc | 6960 |
| cacctcttgg ttttgtggcc tctgtggatg acgtctctca ccttgaacca gttcagagtt | 7020 |
| ggagtagcgc aggatcctgt cttcagagga ggggccgaag cgggttcctc tgttgtcaag | 7080 |
| ctctttggag gtgcctggct gctactactg tcccagagag gtgatgatga atgatgggtg | 7140 |
| tgtccagtgg cagtttgccc cactgaggca ggggcttcca ctaggccctg acagagccct | 7200 |
| tccagcaggc agaaatccct gtgctaggca agattcaaac tccgtagcat gtctcctgct | 7260 |
| cccatctctt aggaatggag tccttcaggc cttgagtccc acattttcca tgatgctcca | 7320 |
| ttaagcagct gatagcaccc ccacctccag ggaaagtgag ttcagagtcc ttggtctaat | 7380 |
| gcatctgtgt tgaaattgag gccttcccct gtgttcacct ttctgctctt tttcttttag | 7440 |
| cccaaggcta tgaaggcctc attcggtgct gggcatggtc actcctagca ttcctcactc | 7500 |
| tgttgctaac agcaacagca ataataataa gggttacaac ttactccata ccttactgtc | 7560 |
| tgccaggcat taagctaagt gctttacata tattaagtca tttaatcctc ataatgaccc | 7620 |
| tatgaaagag ataccatctc aacccaattg acagctggtt tgcaagatta ggagggatga | 7680 |
| aggacccagg ggacaatgcg agggaaaact ctgaccccgg ggccccaggc tggatgttct | 7740 |
| ttatgcctgt gaaccacagc ttatcacatg tctggagtta gggaccccac ttaaagtgag | 7800 |
| attttggctg gaggtggtgg atcataccta taatcccagc actttgggag accaaggcag | 7860 |
| aaggactgct tgaggccagg agttcaaaac cagtgtaggt aacagctaga ccctatctct | 7920 |
| acaaaaaatt taaaaattag ctgggtgtgg tggtatgtgc ctcaagttcc agctactcag | 7980 |
| gaggctgagg tgggaggatc acttgagcac aggagtttga agttacagtg agctatgatg | 8040 |
| gcaccactgc acttcagcct aggcaacaga gggagaccct gtctttaaag tacatagagg | 8100 |
| ttttttcacac caacacatct ctgcccagtg tgccaacatc tgccacctgc tataaatagta | 8160 |
| ctataacact caatatgtaa ttaatgtagt ctcagggatg ttatgacaat atgattacaa | 8220 |
| ctatcacgtg tgtgcccagc caggctcaat gccccaggct gggcgaggtg gggcagggga | 8280 |
| cacagcctaa aatgccaggc ctcaggaagc catttggttt agcagacatt gtttattaaa | 8340 |
| ggagttacct atgccagatc gaaggcctaa gatgattaag acactatgag tgccttcaag | 8400 |
| tggttgggga cgttcatgat tgtggtacag acaaataggc tttcacatca ttctttttatg | 8460 |
| taatcataca acagatattt gcacctacat gtgcagagca ctgtgatagg cctcagtgac | 8520 |
| acagaataat acggcaaaga ccccacccga tgagccccct cccaccaccc accagtacag | 8580 |
| taggggtgg tttaatggag tgttcctgga atatgaagtg ggggcaggca ttaggggtgg | 8640 |
| caaagggaca agtgtttatc tgatcagtta tgtactgttt ataataagta aatcagcaga | 8700 |
| gggggaataa tacttagaac ctatagagag taaatctgac aagatgaaat gctgatgaaa | 8760 |
| atatggagga aatgaaactc tcatgggttt tgcagggaat ctaagtcagt gctgtgttgt | 8820 |
| gaatgtaggt gtacccttttg aattcatatg ttgaatccta accccaaag caatggcatt | 8880 |
| aagaggtggg gcctttgggg ctgggtatgg tggctcatga ctgtaatccc agcactttgg | 8940 |
| gatgctggca gggggcagat cacttgaagc caggagtctg agatcagcct ggccaacatg | 9000 |
| gtgaaacccc atctgtacta aaaatacaaa aattagccag gtgtgatggc gtacatctgt | 9060 |

```
aatttcagcc actcgggagg ctgagacagg agaatagctt gaacccagta ggtggagatt    9120
tcagtgagcc gagatcgtgc cactgcactc cagcctgggt gacagagcga gactccatct    9180
caaaaaaata ataaagatgt ggggcctgtg ggaggtggtt aggtcatgag ggtggagatc    9240
atgaatgggg ttagcacctt ataaaacagg cttgagggag cccttctgtc ccttctacca    9300
tgtgtggatg cagtgagaag gcaccgtatc tctgaagcag agagcccgcc ctggacactg    9360
gatctgctgg caccttgatc ttggacttcc cagcctctag aactgtgaga ataattttt    9420
tgttgtttac aaattaccca ggctaaggtg tttcattgta acctgaatgg accaagctgg    9480
tgtgaccctg ttggaaaact ggcagtatct accaaaagcc gaacatacgt ataaactgat    9540
ccagcagttc cactcctggg tatgtacacc acagaaagct atgtccaccg agacattggc    9600
aagaatgttt ctaaccacac gctgactgta gccccaaacc tgaaacaacc caatgtccca    9660
tccaccaacc caaatgtcca tccacagttg aagctacagt gaagtcacag ggtcgaatac    9720
tactgcacag caacgaatat gaatgaaaat atcgctatgc acagcaacat ggataaattt    9780
cacagacatg aggtcaagca aaagaggtca gagtcctcat catcaagaga gaattcattg    9840
tatgattctc ttcctacaaa aagtacagaa ataagcaaaa ctgatccatg gtgttagaag    9900
ccaggggaac agttaacagg ggagggatac tggggagggg catcctggag tgctggtcta    9960
cctcatctgg gtgttgattt cacgagtatt gtcagtttgt ttccagactc cctgttggag   10020
atgtggaaat aaaaaccacc taaacaagag cagagaggcc atttggtcaa agtttgcaaa   10080
ggagtcagcc atgattgctt gtatttggca ggggtcaaag gcaggcaggg actgtgaaat   10140
gttatagtgg aaaaaaaggg aaggctctgg gtgtgctgtg attggagatt gttggcatgg   10200
ggacagagcg gactaactgg aggggcatct ttggttggtt ggggggggtat atttggcttt   10260
ctctggttgg tctggagttg aagaggggg tgtggtggc ggggattggg aagaagctgg    10320
cagccactaa gttcagactg ttctgggtcc gattgctgct gaggctgtgg tttggcttcc   10380
ttggcttccc aggctggtca tgggtttctg gccagagtct attgtcatat gtggcctggc   10440
cattgtccag ttgtatgttc agtctcttgg aaggaagggt attgactctg agagggcca   10500
ccatcgctgg aatgggggac acacagtact tcctccagct gcctacaccc cctagggtc    10560
agtggcgcct gcctgtgagg gtgagcccaa tggctagagg gctctgctcc aagtcattgc   10620
ttactacacc cacaaacatt cttcgttctt taaggcctaa cttaaagccc agatcctaca   10680
ggaaaccttg attagacccc tctctttatt aagcttccta agatcaaacc ctgcttttgt   10740
gtaaatgctg acctccttgc ctacattttta aaacctaga gctgggcatg atggccccag   10800
cctgtaatcc cagtgattca ggagactgag gtgggaggat tgctagaagc caggagttcg   10860
agaccagcct gggtaacata gctagaccac atctcttaaa ataaaatagt taatttagcc   10920
aggcatgatg atatatgcct gtagtcccaa ctacttggaa ggctgaggtg tgaggatctt   10980
tgagcccggg aggtcgaggc tacagtaagc tatgatctca ccactgtact ccagcctggg   11040
tgacagagcg agacccagac tcaaaaaata aaataaaaa ccctgaatat cttccttcta   11100
cttcttcagt gctgttttta tttaaaaaaa aaaaaaacca gccaaaacca caactttta   11160
ctgaagtgta atgtaaatgc tgtaaaaggc agtgaaaggc acaagggagg tggagggta   11220
ggaagggtgg aagtggcggg aggaagtggc agggcaggca aaatgaaggg aagccctggg   11280
ttcttgtcct gcatccgcag ccagctccca ctttcctcac cctccaggac ctgtaaactg   11340
tgaggctgga ccagttatgt caaatctgtc ctcccccaga gctcagtccc tctgcccttg   11400
```

-continued

```
ggtgtccttg gcacaaggca ggctaggctg caccagcttc ctccatctcc gtcctgcctc    11460
ccccatcccc aggtgccatt cccacaccat ctgaatcact gatttcctcg caatcagacg    11520
ctatcttcca gttaatcact tcgcttgtat ttaacataag aaagaaaaac cctttcatta    11580
tcacatacag ctggaaatcg gcttcttgca ggaggcgtat ccaaaggaat tggagaagag    11640
ataaactggt aattggtgaa agaattactt taatttttt tcctacttgc tgtcatgatg     11700
atgtccttag aattgtgagc ccgtggacac ttctgtacaa taaatctgct attattactt    11760
ctagaactac a                                                         11771
```

<210> SEQ ID NO 4
<211> LENGTH: 540
<212> TYPE: PRT
<213> ORGANISM: Homo sapiens

<400> SEQUENCE: 4

```
Met Pro Phe Ala Glu Asp Lys Thr Tyr Lys Tyr Ile Cys Arg Asn Phe
1               5                   10                  15

Ser Asn Phe Cys Asn Val Asp Val Val Glu Ile Leu Pro Tyr Leu Pro
                20                  25                  30

Cys Leu Thr Ala Arg Asp Gln Asp Arg Leu Arg Ala Thr Cys Thr Leu
            35                  40                  45

Ser Gly Asn Arg Asp Thr Leu Trp His Leu Phe Asn Thr Leu Gln Arg
        50                  55                  60

Arg Pro Gly Trp Val Glu Tyr Phe Ile Ala Ala Leu Arg Gly Cys Glu
65                  70                  75                  80

Leu Val Asp Leu Ala Asp Glu Val Ala Ser Val Tyr Gln Ser Tyr Gln
                85                  90                  95

Pro Arg Thr Ser Asp Arg Pro Asp Pro Leu Glu Pro Pro Ser Leu
                100                 105                 110

Pro Ala Glu Arg Pro Gly Pro Pro Thr Pro Ala Ala His Ser Ile
            115                 120                 125

Pro Tyr Asn Ser Cys Arg Glu Lys Glu Pro Ser Tyr Pro Met Pro Val
        130                 135                 140

Gln Glu Thr Gln Ala Pro Glu Ser Pro Gly Asn Ser Glu Gln Ala
145                 150                 155                 160

Leu Gln Thr Leu Ser Pro Arg Ala Ile Pro Arg Asn Pro Asp Gly Gly
                165                 170                 175

Pro Leu Glu Ser Ser Ser Asp Leu Ala Ala Leu Ser Pro Leu Thr Ser
            180                 185                 190

Ser Gly His Gln Glu Gln Asp Thr Glu Leu Gly Ser Thr His Thr Ala
        195                 200                 205

Gly Ala Thr Ser Ser Leu Thr Pro Ser Arg Gly Pro Val Ser Pro Ser
    210                 215                 220

Val Ser Phe Gln Pro Leu Ala Arg Ser Thr Pro Arg Ala Ser Arg Leu
225                 230                 235                 240

Pro Gly Pro Thr Gly Ser Val Val Ser Thr Gly Thr Ser Phe Ser Ser
                245                 250                 255

Ser Ser Pro Gly Leu Ala Ser Ala Gly Ala Ala Glu Gly Lys Gln Gly
            260                 265                 270

Ala Glu Ser Asp Gln Ala Glu Pro Ile Ile Cys Ser Ser Gly Ala Glu
        275                 280                 285

Ala Pro Ala Asn Ser Leu Pro Ser Lys Val Pro Thr Thr Leu Met Pro
    290                 295                 300
```

-continued

```
Val Asn Thr Val Ala Leu Lys Val Pro Ala Asn Pro Ala Ser Val Ser
305                 310                 315                 320

Thr Val Pro Ser Lys Leu Pro Thr Ser Ser Lys Pro Pro Gly Ala Val
            325                 330                 335

Pro Ser Asn Ala Leu Thr Asn Pro Ala Pro Ser Lys Leu Pro Ile Asn
            340                 345                 350

Ser Thr Arg Ala Gly Met Val Pro Ser Lys Val Pro Thr Ser Met Val
            355                 360                 365

Leu Thr Lys Val Ser Ala Ser Thr Val Pro Thr Asp Gly Ser Ser Arg
        370                 375                 380

Asn Glu Glu Thr Pro Ala Ala Pro Thr Pro Ala Gly Ala Thr Gly Gly
385                 390                 395                 400

Ser Ser Ala Trp Leu Asp Ser Ser Ser Glu Asn Arg Gly Leu Gly Ser
            405                 410                 415

Glu Leu Ser Lys Pro Gly Val Leu Ala Ser Gln Val Asp Ser Pro Phe
            420                 425                 430

Ser Gly Cys Phe Glu Asp Leu Ala Ile Ser Ala Ser Thr Ser Leu Gly
            435                 440                 445

Met Gly Pro Cys His Gly Pro Glu Glu Asn Glu Tyr Lys Ser Glu Gly
    450                 455                 460

Thr Phe Gly Ile His Val Ala Glu Asn Pro Ser Ile Gln Leu Leu Glu
465                 470                 475                 480

Gly Asn Pro Gly Pro Pro Ala Asp Pro Asp Gly Gly Pro Arg Pro Gln
            485                 490                 495

Ala Asp Arg Lys Phe Gln Glu Arg Glu Val Pro Cys His Arg Pro Ser
            500                 505                 510

Pro Gly Ala Leu Trp Leu Gln Val Ala Val Thr Gly Val Leu Val Val
            515                 520                 525

Thr Leu Leu Val Val Leu Tyr Arg Arg Arg Leu His
    530                 535                 540
```